(12) United States Patent
Soane et al.

(10) Patent No.: US 11,471,852 B2
(45) Date of Patent: Oct. 18, 2022

(54) SYSTEMS AND METHODS FOR PROCESSING GASES

(71) Applicant: TRANSFORM MATERIALS LLC, Riviera Beach, FL (US)

(72) Inventors: David S. Soane, West Palm Beach, FL (US); James Nathan Ashcraft, Jupiter, FL (US); Jason Samuel Hummelt, Palm Beach Gardens, FL (US); Mark Ellis Soderholm, Palm Beach Gardens, FL (US); Mathew Leeds, Palm Beach Gardens, FL (US); Alexander Olson Santana, Tequesta, FL (US); Matthew Elijah O'Reilly, Riviera Beach, FL (US); Charles E. Ocampo, Palm Beach Gardens, FL (US)

(73) Assignee: Transform Materials LLC, Riviera Beach, FL (US)

( * ) Notice: Subject to any disclaimer, the term of this patent is extended or adjusted under 35 U.S.C. 154(b) by 0 days.

(21) Appl. No.: 17/402,937

(22) Filed: Aug. 16, 2021

(65) Prior Publication Data

US 2022/0080379 A1 Mar. 17, 2022

Related U.S. Application Data

(63) Continuation of application No. 17/155,760, filed on Jan. 22, 2021, which is a continuation-in-part of application No. 16/548,378, filed on Aug. 22, 2019.
(Continued)

(51) Int. Cl.
*B01J 19/12* (2006.01)
*B01D 53/00* (2006.01)
(Continued)

(52) U.S. Cl.
CPC .......... *B01J 19/126* (2013.01); *B01D 53/002* (2013.01); *B01D 53/047* (2013.01);
(Continued)

(58) Field of Classification Search
CPC B01J 19/245; B01J 19/081; B01J 2219/0004; B01J 2219/0898; B01J 19/126;
(Continued)

(56) References Cited

U.S. PATENT DOCUMENTS

| 3,519,517 A | 7/1970 | Dench |
| 3,663,394 A | 5/1972 | Kawahara |

(Continued)

FOREIGN PATENT DOCUMENTS

| EP | 0461683 A2 | 12/1991 |
| EP | 1936656 A1 | 6/2008 |

(Continued)

OTHER PUBLICATIONS

Safetygram13—Acetylene, Air Products and Chemicals, Inc., 2014.
(Continued)

*Primary Examiner* — Nicholas A Smith
(74) *Attorney, Agent, or Firm* — Elmore Patent Law Group, P.C.; Mahreen Chaudhry Hoda; Carolyn S. Elmore

(57) ABSTRACT

The invention includes a gas processing system for transforming a hydrocarbon-containing inflow gas into outflow gas products, where the system includes a gas delivery subsystem, a plasma reaction chamber, and a microwave subsystem, with the gas delivery subsystem in fluid communication with the plasma reaction chamber, so that the gas delivery subsystem directs the hydrocarbon-containing inflow gas into the plasma reaction chamber, and the microwave subsystem directs microwave energy into the plasma reaction chamber to energize the hydrocarbon-containing inflow gas, thereby forming a plasma in the plasma reaction
(Continued)

chamber, which plasma effects the transformation of a hydrocarbon in the hydrocarbon-containing inflow gas into the outflow gas products, which comprise acetylene and hydrogen. The invention also includes methods for the use of this gas processing system.

27 Claims, 27 Drawing Sheets

Related U.S. Application Data

(60) Provisional application No. 63/052,524, filed on Jul. 16, 2020, provisional application No. 63/019,851, filed on May 4, 2020, provisional application No. 62/986,998, filed on Mar. 9, 2020, provisional application No. 62/969,494, filed on Feb. 3, 2020, provisional application No. 62/793,763, filed on Jan. 17, 2019, provisional application No. 62/736,206, filed on Sep. 25, 2018, provisional application No. 62/721,863, filed on Aug. 23, 2018.

(51) Int. Cl.
| | |
|---|---|
| *B01D 53/04* | (2006.01) |
| *B01D 53/047* | (2006.01) |
| *B01D 53/22* | (2006.01) |
| *B01D 53/18* | (2006.01) |
| *C07C 2/76* | (2006.01) |
| *C07C 2/80* | (2006.01) |
| *C07C 11/24* | (2006.01) |
| *C07C 17/08* | (2006.01) |
| *H05H 1/46* | (2006.01) |
| *B01J 19/24* | (2006.01) |
| *B01J 19/08* | (2006.01) |

(52) U.S. Cl.
CPC ......... *B01D 53/0462* (2013.01); *B01D 53/18* (2013.01); *B01D 53/229* (2013.01); *C07C 2/76* (2013.01); *C07C 2/80* (2013.01); *C07C 11/24* (2013.01); *C07C 17/08* (2013.01); *H05H 1/4622* (2021.05); *B01D 2256/16* (2013.01); *B01D 2256/24* (2013.01); *B01D 2257/7022* (2013.01); *B01J 19/081* (2013.01); *B01J 19/245* (2013.01); *B01J 2219/0004* (2013.01); *B01J 2219/0898* (2013.01); *C01B 2203/0277* (2013.01); *C01B 2203/062* (2013.01); *C01B 2203/0861* (2013.01); *C01B 2203/1235* (2013.01)

(58) Field of Classification Search
CPC .......... B01J 2219/0896; B01D 53/002; B01D 53/0462; B01D 53/047; B01D 53/18; B01D 53/229; B01D 2256/16; B01D 2256/24; B01D 2257/7022; C01B 3/24; C01B 32/318; C01B 2203/0277; C01B 2203/062; C01B 2203/0861; C01B 2203/1235; C07C 17/08; C07C 2/76; C07C 2/80; C07C 11/24; H05H 1/4622
See application file for complete search history.

(56) References Cited

U.S. PATENT DOCUMENTS

| | | | |
|---|---|---|---|
| 4,574,038 A | 3/1986 | Wan | |
| 4,866,346 A | 9/1989 | Gaudreau et al. | |
| 4,975,164 A | 12/1990 | Ravella et al. | |
| 5,015,349 A | 5/1991 | Suib et al. | |
| 5,053,575 A | 10/1991 | Nikravech et al. | |
| 5,131,993 A | 7/1992 | Suib et al. | |
| 5,181,998 A | 1/1993 | Murphy et al. | |
| 5,205,912 A | 4/1993 | Murphy | |
| 5,205,915 A | 4/1993 | Ravella et al. | |
| 5,277,773 A | 1/1994 | Murphy | |
| 5,328,577 A | 7/1994 | Murphy | |
| 5,736,092 A | 4/1998 | Apte et al. | |
| 5,874,705 A | 2/1999 | Duan | |
| 5,972,175 A | 10/1999 | Tanner et al. | |
| 5,993,761 A * | 11/1999 | Czernichowski | ...... B01J 19/088 |
| | | | 204/170 |
| 6,156,114 A | 12/2000 | Bell et al. | |
| 6,362,449 B1 | 3/2002 | Hadidi et al. | |
| 6,409,851 B1 | 6/2002 | Sethuram et al. | |
| 6,582,778 B2 | 6/2003 | Namiki et al. | |
| 6,602,920 B2 | 8/2003 | Hall et al. | |
| 6,696,662 B2 | 2/2004 | Jewett et al. | |
| 6,916,400 B2 | 7/2005 | Moisan et al. | |
| 7,008,970 B2 | 3/2006 | Kong et al. | |
| 7,170,027 B2 | 1/2007 | Kurashima et al. | |
| 7,183,451 B2 | 2/2007 | Gattis et al. | |
| 7,232,975 B2 | 6/2007 | Kong et al. | |
| 7,252,297 B1 | 8/2007 | Barritt et al. | |
| 7,497,922 B2 | 3/2009 | Kumar et al. | |
| 7,915,462 B2 | 3/2011 | Gattis et al. | |
| 7,915,465 B2 | 3/2011 | Gattis et al. | |
| 7,915,466 B2 | 3/2011 | Gattis et al. | |
| 8,636,960 B2 | 1/2014 | Spitzl et al. | |
| 8,680,424 B2 | 3/2014 | Kobayashi et al. | |
| 8,776,719 B2 | 7/2014 | Radoiu et al. | |
| 8,968,588 B2 | 3/2015 | Zhao et al. | |
| 9,051,526 B2 | 6/2015 | Markowz et al. | |
| 9,095,835 B2 | 8/2015 | Skoptsov et al. | |
| 9,142,389 B2 | 9/2015 | Wort et al. | |
| 9,212,058 B2 | 12/2015 | De | |
| 9,227,169 B2 | 1/2016 | Spitzl et al. | |
| 9,293,302 B2 | 3/2016 | Risby et al. | |
| 9,308,513 B2 | 4/2016 | Bricker et al. | |
| 9,409,161 B2 | 8/2016 | Bishop et al. | |
| 9,484,191 B2 | 11/2016 | Winkler | |
| 9,573,608 B2 | 2/2017 | Glass | |
| 9,574,086 B2 | 2/2017 | Johnson et al. | |
| 9,623,397 B2 | 4/2017 | Skoptsov et al. | |
| 9,682,359 B2 | 6/2017 | Skoptsov et al. | |
| 9,758,444 B2 | 9/2017 | Spitzl | |
| 9,767,992 B1 | 9/2017 | Stowell et al. | |
| 9,812,295 B1 | 11/2017 | Stowell | |
| 9,862,602 B1 | 1/2018 | Riso et al. | |
| 9,862,606 B1 | 1/2018 | Cook et al. | |
| 9,909,215 B2 | 3/2018 | Holber et al. | |
| 9,987,611 B1 | 6/2018 | Strohm et al. | |
| 9,997,322 B2 | 6/2018 | Kong et al. | |
| 9,997,334 B1 | 6/2018 | Anzelmo et al. | |
| 2004/0149700 A1 | 8/2004 | Bayer et al. | |
| 2006/0163054 A1 | 7/2006 | Spitzl et al. | |
| 2007/0163678 A1 | 7/2007 | Kim | |
| 2007/0274893 A1 | 11/2007 | Wright et al. | |
| 2008/0029030 A1 | 2/2008 | Goto et al. | |
| 2008/0277265 A1 * | 11/2008 | Tsangaris | ................ C01B 3/386 |
| | | | 204/157.15 |
| 2009/0205254 A1 | 8/2009 | Zhu et al. | |
| 2011/0163462 A1 | 7/2011 | Lang et al. | |
| 2011/0190565 A1 | 8/2011 | Novoselov et al. | |
| 2012/0034135 A1 | 2/2012 | Risby | |
| 2012/0082913 A1 | 4/2012 | Hyde et al. | |
| 2012/0103790 A1 | 5/2012 | Krull et al. | |
| 2012/0186972 A1 | 7/2012 | Li et al. | |
| 2013/0213795 A1 | 8/2013 | Strohm et al. | |
| 2014/0058085 A1 | 2/2014 | Rende et al. | |
| 2014/0159572 A1 * | 6/2014 | Risby | ................ H01J 37/32357 |
| | | | 315/39.51 |
| 2014/0239232 A1 | 8/2014 | Staton et al. | |
| 2015/0041309 A1 * | 2/2015 | Spitzl | ...... H01J 37/32 |
| | | | 204/157.15 |
| 2015/0218383 A1 | 8/2015 | Johnson et al. | |
| 2015/0258523 A1 | 9/2015 | Skoptsov et al. | |
| 2016/0362351 A1 * | 12/2016 | Nagaki | ...... B01J 21/08 |
| 2018/0099871 A1 | 4/2018 | Tanner et al. | |
| 2018/0138017 A1 | 5/2018 | Stowell | |

(56) References Cited

U.S. PATENT DOCUMENTS

| | | | |
|---|---|---|---|
| 2019/0046946 A1* | 2/2019 | Strohm | B01J 19/126 |
| 2019/0046947 A1* | 2/2019 | Strohm | B01J 19/126 |
| 2019/0185325 A1 | 6/2019 | Tanner et al. | |
| 2020/0062591 A1 | 2/2020 | Soane et al. | |

FOREIGN PATENT DOCUMENTS

| | | |
|---|---|---|
| GB | 1149473 A | 4/1969 |
| RU | 2522636 C1 | 7/2014 |
| WO | 9641505 A1 | 12/1996 |
| WO | 2006037991 A2 | 4/2006 |
| WO | 2007086875 A1 | 8/2007 |
| WO | 2010094969 A1 | 8/2010 |
| WO | 2010094972 A1 | 8/2010 |
| WO | 2012023858 A1 | 2/2012 |
| WO | 2013149723 A1 | 10/2013 |
| WO | 2016089994 A1 | 6/2016 |

OTHER PUBLICATIONS

English translation of Chapter 4 and from Reaktionen gesättigter Kohlenwasserstoffe in der Gasphase und an Oberflächen Dissertation, 2015.

American Chemical Society National Historic Chemical Landmarks. Discovery of the Commercial Processes for Making Calcium Carbide and Acetylene. http://www.acs.org/content/acs/en/education/whatischemistry/landmarks/calciumcarbideacetylene.html, (accessed Aug. 20, 2018).

Hydrogen from biomethane; gasoline & diesel from tree residue; cellulosic ethanol among new proposed California LCFS fuel pathways, (http://www.greencarcongress.com/2015/12/hydrogen-from-biomethane-gasoline-diesel-fromtree-residue-cellulosic-ethanolamong-new-proposed-cal.html), 1-29. Retrieved from the internet May 21, 2018.

Abdel-Aal, H. K. et al., "Challenges and Progress in Methane Conversion: An Assessment", Chemical Engineering, 1, 2016, 1-11.

Abney, M. B. et al., "Evaluation of Sorbents for Acetylene Separation in Atmosphere Revitalization Loop Closure", 41st International Conference on Environmental Systems Jul. 17-21, 2011, Portland, Oregon, American Institute of Aeronautics and Astronautics.

Abney, M. B. et al., "Hydrogen Purification in Support of Plasma Pyrolysis of Sabatier Derived Methane", 45th International Conference on Environmental Systems Jul. 12-16, 2015, Bellevue, Washington, International Conference on Environmental Systems.

Atwater, J. E. et al., "Development and Testing of a Prototype Microwave Plasma Reactor for Hydrogen Recovery from Sabatier Waste Methane", Downloaded from SAE International by University of Liverpool, Sunday, Sep. 9, 2018.

Balachandran, U. et al., Hydrogen Separation Membranes, Energy Systems Division, Argonne National Laboratory Annual Report for FY 2010, Report Date: Jan. 31, 2011. http://www.osti.gov/bridge.

Bartholome, E. et al., "The BASF-process for production of acetylene by partial oxidation of gaseous hydrocarbons", Special Supplement to Chemical Engineering Science, vol. 3, 1954.

Bin, D. et al., "Study on the hydrogenation coupling of methane", Science in China (Series B), 44(2), 2001, 191-195.

Blanksby, S. J. et al., "Bond Dissociation Energies of Organic Molecules", American Chemical Research, Accounts of Chemical Research, 2002.

Bullerwell, J. et al., "Stability of acetylene/methane and acetylene/hydrogen/methane gas mixtures at elevated temperatures and pressures", Fuel, 89, 2010, 254-256.

Chaichumporn, C. et al., "Design and Construction of 2.45 GHz Microwave Plasma Source at Atmospheric Pressure", 2nd International Science, Social-Science, Engineering and Energy Conference 2010: Engineering Science and Management, Procedia Engineering, 8, 2011, 94-100.

Chen, C-K. et al., "Modelling the discharge region of a microwave generated hydrogen plasmA", J. Phys. D: Appl. Phys., 32, 1999, 688-698.

Chen, H. L. et al., "Review of plasma catalysis on hydrocarbon reforming for hydrogen production—Interaction, integration, and prospects", Applied Catalysis B: Environmental, 85, 2008, 1-9.

Copenhaver, J. et al., "Acetylene and Carbon Monoxide Chemistry", Reinhold Publishing Corporation, New York, NY, 1949.

Fincke, J. R. et al., "Plasma Thermal Conversion of Methane to Acetylene", Plasma Chemistry and Plasma Processing, 22(1), Mar. 2002.

Fincke, J. R. et al., "Thermal Conversion of Methane to Acetylene Final Report", Idaho National Engineering and Environmental Laboratory, Idaho Falls, Idaho, Jan. 2000.

Fridman, A. Plasma Chemistry—Table of Contents, pp. 209-214 and 589-602. rexel University, Cambridge University Press, www.cambridge.org, 2008.

Gallon, H. J. "Dry Reforming of Methane Using Non-Thermal Plasma-Catalysis", A thesis submitted to The University of Manchester for the degree of Doctor of Philosophy in the Faculty of Engineering and Physical Sciences, 2010.

Gannon, R. E. "Acetylene from Hydrocarbons", Kirk-Othmer Encyclopedia of Chemical Technology, 2000.

Gruen, D. M. et al., "Carbon dimer, C2, as a growth species for diamond films from methane/hydrogen/argon microwave plasmas", Journal of Vacuum Science & Technology A, 13, 1995, 1628.

Gu, Y. "The New Generation Microwave Plasma Assisted CVD Reactor for Diamond Synthesis", Dissertation submitted to Michigan state University, 2011.

Hassouni, K. et al., "Investigation of chemical kinetics and energy transfer in a pulsed microwave H2/CH4 plasma", Plasma Sources Sci. Technol., 10, 2001, 61-75.

Heintze, M. et al., "Mechanism of C2 hydrocarbon formation from methane in a pulsed microwave plasma", J. Applied Physics, 92(12), 2002.

Heintze, M. et al., "Methane conversion into acetylene in a microwave plasma: Optimization of the operating parameters", J. Applied Physics, 92(5), 2002.

Holmen, A. et al., "Pyrolysis of natural gas: chemistry and process concepts", Fuel Processing Technology, 42, 1995, 249-267.

Huang, J. et al., "Dimerization of Methane through Microwave Plasmas", J. Phys. Chem., 97, 1993, 9403-9407.

Huang, J. et al., "Methane Dimerization via Microwave Plasmas", Res. Chem. Intermed, 20(1), 1994, 133-139.

Hunt, J. et al., "Microwave-Specific Enhancement of the Carbon-Carbon Dioxide (Boudouard) Reaction", J. Phy. Chem. C, 117, 2013, 26871-26880.

Indarto, A. "Methane Conversion in Plasma", Jun. 2010, Retrieved from the Internet <<https://www.researchgate. net/publication/286756315.>>.

Jasinski, M. et al., "Atmospheric pressure microwave plasma source for hydrogen production", International Journal of hydrogen energy, 38, 2013, 11473-11483.

Jasinski, M. et al., "Hydrogen Production via Methane Reforming Using Various Microwave Plasma Sources", Chem. Listy, 102, 2008, s1332-s1337.

Jasinski, M. et al., "Production of hydrogen via conversion of hydrocarbons using a microwave plasma", Journal of Physics D: Applied Physics, 44(19), 2011.

Jasinski, M. et al., "Production of hydrogen via methane reforming using atmospheric pressure microwave plasma", Journal of Power Sources, 181, 2008, 41-45.

Kawahara, Y. "Decomposition of Hydrocarbons in a Microwave Discharge", The Journal of Physical Chemistry, 73(6), 1969.

Kong, P. "Atmospheric-Pressure Plasma Process and Applications", SOHN International Symposium on Advanced Processing of Metals and Materials; Principles, Technologies and Industrial Practice, Sep. 2006.

Lang, T. "Quasi-equilibria of gaseous species in the C-H system", Diamond and Related Materials, 3, 1994, 470-475.

Malik, M. A. et al., "Catalyst Enhanced Oxidation of VOCs and Methane in Cold-Plasma Reactors", Platinum Metals Rev., 43(3), 1999, 109-113.

(56) References Cited

OTHER PUBLICATIONS

Marun, C. et al., "Catalytic Oligomerization of Methane via Microwave Heating", J. Phys. Chem. A, 103, 1999, 4332-4340.
McCarthy, R. L. et al., "Chemical Synthesis from Free Radicals Produced in Microwave Fields", J. Chem. Phys. 22(8), 1954, 1360-1365.
Minea, T. et al., "Methane activation in a microwave plasma reactor", 22nd International Symposium on Plasma Chemistry, Jul. 5-10, 2015; Antwerp, Belgium.
Mizeraczyk, J. et al., "Studies of atmospheric-pressure microwave plasmas used for gas processing", Nukleonika, 57(2), 2012, 241-247.
Moisan, M. et al., "An atmospheric pressure waveguide-fed microwave plasma torch the TIA design", Plasma Sources Sci. Technol., 3, 1994, 584-592.
Moisan, M. et al., "Large Diameter Plasma Generation Using a Waveguide-Based Field Applicator at 2.45 GHz", Journal of Microwave Power and Electromagnetic Energy, 30(1), 1995.
Mostaghimi, J. et al., "Thermal Plasma Sources: How Well are They Adopted to Process Needs?", Plasma Chem Plasma Process, 35, 2015, 421-436.
Onoe, K. et al., "Selective synthesis of acetylene from methane by microwave plasma reactions", Fuel, 76(3), 1997, 281-282.
Ravasio, S. et al., "Analysis of reactivity and energy efficiency of methane conversion through non thermal plasmas", Chemical Engineering Science, 84, 2012, 580-590.
Reuter, M. A. "Ulmann's Encyclopedia of Industrial Chemistry", VCH Verlaggesellshaft, A16, Retrieved from the Internet on Jan. 3, 2015, 1990, 375-387.
Scapinello, M. et al., "The panorama of plasma-assisted non-oxidative methane reforming", Chemical Engineering & Processing: Process Intensification, 117, 2017, 120-140.
Shen, C-S et al., "A study on methane coupling to acetylene under the microwave plasma", Science China Chemistry, 53(1), 2010, 231-237.
Snoeckx, R. et al., "Plasma-based liquefaction of methane The road from hydrogen production to direct methane liquefaction", Plasma Process. Polym, 9999, 2016, 1-10.
Spencer, L. F. "The Study of CO2 Conversion in a Microwave Plasma/Catalyst System", dissertation submitted in partial fulfillment of the requirements for the degree of Doctor of Philosophy (Applied Physics) in The University of Michigan, 2012.
Spitzl, R. "Energy Storage or (pre-)Product Synthesis by Microwave Plasma Conversion of Hydrocarbon containing Feedstocks", iplas Innovative Plasma Systems GmbH, www.cyrannus.com.
Suib, S. L. "A Direct, Continuous, Low-Power Catalytic Conversion of Methane to Higher Hydrocarbons via Microwave Plasmas", J. of Catalysis, 139, 1993, 383-391.
Szabo, D. et al., "Microwave Plasma Synthesis of Materials—From Physics and Chemistry to Nanoparticles: A Materials Scientist's Viewpoint", Inorganics, 2, 2014, 468-507.
Takeuchi, M. et al., "Chemical Reaction of Hydrocarbons in the Microwave Discharge I: On the Mechanism of the Decomposition of Ethane and Ethylene", Bulletin of the Institute for Chemical Research, Kyoto University, 49(4), 1971, 230-247.
Tsyganov, D. et al., "Conversion of Methane to C2 Hydrocarbons and Hydrogen Using Microwave 'tornado'-type Plasma", 42nd EPS Conference on Plasma Physics, University of Lisboa, Lisboa, Portugal.
Van Den Bekerom, D. et al., "Non-equilibrium Microwave Plasma for Efficient High Temperature Chemistry", J. Vis. Exp. (126), 2017, e55066.
Wang, B. et al., "Conversion of Methane to C2 Hydrocarbons via Cold Plasma Reaction", Journal of Natural Gas Chemistry, 12, 2003, 178-182.
Whitehead, J. C. et al., "Plasma—catalysis: the known knowns, the known unknowns and the unknown unknowns", J. Phys. D: Appl. Phys. 49, 2016.
Xu, Y. "Methane conversion via microwave plasma initiated by a metal initiator", in Studies in Surface Science and Catalysis 136, pp. 75-80. Natural Gas Conversion VI, Proceedings of the 6th Natural Gas Conversion Symposium, 2001, Alaska, USA, Elsevier Science B.V.
Yang, Y. "Direct Non-oxidative Methane Conversion by Non-thermal Plasma: Experimental Study", Plasma Chemistry and Plasma Processing, vol. 23, No. 2, Jun. 2003.
Yunpeng, X. et al., "Methane conversion via microwave plasma initiated by a metal initiator", Studies in Surface Science and Catalysis, 2001 Elsevier Science B.V.
Zhang, J-Q et al., "Non-Oxidative Coupling of Methane to C2 Hydrocarbons under Above-Atmospheric Pressure Using Pulsed Microwave Plasma", Energy & Fuels, 16, 2002, 687-693.
Zherlitsyn, A. G. et al., "Microwave plasma torch for processing hydrocarbon gases", Resource-Efficient Technologies, 2, 2016, 11-14.

\* cited by examiner

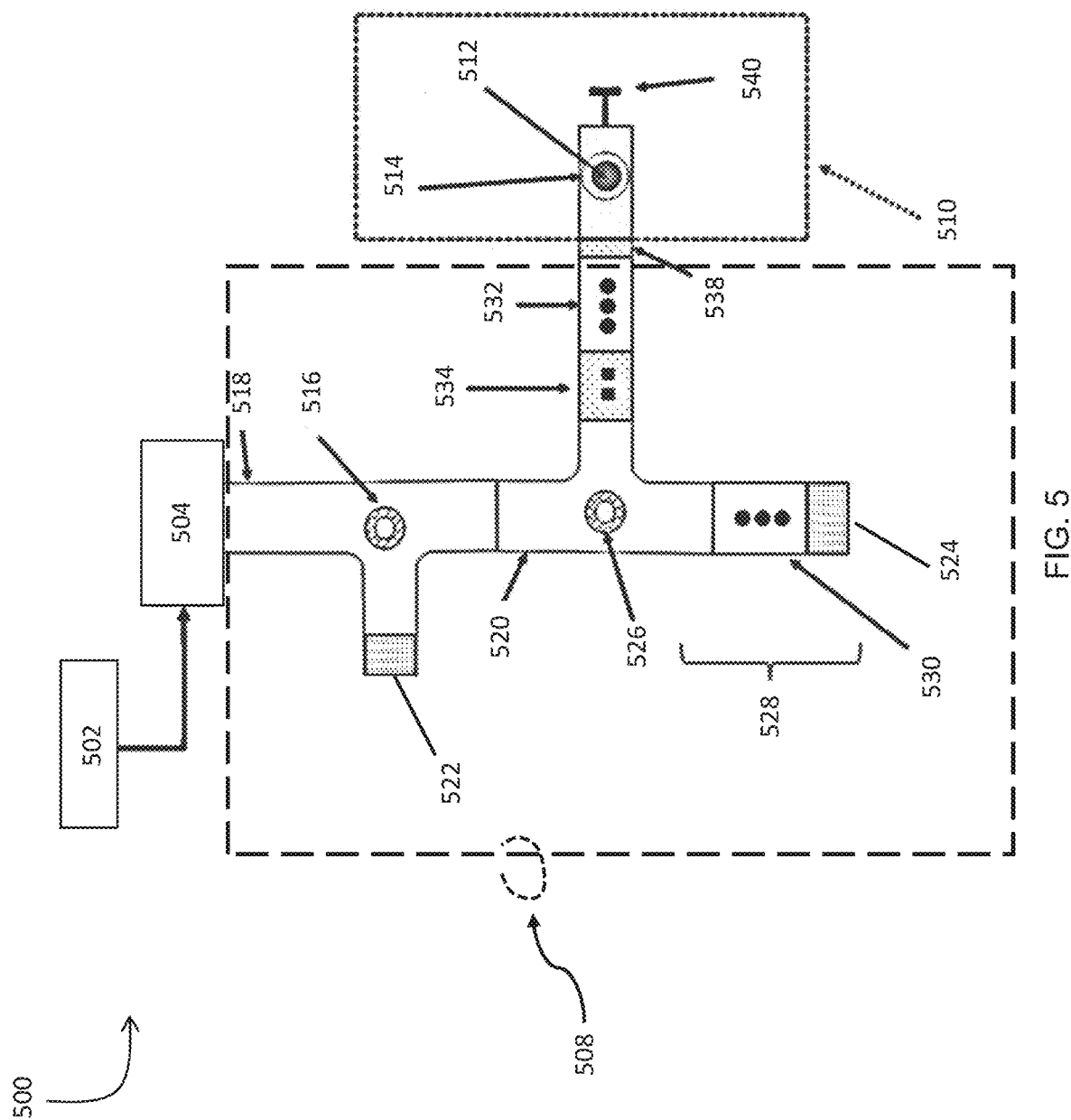

SYSTEMS AND METHODS FOR PROCESSING GASES

RELATED APPLICATIONS

This application is a continuation of U.S. application Ser. No. 17/155,760 filed on Jan. 22, 2021, which is a continuation-in-part of U.S. application Ser. No. 16/548,378 filed on Aug. 22, 2019, which claims the benefit of U.S. Provisional Application No. 62/721,863 filed on Aug. 23, 2018, U.S. Provisional Application No. 62/736,206 filed on Sep. 25, 2018, and U.S. Provisional Application No. 62/793,763 filed on Jan. 17, 2019; this application also claims the benefit of U.S. Provisional Application No. 62/964,977 filed Jan. 23, 2020, U.S. Provisional Application No. 62/969,494 filed Feb. 3, 2020, U.S. Provisional Application No. 62/986,998 filed Mar. 9, 2020, and U.S. Provisional Application No. 63/019,851 filed May 4, 2020, and U.S. Provisional Application No. 63/052,524, filed Jul. 16, 2020. The entire teachings of the above applications are incorporated herein by reference.

BACKGROUND

Acetylene can be used as a chemical precursor or as a feedstock for industrial combustion uses, such as welding and metal cutting. Commercial production of acetylene has been carried out since the early twentieth century. The original method for acetylene production utilized coal as the source material, through a process involving a calcium carbide intermediary. Other methods were developed later in the twentieth century, mainly using heat-based processes such as thermal cracking or electric arc furnaces.

Acetylene produced from coal involves a three-step process: first, coal is heated to produce high-carbon-content coke; second, the coke is heated further in the presence of calcium oxide to yield calcium carbide; third, calcium carbide reacts with water to yield acetylene and calcium hydroxide. The first two steps require very high temperatures, while the last step is exothermic. This method for forming acetylene is still used commercially, especially in China where coal is readily available.

This process, however, carries the impurities of the coal and lime source materials into the final product, so that the resulting acetylene is contaminated with impurities such as phosphines, arsines, and hydrogen sulfate. All of these species are capable of poisoning catalysts for subsequent chemical reactions, so that they need to be scrubbed from the acetylene product before it can be used commercially. Chemical grade acetylene, used for further chemical processing, must be >99.6% pure $C_2H_2$, with <25 ppm phosphine/arsine/$H_2S$. Industrial grade acetylene, which is burned for welding and metal cutting applications, can tolerate more impurities (>98.0 pure $C_2H_2$, <500 ppm phosphine/arsine/$H_2S$). Therefore, the coal-derived production of acetylene is limited in the U.S. to forming industrial grade acetylene; still, even when coal-derived acetylene is just used for welding and metal cutting, the presence of potentially hazardous contaminants raises concerns.

As an alternative, acetylene can be prepared from hydrocarbons by partial oxidation, for example, by the process developed by BASF, as described in U.S. Pat. No. 5,824,834. In this process, a hydrocarbon feedstock and oxygen are preheated and then reacted in a combustion chamber, causing the produced gases to reach temperatures >1500° C. The combustion reaction is quenched with water to effect rapid cooling, yielding a gaseous mixture (called "cleavage gas") of acetylene, hydrogen, carbon monoxide, steam, and byproducts. This method of acetylene production yields about 7.5% acetylene, along with large quantities of hydrogen (57%), carbon monoxide (26%), and methane (5.2%). One of the byproducts is soot, which needs to be removed from the cleavage gas as it is processed further. Other byproducts include higher-order hydrocarbons, including alkanes, alkenes, alkynes, and aromatics. Removing the impurities from the cleavage gas and recovering the acetylene it contains involve significant engineering challenges.

In addition to the production issues, acetylene is difficult to handle and transport. It is highly explosive. When transported through pipelines, it is kept at a low pressure and is only conveyed for short distances. Acetylene for industrial purposes is pumped into tanks at high pressure and dissolved in solvents, for example, dimethylformamide, N-methyl-2-pyrrolidone, or acetone. When the acetylene cylinder is opened, the dissolved gas vaporizes and flows through a connecting hose to the welding or cutting torch. The entire amount of acetylene in a cylinder is not usable however, because a certain amount remains dissolved in the solvent and is returned to the manufacturer in this state. With the rise of the petrochemical industry in the mid-twentieth century, acetylene continued to be used industrially (i.e., for welding, metal cutting and the like) but it was displaced as a precursor for chemical reactions, replaced by other feedstocks (e.g., ethylene) that were derived directly from oil rather than from coal. As oil has become more expensive and natural gas has become cheaper though, there is increased interest in acetylene as a platform for further chemical processing instead of petroleum-derived feedstocks.

Moreover, the abundance of natural gas is driving the search for more ways to use this material without burning it, to decrease its greenhouse gas effects and to avoid transforming it into $CO_2$, another greenhouse gas, by simple combustion. Besides natural gas, other mixed gas sources such as oceanic clathrates, coal mine gas, and biogas contain methane gas as well. Biogas is naturally produced mixed gas source that is produced by the anaerobic decomposition of organic waste material in various human-created environments such as landfills, manure holding ponds, waste facilities, and the like, and in natural environments such as peat bogs, melting permafrost, and the like. The anaerobic bacteria that occur in such environments digest the organic material that accumulates there to produce a gas mixture composed mainly of carbon dioxide and methane. Biogas with a high methane content, as can be found in landfill-derived gas mixtures, can be hazardous, because methane is potentially flammable. Moreover, methane is a potent greenhouse gas. Currently biogas that is collected from organic decomposition (e.g., landfills, waste facilities, holding ponds, and the like, or natural regions containing decaying organic materials) can be purified to remove the $CO_2$ and other trace gases, resulting in a high concentration of methane for producing energy. However, simply burning methane-rich biogas produces $CO_2$, another greenhouse gas. It would be desirable to identify uses for biogas or other mixed gas sources that can exploit their energy potential without burning them, to decrease the greenhouse gas effects of methane while avoiding transforming methane into another greenhouse gas, $CO_2$.

Increasing demand for non-hydrocarbon sources of fuel supports the use of methane as a feedstock for producing hydrogen, which in turn can be used as a source of power. Conventional technologies already exist for extracting hydrogen gas from the methane in natural gas. Steam reforming, for example, can produce hydrogen gas and carbon monoxide; the hydrogen created by the steam reforming process can then be used in pure form for other applications, such as hydrogen fuel cells or gas turbines, in which it combines with oxygen to form water, without greenhouse gas emissions. Other processes, such as partial oxidation, can produce a hydrogen-rich syngas, a combustible mixture that can be used as a fuel. Conventional techniques for producing hydrogen from methane have drawbacks, however. Steam reforming is carried out at high temperatures, and is energy-intensive, requiring costly materials that can withstand the harsh reaction conditions. Steam reforming uses catalysts to effect the conversion of methane to hydrogen, but the catalysts are vulnerable to poisoning by common contaminants. Partial oxidation is a less efficient technique than steam reforming for producing hydrogen, being prone to soot formation, and being limited in hydrogen yield. While over 90% of hydrogen is currently produced by thermochemical processes using hydrocarbon sources, it can also be produced by electrolysis of water and other non-carbon chemical processes.

Hydrogen, a zero-emission fuel source, can be used for a variety of commercial applications. The majority of hydrogen is used as a feedstock for industrial chemical processes, but it is gaining wider acceptance as a fuel source that can substitute for hydrocarbons. For example, hydrogen can power fuel cells or internal combustion, combining with oxygen in the atmosphere when it is burned. This use of hydrogen as a fuel thus avoids the production of carbon-based greenhouse gases such as carbon dioxide. Hydrogen is increasingly being used for powering vehicles such as trucks and passenger cars, and it is already an established fuel for mass transit vehicles like buses. More demand for hydrogen is expected with the emergence of the so-called "hydrogen economy," where hydrogen would be used as a fuel source for heat production, for vehicles, and for long-distance energy transportation.

There is a need in the art, therefore, for a process that utilizes mixed gas sources such as natural gas or biogas, and/or more purified hydrocarbon feedstocks (e.g., methane, ethane, propane, and butane, and combinations thereof) to form higher-value products. For those processes intended to produce acetylene, it would be advantageous to use mixed gas sources such as natural gas or biogas, and/or more purified hydrocarbon feedstocks (e.g., methane, ethane, propane, and butane) as a feedstock, avoiding the limitations of other mixed gas conversion processes or hydrocarbon combustion processes while taking advantage of the abundance of these feedstock materials.

Concomitantly, there is a need in the art for a process that can produce acetylene in a convenient and cost-effective way, using mixed gas sources such as natural gas or biogas, and/or more purified hydrocarbon feedstocks. It would be especially advantageous to produce acetylene with minimal impurities, so that it can be used safely and without substantial additional processing. Furthermore, there is further a need in the art to provide alternative fuels such as hydrogen scalably and efficiently. It would be desirable to carry out these processes in an economic and environmentally responsible way.

In addition, acetylene has utility as a fuel for various industrial applications, for example, metal cutting. This use represents a significant market, comparable in size to various petrochemical uses of acetylene. At present, a major industrial use of acetylene is as a fuel for oxyacetylene torches, used for cutting steel; in addition to cutting, acetylene is used in some welding, carburization, and heat-treating of steel. Oxyacetylene torches burn at a higher flame temperature (3,500° C.) than other oxy-fuel torches, such as oxy-hydrogen (3,000° C.) and oxy-propane (2,500° C.) torches, and oxyacetylene forms a smaller, more precise flame cone. These features allow for higher quality and more precise cutting than other comparable oxy-fuel cutting methods. Additionally, because the combustion of acetylene requires a smaller stoichiometric ratio of oxygen than other fuels like propane, the oxy-acetylene torches consume less oxygen than other oxy-fuel torches, leading to lower oxygen operational costs. Finally, the lower flame temperature and higher oxygen requirements of other hydrocarbon fuel types like oxy-propane torches allow for a higher risk of incomplete combustion, producing hazardous carbon monoxide in the work environment. For the aforesaid reasons, oxy-acetylene cutting is standard in the industry for steel cutting.

However, as described previously, there are limitations in the production of acetylene and its transportation. Therefore, sourcing acetylene for industrial cutting is expensive and logistically challenging. First of all, acetylene used as a fuel for torches must be transported and stored in small metal cylinders because of the risk of explosion. In order to reduce the risk of explosion, the acetylene in the cylinders is dissolved in acetone, lowering its partial pressure and thus the likelihood of explosion. Because acetone is present in the cylinders along with acetylene, the acetylene can only be drawn at low flow rates (for example, not to exceed $\frac{1}{7}$ of the container contents per hour), to reduce the chance of acetone being drawn into the outflow line along with the acetylene-acetone in the gas feed can diminish flame temperatures and the quality of the cutting process. Even with low rates of outflow, the acetylene in the cylinders can be depleted quickly; once depleted, a cylinder cannot be refilled on-site without extensive safety infrastructure and expertise, again because of the risk of explosion. Because of their small size, cylinders do not scale well for larger operations, but instead must be connected in parallel via manifolding, adding to a project's complexity. Also, because of the risk of explosion, cylinders require a number of safety precautions as they are transported, adding costs and logistical challenges.

There remains a need in the art for a more streamlined, safe method of sourcing acetylene. It would be desirable to circumvent the need for acetone-containing cylinders as the repository for acetylene gas that is used in metal working. For example, it would be useful to have acetylene fuel available on demand and as needed, avoiding the volume and flow rate constraints of cylinder storage. In addition, it would also be advantageous to have acetylene produced in proximity to the point of its use to avoid the cylinder-specific difficulties with transportation.

Acetylene is also useful as a precursor or substrate for various chemical reactions. One example is the manufacturing of polyvinyl chloride, which is produced from vinyl chloride monomer (VCM). Two industrial processes are currently employed to manufacture VCM: (i) the chlorination of ethylene to form ethylene dichloride followed by thermal cracking to yield VCM and HCl; and (ii) the direct hydrochlorination of acetylene. For this latter process, catalysts are used, for example, mercury chloride, activated carbon, ruthenium, and gold-based catalysts. This latter process, the direct hydrochlorination of acetylene, is particularly desirable in environments where there is a plentiful and reliable source of acetylene. However, production, storage, and transportation issues as described above affect the availability of acetylene to be used for VCM manufacture. It would be advantageous to provide acetylene in a convenient and cost-effective way so that it can be readily used as a precursor for VCM manufacture. It would be especially advantageous to provide a source of acetylene for VCM manufacture where the acetylene has minimal impurities, so that it can be used safely and without substantial additional processing. In addition, it would be advantageous to produce the acetylene for VCM manufacture scalably and efficiently without need for complex logistics. Desirably, the process for VCM manufacturing can be integrated with a process for producing acetylene so that the difficulties of acetylene transport and storage are avoided.

Another example using acetylene as a precursor for chemical reactions is the manufacture of vitamins A and E. While acetylene is useful as a feedstock for making these vitamins and the provitamin β-Carotene and their chemical intermediates, its industrial use entails challenges. As yet another example using acetylene as a precursor for chemical manufacture, acetylene can be decomposed to produce hydrogen gas and carbon solids. The particulate carbon produced by this reaction, termed acetylene black, is particularly useful because its small and uniform primary particles form long chains of carbon with excellent electrical and thermal conductivity. Because of its physical structure and purity, acetylene black is a more valuable substance than standard carbon black. It is used, for example, in the manufacture of batteries, conductive polymers, and other specialty products.

Importing acetylene to manufacturing sites as a precursor for chemical reactions such as those described above incurs high transportation costs due to its explosive nature; commercial grade acetylene can contain impurities; and the material itself can be in short supply. Moreover, current techniques for producing acetylene (using calcium carbide, partial oxidation, or cracking) all have process-specific drawbacks. It would be advantageous to produce acetylene for vitamin manufacturing or acetylene black production with minimal impurities, so that it can be used for these processes without substantial additional processing. In addition, it would be advantageous to produce acetylene on-site and scalably, without the need for complex logistics, providing a supply that is tailored to meet the manufacturer's demand. Desirably, the process for vitamin manufacturing or acetylene black manufacturing can be integrated with a process for producing acetylene so that the difficulties of acetylene transport and storage are avoided.

Hydrogen, like acetylene, has many uses in industrial chemistry. Its conventional production, however, involves technologies that require considerable energy input, including steam methane reforming and electrolysis. Moreover, steam methane reforming and similar industrial practices themselves produce carbon monoxide or carbon dioxide as part of their hydrogen-forming reactions, counteracting the net environmental gains that might flow from the use of hydrogen as a fuel instead of hydrocarbons. It would be desirable, therefore, to produce hydrogen for use as a zero-emissions fuel in a way that does not create additional greenhouse gases and that does not consume inordinate amounts of energy.

Furthermore, despite its environmental advantages, hydrogen faces significant logistical and distribution challenges that counteract its zero-carbon footprint. Conventional thermochemical technologies for producing hydrogen typically require large-scale industrial facilities, generally located at a distance from the ultimate user. Once it is generated, hydrogen must therefore be stored and/or be transported across long distances. Currently, the infrastructure for conveying hydrogen from the point of production to the point of use includes a mix of pipelines, tank trucks, tube trailers, and the like as transportation methods, all of which can add their own carbon burden to the atmosphere. In addition, hydrogen must be stored and transported as a super-cooled liquid or a highly compressed gas, with the potential for leakage and explosion, making the industrial use of hydrogen more challenging for the customer. It would be advantageous to produce hydrogen in a smaller-scale facility that can be installed closer to the end-user, decreasing the complexities of transporting this fuel over long distances. It would also be advantageous to provide for on-demand production of hydrogen, potentially obviating the need for complex logistics significantly.

SUMMARY OF THE INVENTION

Disclosed herein, in embodiments, are gas processing systems for transforming a hydrocarbon-containing inflow gas into outflow gas products, comprising a gas delivery subsystem, a plasma reaction chamber, and a microwave subsystem, wherein the gas delivery subsystem is in fluid communication with the plasma reaction chamber and directs the hydrocarbon-containing inflow gas into the plasma reaction chamber, wherein the microwave subsystem directs microwave energy into the plasma reaction chamber to energize the hydrocarbon-containing inflow gas thereby forming a plasma in the plasma reaction chamber, and wherein the plasma effects the transformation of a hydrocarbon in the hydrocarbon-containing inflow gas into the outflow gas products that comprise acetylene and hydrogen. In embodiments, the hydrocarbon-containing inflow gas can be derived from a mixed gas source, and the mixed gas source can be natural gas or a biogas; in embodiments, the hydrocarbon-containing inflow gas comprises a gas selected from the group consisting of methane, ethane, propane, and butane, and the hydrocarbon-containing inflow gas can consist essentially of methane. In embodiments, the gas delivery subsystem comprises a delivery conduit and a gas injector, wherein the delivery conduit is in fluid communication with the gas injector, wherein the delivery conduit delivers one or more gases to the gas injector, and wherein the gas injector delivers the one or more gases into the plasma reaction chamber. The delivery conduit can comprise a feed gas conveying circuit that delivers the hydrocarbon-containing inflow gas into the gas injector, and the hydrocarbon-containing inflow gas can comprise methane or can consist essentially of methane. In embodiments, the delivery conduit comprises an additional gas conveying circuit that delivers an additional gas into the gas injector, and the additional gas can be hydrogen. In embodiments, the additional gas conveying circuit is an auxiliary gas conveying circuit that delivers an auxiliary gas into the gas injector, or the additional gas conveying circuit is a recycled gas conveying circuit that delivers a recycled gas into the gas injector. The recycled gas can comprise hydrogen, or it can comprise a hydrogen rich reactant gas, or it can consist essentially of hydrogen, or it can consist essentially of a hydrogen rich reactant gas. In embodiments, the delivery conduit delivers each of the one or more gases into the gas injector through a separate pathway. In embodiments, the gas injector comprises an injector body comprising two or more coaxially arranged and separate gas feeds, a first gas feed conveying the hydrocarbon-containing inflow gas into the plasma reaction chamber through a first set of one or more nozzles, and the second gas feed conveying the additional gas into the plasma reaction chamber through a second set of one or more nozzles. In embodiments, at least one of the one or more nozzles is oriented at an angle to a longitudinal axis of the plasma reaction chamber or at an angle to a transverse axis of the plasma reaction chamber. In embodiments, at least one of the one or more nozzles is oriented at an angle to a longitudinal axis or a transverse axis of the injector body. The combined gas flow from the first set of nozzles and the second set of nozzles creates a vortex flow within the plasma reaction chamber. In embodiments, the plasma reaction chamber is disposed within an elongate reactor tube having a proximal and a distal end, and the elongate reactor tube is dimensionally adapted for interaction with the microwave subsystem. The elongate reactor tube can be a quartz tube. The plasma reactor chamber can be disposed approximately at the midportion of the elongate reactor tube. In embodiments, the gas injector conveys the hydrocarbon-containing inflow gas and the additional gas into a proximal portion of the elongate reactor tube wherein the hydrocarbon-containing inflow gas and the additional gas flow distally therefrom towards the plasma reaction chamber. The gas injector can be positioned centrally within the proximal portion, and the first set of one or more nozzles and the second set of one or more nozzles are oriented peripherally; alternatively, the gas injector is positioned peripherally within the proximal portion, and the first set of one or more nozzles and the second set of one or more nozzles are oriented centrally. In embodiments, the microwave subsystem comprises an applicator for directing microwave energy towards the plasma reaction chamber, and the plasma reaction chamber is disposed in a region of the elongate reactor tube that passes through the applicator and intersects it perpendicularly. The applicator can be a single-arm applicator. In embodiments, the microwave subsystem further comprises a power supply, a magnetron, and a waveguide, whereby the power supply energizes the magnetron to produce microwave energy with the microwave energy being conveyed by the waveguide to the applicator, and wherein the applicator directs the microwave energy towards the reaction chamber within the elongate reactor tube, thereby forming the plasma in the plasma reaction chamber. The magnetron can produce L-band microwave energy. In embodiments, the plasma within the plasma reaction chamber produces the outflow gas products, and the outflow gas products flow within the plasma reaction chamber distally towards the distal end of the elongate reactor tube. The outflow products can emerge from the distal end of the elongate reactor tube to enter an effluent separation and disposal subsystem. In embodiments, the effluent separation and disposal subsystem can comprise a solids filter and a cold trap, and/or can comprise an adsorption column, and/or can comprise a pressure swing adsorption system adapted for removing non-hydrogen components from an effluent stream, and/or can comprise a temperature swing adsorption system adapted for removing higher acetylenes from an effluent stream, which temperature swing adsorption system can include a regular-cycle temperature swing adsorber.

In certain embodiments, the invention is directed to system for transforming a hydrocarbon-containing inflow gas into outflow gas products, comprising:
- a gas delivery subsystem, a plasma reaction chamber, a microwave subsystem, and an effluent separation and disposal system;
- wherein the gas delivery subsystem:
  i. is in fluid communication with the plasma reaction chamber and directs one or more gases into the plasma reaction chamber, wherein the one or more gases comprises the hydrocarbon-containing inflow gas; and
  ii. comprises a delivery conduit and a gas injector,
     a. wherein the delivery conduit is in fluid communication with the gas injector, wherein the delivery conduit delivers the one or more gases to the gas injector, and wherein the delivery conduit comprises a feed gas conveying circuit that delivers the hydrocarbon-containing inflow gas into the gas injector, and
     b. wherein the gas injector delivers the one or more gases into the plasma reaction chamber;
- wherein the plasma reaction chamber:
  i. is in fluid communication with the effluent separation and disposal system; and
  ii. is disposed within an elongate reactor tube having a proximal and a distal end, and wherein the elongate reactor tube is dimensionally adapted for interaction with the microwave subsystem;
- wherein the microwave subsystem:
  i. directs microwave energy into the plasma reaction chamber to energize the hydrocarbon-containing inflow gas, thereby forming a plasma in the plasma reaction chamber, and wherein the plasma effects the transformation of a hydrocarbon in the hydrocarbon-containing inflow gas into the outflow gas products, wherein the outflow gas products comprise acetylene and hydrogen;
  ii. comprises an applicator for directing microwave energy towards the plasma reaction chamber, and wherein the plasma reaction chamber is disposed in the region of the elongate reactor tube that passes through the applicator and intersects it perpendicularly; and
  iii. further comprises a power supply, a magnetron, and a waveguide, whereby the power supply energizes the magnetron to produce microwave energy, the microwave energy being conveyed by the waveguide to the applicator, and wherein the applicator directs the microwave energy towards the reaction chamber within the elongate reactor tube, thereby forming the plasma in the plasma reaction chamber,
- wherein the outflow gas products flow within the plasma reaction chamber towards the distal end of the elongate reactor tube and emerge from the distal end of the elongate reactor tube forming an effluent stream that enters the effluent separation and disposal subsystem, and
- wherein the effluent separation and disposal system comprises a short-cycle temperature swing adsorption system adapted for separating the hydrogen from the effluent stream.

In embodiments, the effluent separation and disposal system comprises a temperature swing adsorption system adapted for separating hydrogen from the effluent stream, which temperature swing adsorption system can include a short-cycle temperature swing adsorber. In other embodiments, the effluent separation and disposal system comprises a regular-cycle temperature swing adsorption system adapted for separating higher acetylenes from the effluent stream and a short-cycle temperature swing adsorption system adapted for separating hydrogen from the effluent stream. In embodiments, the regular-cycle temperature swing adsorption system is positioned upstream from the short-cycle temperature swing adsorption system.

In addition or alternatively, the effluent separation and disposal subsystem can, in embodiments, comprise an absorption column which in embodiments can absorb acetylene, and/or can comprise a concentrated acid in an amount sufficient to oxidize higher-order hydrocarbons, and/or can comprise a catalyst suitable for converting higher-order hydrocarbons into derivative compounds separable from the effluent stream, and/or can comprise a condenser, and/or can comprise a gas separation membrane array which in embodiments can separate hydrogen from the effluent stream, and/or can comprise a hydrogen separation subsystem which in embodiments can be in fluid communication with the recycled gas conveying circuit wherein hydrogen collected by the hydrogen separation subsystem is recycled into the recycled gas conveying circuit, and/or can comprise an acetylene separation subsystem.

Further disclosed herein are methods for processing a hydrocarbon-containing inflow gas to produce acetylene gas, comprising providing the hydrocarbon-containing inflow gas, injecting the hydrocarbon-containing inflow gas into a reaction chamber, energizing the hydrocarbon-containing inflow gas in the reaction chamber with microwave energy to create a plasma; forming gas products in the plasma, wherein one of the gas products is the acetylene gas; and flowing the gas products to exit the reaction chamber. In yet additional embodiments, the invention encompasses a method for processing a hydrocarbon-containing inflow gas to produce outflow gas products, wherein the outflow gas products comprise acetylene and hydrogen, wherein the method comprises the steps of injecting the hydrocarbon-containing inflow gas into a plasma reaction chamber; energizing the hydrocarbon-containing inflow gas in the plasma reaction chamber with microwave energy to create a plasma; forming outflow gas products in the plasma, wherein the outflow gas products comprise acetylene and hydrogen; flowing the outflow gas products to exit the plasma reaction chamber; and removing hydrogen from the outflow gas products by short cycle temperature swing adsorption. In embodiments, the hydrocarbon-containing inflow gas is derived from a mixed gas source; the mixed gas source can be natural gas or a biogas. In embodiments, the hydrocarbon-containing inflow gas comprises a gas selected from the group consisting of methane, ethane, propane, and butane, and it can consist essentially of methane. In certain practices, the method further comprises the step of providing one or more additional gases concomitant with the step of providing the hydrocarbon-containing inflow gas, and the one or more additional gases can be selected from the group consisting of hydrogen, nitrogen, and a recycled gas. In embodiments, the recycled gas comprises a hydrogen-rich reactant gas, which can consist essentially of hydrogen. In certain practices, the method further comprises the step of segregating acetylene gas from the outflow gas products following the step of flowing the gas products to exit the reaction chamber. In yet further aspects, the method further comprises the step of segregating acetylene gas from the outflow gas products following the step of removing hydrogen from the outflow gas products by short cycle temperature swing adsorption. In certain practices, the method further comprises the step of recycling at least one of the gas products. In embodiments, the at least one gas product can comprise hydrogen gas, or can consist essentially of hydrogen gas.

Also disclosed herein are methods for transforming a hydrocarbon-containing inflow gas into an outflow gas, comprising providing the hydrocarbon-containing inflow gas, directing the hydrocarbon-containing inflow gas into the gas processing system as described above, and processing the hydrocarbon-containing inflow gas using the gas processing system described above to transform the inflow gas into the outflow gas, wherein the outflow gas comprises acetylene. In embodiments, the hydrocarbon-containing inflow gas is derived from a mixed gas source, and the mixed gas source can be natural gas or a biogas. In embodiments, the outflow gas further comprises hydrogen. In addition, the invention encompasses a method for transforming a hydrocarbon-containing inflow gas into outflow gas products, comprising: providing one or more gases, wherein the one or more gases comprises the hydrocarbon-containing inflow gas; directing the hydrocarbon-containing inflow gas into the system described herein, wherein the delivery conduit delivers the one or more gases to the gas injector, wherein the gas injector delivers the one or more gases into the plasma reaction chamber; wherein the microwave subsystem directs microwave energy into the plasma reaction chamber to transform the one or more gases into the plasma and wherein the plasma effects the transformation of a hydrocarbon in the hydrocarbon-containing inflow gas into the outflow gas products; wherein the outflow gas products flow within the plasma reaction chamber towards the distal end of the elongate reactor tube and emerge from the distal end of the elongate reactor tube forming an effluent stream that enters the effluent separation and disposal subsystem; and wherein the short-cycle temperature swing adsorption system removes hydrogen from the effluent stream.

Disclosed herein, in addition, are metal-cutting systems, comprising the gas processing system as described herein, and a storage system for containing the outflow gas products produced by the system; and an apparatus for metal-cutting in fluid communication with the storage system, wherein the apparatus draws the outflow gas products from the storage system and ignites them for use in metal cutting. In embodiments, the apparatus is an acetylene torch or an oxyacetylene torch. In embodiments, the metal-cutting system further comprises a hydrogen separation system in fluid communication with the gas processing system as described above, wherein the outflow gas flows into the hydrogen separation system, wherein the hydrogen separation system separates the outflow gas into two product streams, wherein one product stream is an acetylene-rich gas; and wherein the apparatus for metal cutting uses the acetylene-rich gas stored in the storage system as fuel for metal cutting.

Also disclosed are gas processing systems and methods for transforming a hydrocarbon-containing inflow gas into a vinyl chloride monomer (VCM). The invention encompasses a system for transforming a hydrocarbon-containing inflow gas into a VCM (vinyl chloride monomer)-containing liquid product, comprising:
  a gas delivery subsystem, a plasma reaction chamber, a microwave subsystem, and a VCM reactor and separator subsystem;
  wherein the gas delivery subsystem:
    i. is in fluid communication with the plasma reaction chamber and directs one or more gases into the plasma reaction chamber, wherein the one or more gases comprises the hydrocarbon-containing inflow gas; and
    ii. comprises a delivery conduit and a gas injector,
      a. wherein the delivery conduit is in fluid communication with the gas injector, wherein the delivery conduit delivers the one or more gases to the gas injector, and wherein the delivery conduit comprises a feed gas conveying circuit that delivers the hydrocarbon-containing inflow gas into the gas injector, and
      b. wherein the gas injector delivers the one or more gases into the plasma reaction chamber;
  wherein the plasma reaction chamber:
    i. is in fluid communication with the effluent separation and disposal system; and ii. is disposed within an elongate reactor tube having a proximal and a distal end, and wherein the elongate reactor tube is dimensionally adapted for interaction with the microwave subsystem;

wherein the microwave subsystem:

i. directs microwave energy into the plasma reaction chamber to energize the hydrocarbon-containing inflow gas, thereby forming a plasma in the plasma reaction chamber, and wherein the plasma effects the transformation of a hydrocarbon in the hydrocarbon-containing inflow gas into outflow gas products, wherein the outflow gas products comprise acetylene and hydrogen;

ii. comprises an applicator for directing microwave energy towards the plasma reaction chamber, and wherein the plasma reaction chamber is disposed in the region of the elongate reactor tube that passes through the applicator and intersects it perpendicularly; and iii. further comprises a power supply, a magnetron, and a waveguide, whereby the power supply energizes the magnetron to produce microwave energy, the microwave energy being conveyed by the waveguide to the applicator, and wherein the applicator directs the microwave energy towards the reaction chamber within the elongate reactor tube, thereby forming the plasma in the plasma reaction chamber, wherein the outflow gas products flow within the plasma reaction chamber towards the distal end of the elongate reactor tube and emerge from the distal end of the elongate reactor tube forming an outflow stream that enters the VCM reactor and separator subsystem, wherein the VCM reactor and separator subsystem comprises a VCM reactor and a plurality of separators;

i. wherein the plurality of separators comprise a first separation system, a second separation system and a third separation system;

ii. wherein the first separation system is in fluid communication with the elongate reactor tube, and is an effluent separator adapted to remove higher acetylenes and aromatics from the outflow stream, producing a purified effluent stream to deliver to the VCM reactor, wherein the purified effluent stream comprises acetylene gas; and wherein:

(a) the VCM reactor is in fluid communication with the first separation system and the second separation system;

(b) the VCM reactor receives the purified effluent stream and directs the purified effluent stream across a catalytic bed that reacts the acetylene gas with a stream of hydrogen chloride gas to produce VCM; and (c) the VCM reactor expels the VCM formed therein in a gaseous VCM-containing effluent stream that is directed into the second separation system;

iii. wherein the second separation system is a condensing system comprising a compressor, a chiller, and a liquid-gas separator, the second separation system being adapted to condense VCM into liquid VCM and separate liquid VCM from the VCM effluent stream, yielding the VCM-containing liquid product and a residual gas stream; and iv. wherein the residual gas stream is directed into a third separation system in fluid communication with the second separation system, wherein the third separation system processes the residual gas stream to separate purified hydrogen from the residual gas.

The invention also includes a system for transforming a hydrocarbon-containing inflow gas into a VCM (vinyl chloride monomer)-containing liquid product, comprising:

a gas delivery subsystem, a plasma reaction chamber, a microwave subsystem, and a VCM reactor and separator subsystem;

wherein the gas delivery subsystem:

i. is in fluid communication with the plasma reaction chamber and directs one or more gases into the plasma reaction chamber, wherein the one or more gases comprises the hydrocarbon-containing inflow gas; and ii. comprises a delivery conduit and a gas injector;

a. wherein the delivery conduit is in fluid communication with the gas injector, wherein the delivery conduit delivers the one or more gases to the gas injector, and wherein the delivery conduit comprises a feed gas conveying circuit that delivers the hydrocarbon-containing inflow gas into the gas injector, and b. wherein the gas injector delivers the one or more gases into the plasma reaction chamber;

wherein the plasma reaction chamber:

i. is in fluid communication with the effluent separation and disposal system; and ii. is disposed within an elongate reactor tube having a proximal and a distal end, and wherein the elongate reactor tube is dimensionally adapted for interaction with the microwave subsystem;

wherein the microwave subsystem:

i. directs microwave energy into the plasma reaction chamber to energize the hydrocarbon-containing inflow gas, thereby forming a plasma in the plasma reaction chamber, and wherein the plasma effects the transformation of a hydrocarbon in the hydrocarbon-containing inflow gas into outflow gas products, wherein the outflow gas products comprise acetylene and hydrogen;

ii. comprises an applicator for directing microwave energy towards the plasma reaction chamber, and wherein the plasma reaction chamber is disposed in the region of the elongate reactor tube that passes through the applicator and intersects it perpendicularly; and further comprises a power supply, a magnetron, and a waveguide, whereby the power supply energizes the magnetron to produce microwave energy, the microwave energy being conveyed by the waveguide to the applicator, and wherein the applicator directs the microwave energy towards the reaction chamber within the elongate reactor tube, thereby forming the plasma in the plasma reaction chamber, wherein the outflow gas products flow within the plasma reaction chamber towards the distal end of the elongate reactor tube and emerge from the distal end of the elongate reactor tube forming an outflow stream that enters the VCM reactor and separator subsystem, wherein the VCM reactor and separator subsystem comprises a VCM reactor and a plurality of separators;

i. wherein the plurality of separators comprises a first separation system, a second separation system and a third separation system;

ii. wherein the first separation system, in fluid communication with the elongate reactor tube, is an effluent separator adapted to remove higher acetylenes and aromatics from the outflow stream, producing a purified effluent stream comprising acetylene gas and hydrogen;

iii. wherein the purified effluent stream enters the second separation system in fluid communication with the first separation system;
iv. wherein the hydrogen is separated from the purified effluent stream, thereby producing a separate hydrogen stream and a concentrated effluent stream comprising acetylene gas;
v. wherein the concentrated effluent stream is delivered to the VCM reactor in fluid communication with the second separation system; wherein:
   (a) the VCM reactor receives the concentrated effluent stream and directs the concentrated effluent stream across a catalytic bed that reacts the acetylene gas with a stream of hydrogen chloride gas to produce VCM; and
   (b) the VCM reactor expels the VCM formed therein in a gaseous VCM-containing effluent stream that is directed into the third separation system;
vi. wherein the third separation system, in fluid communication with the VCM reactor, is a condensing system comprising a compressor, a chiller, and a liquid-gas separator, the third separation system being adapted to condense liquid VCM and separate it from the VCM effluent stream, yielding the liquid VCM product and a residual gas stream.

Also described are methods of using the systems described herein to produce a vinyl chloride monomer. In certain embodiments, the invention is directed to a method for producing a vinyl chloride monomer, comprising providing a system described herein; processing a hydrocarbon-containing inflow gas to produce outflow gas products, wherein the outflow gas products comprise acetylene and hydrogen, wherein the step of processing comprises the steps of: injecting the hydrocarbon-containing inflow gas into the plasma reaction chamber; energizing the hydrocarbon-containing inflow gas in the plasma reaction chamber with microwave energy to create a plasma; forming outflow gas products in the plasma, wherein the outflow gas products comprise acetylene and hydrogen; flowing the outflow gas products to exit the plasma reaction chamber; and processing the acetylene thereby produced in the VCM reactor and separator subsystem in fluid communication with the plasma reaction chamber, wherein the VCM reactor combines the acetylene with hydrogen chloride gas to form VCM in the gas by a catalytic reaction within the VCM reactor, and wherein the catalytic reaction proceeds by exposing the acetylene and hydrogen chloride gas to a catalyst within the VCM reactor.

The invention also includes a method for transforming a hydrocarbon-containing inflow gas into a VCM (vinyl chloride monomer)-containing liquid product, comprising providing one or more gases, wherein the one or more gases comprises the hydrocarbon-containing inflow gas; directing the one or more gases into the system described herein, wherein the delivery conduit delivers the one or more gases to the gas injector, wherein the gas injector delivers the one or more gases into the plasma reaction chamber, wherein the microwave subsystem directs microwave energy into the plasma reaction chamber to transform the one or more gases into a plasma and wherein the plasma effects the transformation of a hydrocarbon in the hydrocarbon-containing inflow gas into the outflow gas products; wherein the outflow gas products flow within the plasma reaction chamber towards the distal end of the elongate reactor tube and emerge from the distal end of the elongate reactor tube forming an effluent stream that enters the VCM reactor and separator subsystem; wherein the outflow gas products comprise acetylene and hydrogen; and wherein the VCM reactor and separator subsystem is in fluid communication with the elongate reactor tube; combining acetylene with hydrogen chloride in the VCM reactor to form a VCM-containing gas; and separating the VCM from the VCM-containing gas as a VCM-containing liquid product.

In yet additional aspects, the invention includes a method for processing a hydrocarbon-containing inflow gas into a VCM (vinyl chloride monomer)-containing liquid product, the method comprising the steps of: injecting the hydrocarbon-containing inflow gas into a plasma reaction chamber; energizing the hydrocarbon-containing inflow gas in the plasma reaction chamber with microwave energy to create a plasma; forming outflow gas products in the plasma, wherein the outflow gas products comprise acetylene and hydrogen; flowing the outflow gas products to exit the plasma reaction chamber and enter a VCM and separator subsystem, wherein the VCM and separator subsystem is in fluid communication with the plasma reaction chamber, wherein the VCM and separator subsystem comprises a VCM reactor, and wherein the outflow gas products comprise acetylene and hydrogen; combining acetylene with hydrogen chloride in the VCM reactor to form a VCM-containing gas; and separating the VCM from the VCM-containing gas as a VCM-containing liquid product.

The invention also encompasses an integrated acetylene-based vitamin synthesis system for synthesizing a vitamin product (including but not limited to Vitamin A, Vitamin E, b-carotene, or a combination thereof) comprising:
a plasma-based hydrocarbon processing system and a vitamin manufacturing system,
wherein the plasma-based hydrocarbon processing system comprises a gas delivery subsystem, a plasma reaction chamber, a microwave subsystem, and a set of separator subsystems,
wherein the gas delivery subsystem:
i. is in fluid communication with the plasma reaction chamber and directs one or more gases into the plasma reaction chamber, wherein the one or more gases comprises the hydrocarbon-containing inflow gas; and
ii. comprises a delivery conduit and a gas injector,
   a. wherein the delivery conduit is in fluid communication with the gas injector, wherein the delivery conduit delivers the one or more gases to the gas injector, and wherein the delivery conduit comprises a feed gas conveying circuit that delivers the hydrocarbon-containing inflow gas into the gas injector, and
   b. wherein the gas injector delivers the one or more gases into the plasma reaction chamber;
wherein the plasma reaction chamber:
i. is in fluid communication with the effluent separation and disposal system; and
ii. is disposed within an elongate reactor tube having a proximal and a distal end, and wherein the elongate reactor tube is dimensionally adapted for interaction with the microwave subsystem;
wherein the microwave subsystem:
i. directs microwave energy into the plasma reaction chamber to energize the hydrocarbon-containing inflow gas, thereby forming a plasma in the plasma reaction chamber, and wherein the plasma effects the transformation of a hydrocarbon in the hydrocarbon-containing inflow gas into outflow gas products, wherein the outflow gas products comprise acetylene and hydrogen;
ii. comprises an applicator for directing microwave energy towards the plasma reaction chamber, and wherein the plasma reaction chamber is disposed in the region of the elongate reactor tube that passes through the applicator and intersects it perpendicularly; and iii. further comprises a power supply, a magnetron, and a waveguide, whereby the power supply energizes the magnetron to produce microwave energy, the microwave energy being conveyed by the waveguide to the applicator, and wherein the applicator directs the microwave energy towards the reaction chamber within the elongate reactor tube, thereby forming the plasma in the plasma reaction chamber, wherein the outflow gas products flow within the plasma reaction chamber towards the distal end of the elongate reactor tube and emerge from the distal end of the elongate reactor tube forming an outflow stream that enters the set of separator subsystems;

i. wherein the set of separator subsystems comprises an effluent separator, an acetylene separator, and a hydrogen separator;

ii. wherein the effluent separator is in fluid communication with the elongate reactor tube, and is adapted to remove higher acetylenes and aromatics from the outflow stream, producing a purified effluent stream comprising acetylene gas and hydrogen;

iii. wherein the acetylene separator is in fluid communication with the effluent separator, and separates a purified acetylene product from the purified effluent stream, thereby forming a remaining effluent stream, and wherein the acetylene separator is in fluid communication with the vitamin manufacturing system and directs at least a portion of the purified acetylene product into the vitamin manufacturing system; and iv. wherein acetylene separator is further in fluid communication with the hydrogen separator and directs the remaining effluent stream into the hydrogen separator, wherein the hydrogen separator separates hydrogen from the remaining effluent stream, producing a purified hydrogen product;

v. wherein the hydrogen separator is also in fluid communication with the vitamin manufacturing system and directs at least a portion of the purified hydrogen product into the vitamin manufacturing system; and wherein the vitamin manufacturing system comprises a vitamin reaction plant and a controller, whereby the controller regulates entry of the portion of purified acetylene product and the portion of purified hydrogen product into the vitamin reaction plant, and wherein the vitamin reaction plant synthesizes the vitamin product using the purified acetylene product and/or the purified hydrogen product.

The invention also includes a method for synthesizing a vitamin product, comprising use of the integrated acetylene-based vitamin synthesis system for synthesizing a vitamin product. In certain embodiments, the inventive method comprises:

i. processing a hydrocarbon-containing inflow gas to produce outflow gas products using the system described herein, wherein the outflow gas products comprise acetylene and hydrogen, wherein the step of processing comprises the steps of:

a. injecting the hydrocarbon-containing inflow gas into the plasma reaction chamber;

b. energizing the hydrocarbon-containing inflow gas in the plasma reaction chamber with microwave energy to create a plasma;

c. forming outflow gas products in the plasma, wherein the outflow gas products comprise acetylene and hydrogen;

d. flowing the outflow gas products to exit the plasma reaction chamber;

ii. separating the outflow gas products into a set of gas streams, the set of gas streams comprising a first gas stream comprising higher acetylenes and aromatic impurities, a second gas stream comprising purified acetylene, and a third gas stream comprising purified hydrogen;

iii. directing the second gas stream comprising purified acetylene into the vitamin manufacturing system; and iv. synthesizing the vitamin product from the purified acetylene.

The invention also encompasses an integrated acetylene-based synthesis system for synthesizing acetylene black, comprising:

a plasma-based hydrocarbon processing system and an acetylene-black manufacturing system, wherein the plasma-based hydrocarbon processing system comprises a gas delivery subsystem, a plasma reaction chamber, a microwave subsystem, and a set of separation and purification subsystems, wherein the gas delivery subsystem:

i. is in fluid communication with the plasma reaction chamber and directs one or more gases into the plasma reaction chamber, wherein the one or more gases comprises the hydrocarbon-containing inflow gas; and ii. comprises a delivery conduit and a gas injector, wherein the delivery conduit is in fluid communication with the gas injector, wherein the delivery conduit delivers the one or more gases to the gas injector, and wherein the delivery conduit comprises a feed gas conveying circuit that delivers the hydrocarbon-containing inflow gas into the gas injector, and wherein the gas injector delivers the one or more gases into the plasma reaction chamber;

wherein the plasma reaction chamber:

i. is in fluid communication with the effluent separation and disposal system; and ii. is disposed within an elongate reactor tube having a proximal and a distal end, and wherein the elongate reactor tube is dimensionally adapted for interaction with the microwave subsystem;

wherein the microwave subsystem:

i. directs microwave energy into the plasma reaction chamber to energize the hydrocarbon-containing inflow gas, thereby forming a plasma in the plasma reaction chamber, and wherein the plasma effects the transformation of a hydrocarbon in the hydrocarbon-containing inflow gas into outflow gas products, wherein the outflow gas products comprise acetylene and hydrogen;

ii. comprises an applicator for directing microwave energy towards the plasma reaction chamber, and wherein the plasma reaction chamber is disposed in the region of the elongate reactor tube that passes through the applicator and intersects it perpendicularly; and iii. further comprises a power supply, a magnetron, and a waveguide, whereby the power supply energizes the magnetron to produce microwave energy, the microwave energy being conveyed by the waveguide to the applicator, and wherein the applicator directs the microwave energy towards the reaction chamber within the elongate reactor tube, thereby forming the plasma in the plasma reaction chamber, wherein the outflow gas products flow within the plasma reaction chamber towards the distal end of the elongate reactor tube and emerge from the distal end of the elongate reactor tube forming an outflow stream that enters the set of separation and purification subsystems;

i. wherein the set of separation and purification subsystems comprises an acetylene separator in fluid communication with the elongate reactor tube, adapted to remove higher acetylenes and aromatics from the outflow stream, producing a purified effluent stream comprising acetylene gas and hydrogen and an offgas stream comprising higher acetylenes and aromatics;

ii. wherein the set of separation and purification subsystems further comprises a hydrogen separator in fluid communication with the elongate reactor tube, wherein the hydrogen separator separates hydrogen as a hydrogen stream from at least one of the outflow stream and the purified effluent stream; and iii. wherein the set of separation and purification subsystems produces an acetylene-rich feedstock stream; and an acetylene-black manufacturing subsystem, wherein the acetylene-black manufacturing system comprises an acetylene decomposition reactor in fluid communication with the separation and purification subsystems, and wherein the acetylene decomposition reactor produces acetylene black and hydrogen from the acetylene-rich feedstock stream produced by the separation and purification subsystems.

The invention also includes a method for synthesizing acetylene black comprising use of the integrated acetylene-based system as described herein. In certain embodiments, the inventive method comprises:

i. providing the integrated acetylene-based system as described herein, ii. processing a hydrocarbon-containing inflow gas to produce outflow gas products using the integrated acetylene-based system, wherein the outflow gas products comprise acetylene and hydrogen, wherein the step of processing comprises the steps of:
  a. injecting the hydrocarbon-containing inflow gas into the plasma reaction chamber;
  b. energizing the hydrocarbon-containing inflow gas in the plasma reaction chamber with microwave energy to create a plasma;
  c. forming outflow gas products in the plasma, wherein the outflow gas products comprise acetylene and hydrogen;
  d. flowing the outflow gas products to exit the plasma reaction chamber;

iii. separating the outflow gas products into a set of gas streams, the set of gas streams comprising a first gas stream comprising higher acetylenes and aromatic impurities, a second gas stream comprising purified acetylene, and a third gas stream comprising purified hydrogen;

iv. directing the second gas stream comprising purified acetylene into the acetylene-black manufacturing system; and v. synthesizing the acetylene black from the purified acetylene.

The invention additionally includes an integrated acetylene-based synthesis system for producing hydrogen, the system comprising a plasma-based hydrocarbon processing subsystem and an acetylene-black manufacturing subsystem:

a. wherein the plasma-based hydrocarbon processing subsystem comprises a gas delivery subsystem, a plasma reaction chamber, a microwave subsystem, and a set of separation and purification subsystems, wherein the gas delivery subsystem:
  i. is in fluid communication with the plasma reaction chamber and directs one or more gases into the plasma reaction chamber, wherein the one or more gases comprises the hydrocarbon-containing inflow gas; and
  ii. comprises a delivery conduit and a gas injector,
  wherein the delivery conduit is in fluid communication with the gas injector,
  wherein the delivery conduit delivers the one or more gases to the gas injector, and
  wherein the delivery conduit comprises a feed gas conveying circuit that delivers the hydrocarbon-containing inflow gas into the gas injector, and
  wherein the gas injector delivers the one or more gases into the plasma reaction chamber;

wherein the plasma reaction chamber:
  i. is in fluid communication with the set of separation and purification subsystems; and
  ii. is disposed within an elongate reactor tube having a proximal and a distal end, and wherein the elongate reactor tube is dimensionally adapted for interaction with the microwave subsystem;

wherein the microwave subsystem:
  i. directs microwave energy into the plasma reaction chamber to energize the hydrocarbon-containing inflow gas, thereby forming a plasma in the plasma reaction chamber, and wherein the plasma effects the transformation of a hydrocarbon in the hydrocarbon-containing inflow gas into outflow gas products, wherein the outflow gas products comprise acetylene and hydrogen;
  ii. comprises an applicator for directing microwave energy towards the plasma reaction chamber, and wherein the plasma reaction chamber is disposed in the region of the elongate reactor tube that passes through the applicator and intersects it perpendicularly; and
  iii. further comprises a power supply, a magnetron, and a waveguide, whereby the power supply energizes the magnetron to produce microwave energy, the microwave energy being conveyed by the waveguide to the applicator, and wherein the applicator directs the microwave energy towards the reaction chamber within the elongate reactor tube, thereby forming the plasma in the plasma reaction chamber, wherein the outflow gas products flow within the plasma reaction chamber towards the distal end of the elongate reactor tube and emerge from the distal end of the elongate reactor tube forming an outflow stream that enters the set of separation and purification subsystems; wherein the set of separation and purification subsystems:
  i. comprises, in fluid communication with the elongate reactor tube, an effluent separator that removes higher acetylenes and aromatics from the outflow stream, producing (a) a purified effluent stream comprising acetylene gas and hydrogen and (b) an offgas stream comprising higher acetylenes and aromatic impurities;
ii. further comprises, in fluid communication with the effluent separator, an acetylene separator which produces an acetylene-rich feedstock stream and a remaining effluent stream as separate streams;
iii. further comprises a hydrogen separator in fluid communication with the acetylene separator, wherein the hydrogen separator separates hydrogen as a purified hydrogen stream from the remaining effluent stream,
 1. wherein the hydrogen stream is separable into one or more of a recycled hydrogen stream, an integrated hydrogen stream, and an external hydrogen stream,
 2. wherein the external hydrogen stream is isolated from the integrated acetylene-based synthesis system as a first isolated hydrogen stream; and
b. wherein:
i. the acetylene-black manufacturing system comprises an acetylene decomposition reactor in fluid communication with the set of separation and purification subsystems;
ii. the acetylene decomposition reactor produces acetylene black and hydrogen from the acetylene-rich feedstock stream, and
iii. the hydrogen produced by the acetylene decomposition reactor is separable from the integrated acetylene-based synthesis system as a second isolated hydrogen stream.

The invention also encompasses a method for producing hydrogen, comprising:
a. providing the integrated acetylene-based synthesis system as described above,
b. processing a hydrocarbon-containing inflow gas to produce outflow gas products using the plasma-based hydrocarbon processing subsystem, wherein the outflow gas products comprise acetylene and hydrogen, wherein the step of processing comprises the steps of:
i. injecting the hydrocarbon-containing inflow gas into the plasma reaction chamber;
ii. energizing the hydrocarbon-containing inflow gas in the plasma reaction chamber with microwave energy to create a plasma;
iii. forming outflow gas products in the plasma, wherein the outflow gas products comprise acetylene and hydrogen;
iv. flowing the outflow gas products to exit the plasma reaction chamber;
c. separating the outflow gas products into a set of gas streams, the set of gas streams comprising a first gas stream comprising higher acetylenes and aromatic impurities, a second gas stream that is the purified hydrogen stream, and a third gas stream that is the acetylene-rich feedstock stream; wherein the step of separating the outflow products further comprises a substep of effluent separation to remove higher acetylenes from the first gas stream, and a step of acetylene separation to remove purified acetylene from the third gas stream;
d. isolating at least a portion of the purified hydrogen stream as a first isolated hydrogen stream;
e. directing the acetylene-rich feedstock stream into the acetylene-black manufacturing subsystem and producing hydrogen and acetylene black therefrom; and
f. isolating at least a portion of the hydrogen from step e as a second isolated hydrogen stream.

In certain embodiments, the systems and methods described herein further comprises a vacuum subsystem that maintains a first reduced pressure environment for the outflow products passing through one or more components of the effluent separation and disposal subsystem. The vacuum subsystem can produce a second reduced pressure environment within the elongate reactor tube, and/or it can produce a third reduced pressure environment for the gas delivery subsystem. In embodiments, the vacuum subsystem produces a first, second, and third reduced pressure environment; in embodiments, the first, second, and third reduced pressure environments are within a range of about 30 to about 120 Torr. In embodiments, at least one of the reduced pressure environments is between about 50 to about 100 Torr, or is between about 60 to about 80 Torr. In embodiments, the first, second, and third reduced pressure environments are substantially similar. The pressures in the first, second, and third reduced pressure environments are "substantially similar" when each of the pressures differ by less than about 10%, or less than about 5%. For example, if the pressure in the first reduced pressure environment is 70 Torr, the pressure in the second reduced pressure environment is 67 Torr, and the pressure in the third reduced pressure environment is 70 Torr then the pressures are substantially similar. In embodiments, the first reduced pressure environment has a pressure that is substantially higher than the pressure in the second and/or third reduced pressure environments. A pressure in the first reduced pressure environment is "substantially higher" than the pressure in the second and/or third reduced pressure environment, when the pressure is the first reduced pressure environment is at least about 10% greater, or at least about 15% greater, or at least about 20% greater than that of the second and/or the third reduced pressure environment. In certain embodiments, the first reduced pressure environment has a pressure between about 120 and about 280 Torr. In additional embodiments, the second and/or third reduced pressure environments have a pressure in a range between about 120 and about 280 Torr, while the first reduced pressure environment can have a pressure that is in the same range or is higher. In embodiments, the system further comprises a cooling subsystem. The cooling subsystem can comprise at least one of a water-cooling subsystem and a gas cooling subsystem. In embodiments, the gas cooling subsystem comprises a nitrogen-based cooling circuit, and the nitrogen-based cooling circuit can comprise one or more enclosures for components of the system, whereby the one or more enclosures are sealed sufficiently to enclose nitrogen gas around the components and exclude oxygen therefrom. In embodiments, the system comprises a data management and safety subsystem.

BRIEF DESCRIPTION OF THE FIGURES

FIG. 5, FIG. 6, and FIG. 7 illustrate embodiments of microwave subsystems.

DETAILED DESCRIPTION

Figure 1:
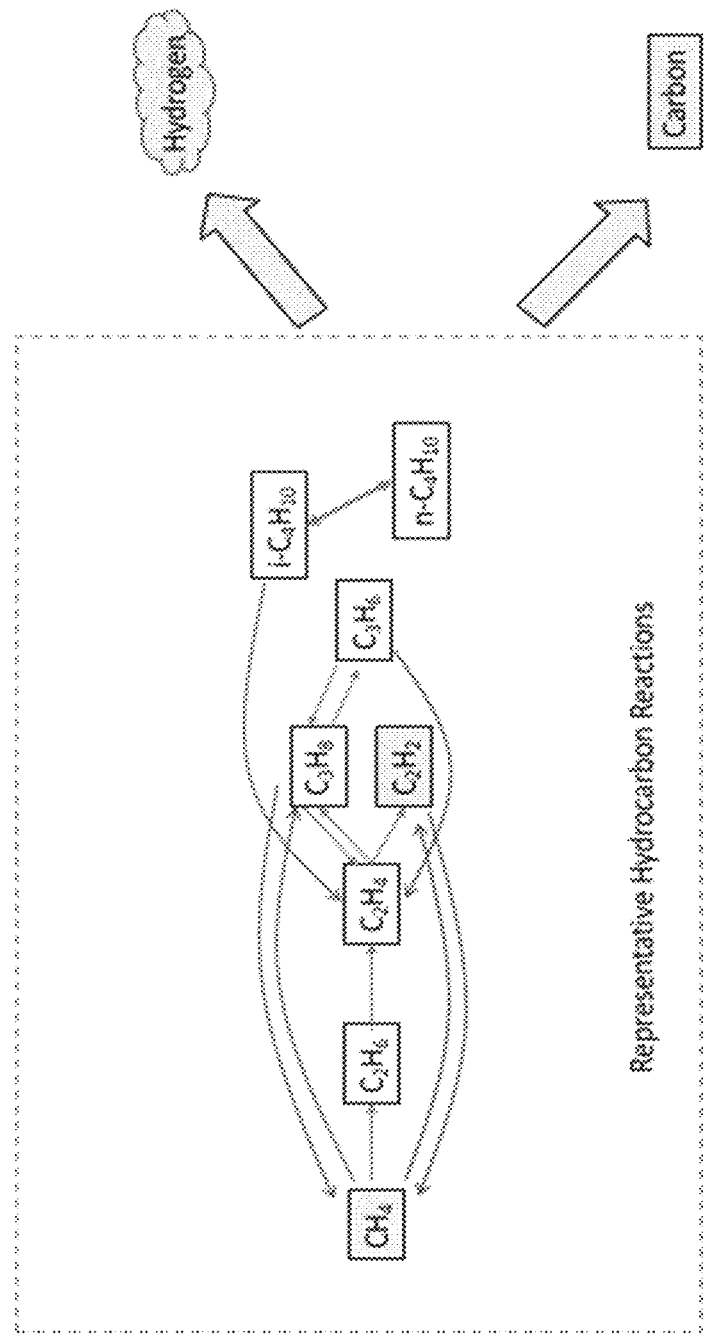
FIG. 1 is a schematic diagram showing various chemical reactions involved in the conversion of methane into hydrogen, carbon, and hydrocarbon products.

Disclosed herein in more detail are systems and methods for converting $C_1$-$C_4$ hydrocarbons, including unsaturated hydrocarbons and saturated hydrocarbons such as methane (as derived from mixed gas sources such as natural gas or biogas for example), into hydrogen, acetylene, and other carbon-based products. In embodiments, these systems and methods use non-thermal plasma produced by microwave energy to effect these conversions. In embodiments, the systems and methods disclosed herein can be optimized ("tuned") to maximize efficient production of acetylene, or of hydrogen, as products that can be isolated for further commercialization; in other embodiments, these systems and methods can be tuned to produce a combination of these gases for specific industrial purposes.

1. Overview a. Non-Thermal Plasmas

Plasma, the fourth state of matter, is an ionized gas: any gas can be turned into a plasma by applying enough energy to it to create a significant density of charged species, i.e., electrons and ions. Plasmas possess some of the properties of gases, but they differ from the ordinary gaseous state because they respond to both electric and magnetic fields, properties that are due to the charged species that exist in the plasma state. Despite having these properties, plasmas are electrically neutral, a characteristic termed quasi-neutrality. In addition to the ions and free electrons from the precursor gas that exist in the plasma, a plasma includes uncharged neutral gas species and precursor molecules that can enter into other chemical reactions. Some weakly ionized gases do not necessarily satisfy all of the conditions of a plasma but may still have many plasma-like qualities that influence their behavior. For example, many of the high-pressure plasmas used in industrial applications fall into this category.

One of the fundamental characteristics of a plasma is its temperature. Plasmas have been used in chemical and industrial applications because they can generate temperatures much greater than those obtained in traditional chemical engineering processes. In a plasma, energy is transferred to electrons, which in turn transfer energy to heavier particles through collisions. Electrons have a higher temperature than heavier particles, and an equilibrium temperature is reached that reflects the collisional frequency and radiative processes of the various particles in the plasma. Those plasmas having an electron temperature ($T_e$) that is close to that of the heavy particles' translational temperature ($T_0$) are defined as thermal plasmas, with gas temperatures greater than 3,000 K. By contrast, in non-thermal plasmas, highly energetic electrons can co-exist with species having substantially lower temperatures. Therefore, the translational temperature $T_0$ of the non-thermal plasma can be much lower than the electron temperature $T_e$ of the plasma—$T_e$ can be close to 11,600 K in industrial plasmas or even higher in other types of plasmas.

The energy situation in a plasma is more complex when the plasma contains molecules (such as $H_2$, $N_2$, or $CH_4$) instead of just atoms. These molecules have the ability to store energy in various rotational and vibrational motions, and therefore have rotational and vibrational temperatures associated with them. These temperatures for such plasmas generally lie in between the translational and electron temperature of the plasma, and they can affect the behavior of the plasma and its associated chemistry. The techniques disclosed herein are based on the ability of a non-thermal plasma to transfer the major portion of the electrical input energy to energetic electrons in the constitutive feed gas, rather than heating the gas itself. Through electron impacts, ionization, dissociation, and excitation, charged atomic and molecular species (e.g., electrons, ions, radicals) are generated that can participate in chemical reactions.

Methane is particularly resistant to chemical conversion because of its stability: breaking the C—H bonds in methane requires an enthalpy change of 1664 kJ mol$^{-1}$. Using the techniques described below, a non-thermal plasma can be produced and harnessed to break bonds in $C_1$-$C_4$ hydrocarbons, including methane bonds, and create acetylene and hydrogen molecules with high efficiency and selectivity.

b. Microwave Plasma Generation

In embodiments, the plasma used for these systems and methods is a microwave plasma, formed by directing microwave energy at the methane-containing feed gas, as described below in more detail. While methane is used as an exemplary embodiment in this description, it is understood that other short-chain alkanes (e.g., ethane, propane, butane) can be used as feed gases as well, either as single gas feed gases, or in combination with each other or with methane.

The microwave plasma process described herein is a gas phase process, using gaseous reactant precursors to form desired gaseous products. Because of the very fast oscillation frequency of the electric field relative to the molecular and electronic collision frequencies, microwave-generated plasmas are often in a high degree of non-equilibrium, meaning that electron and vibrational temperatures can be much greater than the gas temperature. In embodiments, collisions between the charged species (electrons, ions) and uncharged species (molecules, atoms, particles) in the microwave plasma transfer energy: this microwave-energized plasma supports a highly reactive chemical environment because of the energy contained in the plasma's free electrons. Because of the high degree of ionization of the precursor gas, the chemical dissociation and ionization of intermediates, and the elevated vibrational and excitational energies in the plasma, the desired chemical reactions described below proceed rapidly and efficiently.

Without being bound by theory, microwave radiation is understood to act as follows to create a plasma from a gaseous precursor. When the precursor gas (e.g., methane) is subjected to microwave radiation that meets or exceeds the dielectric strength of such gas, a free electron (present from background radiation or other sources) in the microwave field region is able to gain enough energy from the microwave electrical field in between collisions with neutral molecules that it can ionize another atom or molecule. The secondary ionized electron is subsequently accelerated in a direction that is governed by the electric field of microwave radiation, and it gains energy too until it causes another ionization event. This process of ionization progresses throughout the microwave field region until a steady state is reached. The final number of electrons in the plasma is determined mainly by the electron loss processes of the plasma, such as diffusion, recombination, and attachment.

The systems and methods disclosed herein use $C_1$-$C_4$ hydrocarbons such as methane as the reactant precursor gas that is subjected to microwave radiation. Methane may be used to exemplify a reactant precursor gas suitable for use in these systems and methods.

Methane dissociation in the plasma, initiated by collisions with the energized electrons as described above, results in the formation of $CH_x$ radicals. The major initial reaction is the breaking of the C—H bonds in methane, with resultant formation of CH3*, CH2*, CH*, H*, and C. These radicals can recombine to form two-carbon fragments as exemplified by the following equations:

$$CH_3^* + CH_3^* \rightarrow C_2H_6$$

$$CH_2^* + CH_2^* \rightarrow C_2H_4$$

$$CH^* + CH^* \rightarrow C_2H_2$$

$$CH_3^* + CH^* \rightarrow C_2H_4$$

$$CH_3^* + CH_2^* \rightarrow C_2H_4 + H^*$$

$$CH_3^* + CH^* \rightarrow C_2H_4$$

$$CH_3^* + CH^* \rightarrow C_2H_2 + H_2$$

$$CH_2^* + CH^* \rightarrow C_2H_2 + H^*$$

In addition, methane can combine with various radicals to form two-carbon fragments as exemplified by the following equations:

$$CH_4 + CH_3^* \rightarrow C_2H_6 + H^*$$

$$CH_4 + CH_2^* \rightarrow C_2H_6$$

$$CH_4 + CH_2^* \rightarrow C_2H_4 + 2H^* / H_2 CH_4 + CH^* \rightarrow C_2H_4$$

$$CH_4 + CH^* \rightarrow C_2H_2 + H^* + H_2$$

Besides the illustrated reactions to form two-carbon fragments and hydrogen, higher-order hydrocarbons can be formed by recombinations of plasma-generated radicals with each other and with the precursor gas. As used herein, the term "higher-order hydrocarbon" refers to any hydrocarbon having 3 or more carbon atoms, whether saturated or unsaturated, including aromatics.

Furthermore, complete dehydrogenation of methane can take place, resulting in the formation of elemental carbon and hydrogen gas. Representative reactions are show in FIG. 1. As shown in FIG. 1, a number of exemplary reactions producing hydrocarbons are shown within the dotted line, while the elemental products (hydrogen and carbon) are shown outside the dotted line.

In embodiments, parameters can be optimized to maximize acetylene formation. In other embodiments, parameters can be optimized to maximize hydrogen formation. As a general principle, for example, if the feed gases entering the plasma reaction chamber include less hydrogen as compared to hydrocarbon input, the output will be more hydrogen formed, potentially in combination with more carbon solids. Following this principle, in order to maximize hydrogen formation, a pure hydrocarbon feed could be used, and more of the desired hydrogen would be produced, along with a quantity of carbon solids. Factors affecting product selectivity (e.g., allowing the preferential formation of acetylene over other species, or allowing the preferential formation of hydrogen over hydrocarbon products) include, without limitation, the identity of the reactant precursor gas, the addition of other gases to the system, the flow rate of any gases entering the system, the temperature and pressure in the reactor system, the amount of microwave power and flow geometry used to create the plasma, the energy density in the reaction zone, the arrangement of the electrical field surrounding the plasma, and reactor vessel geometry and dimensions. In embodiments, static electric and magnetic fields can be employed to influence the behavior of the plasma and hence the product selectivity.

c. Precursor Gases

For the systems and methods disclosed herein, $C_1$-$C_4$ alkane hydrocarbons (for example, methane, ethane, propane, and butane) or other hydrocarbon gases can be used alone or in combination with other gases as precursor gases. In an embodiment of these systems and methods, methane is the main precursor gas. In embodiments, it can be combined with hydrogen and/or nitrogen as it enters the plasma reaction chamber, forming a single gas mixture that is energized to the plasma state. In embodiments, methane enters the plasma reaction chamber through its own set of nozzles, while other gases (such as hydrogen and/or nitrogen) are added to the plasma reaction chamber separately, through a different set or sets of nozzles. Methane can be used in a pure state, or it can be introduced into the system as a component of a commercially available gas stream.

Mixed gas sources such as natural gas or biogas are particularly advantageous sources of this precursor gas. As used herein, the term "biogas" refers to a mixed gas produced by the anaerobic decomposition of organic waste material in various natural or manmade environments; the term "biogas" includes all those natural or man-made environments in which such gas-producing anaerobic decomposition can take place, e.g., landfills, manure holding ponds, municipal waste sites, sewage treatment facilities, agricultural waste sites, permafrost decay, and the like. Biogas as collected or retrieved from those sites can be treated or upgraded to increase its methane content and to remove impurities, so that it becomes especially suitable as a precursor gas for the systems and methods disclosed herein.

Biogas, produced from raw materials such as municipal waste, agricultural waste, plant material, sewage, manure, food waste or other natural or manmade organic sources, is typically formed in a closed system via the anaerobic digestion or fermentation of the organic material. The first stage of this process is hydrolysis, in which the insoluble organic polymers are broken down into sugars and amino acids that serve as substrates for the activity of the anaerobic acidogenic bacteria. In a second stage, these bacteria convert the sugars and amino acids into carbon dioxide, hydrogen, ammonia, and organic acids; the acidogenic bacteria further convert the organic acids into acetic acid, ammonia and carbon dioxide. As a third stage, a separate population of anaerobic bacteria, the methanogens, convert these fermentation products into methane and carbon dioxide. Biogas, containing a mixture of methane and carbon dioxide along with gaseous byproducts such as hydrogen sulfide, can be collected and treated to remove carbon dioxide and the undesirable gaseous products, leaving a gaseous mixture with a high concentration of methane that is suitable for energy production or for further processing. Methane in biogas is concentrated using a process of biogas upgrading, resulting in a product that has similar performance characteristics to fossil-derived natural gas.

Processes such as water washing, adsorption, membrane separation, amine gas treatment, and the like, can be used for biogas upgrading. Upgrading processes can advantageously be carried out to remove oxygen from the biogas before it is used as a gas source. Oxygen in the feed gas can render it vulnerable to combustion; moreover, oxygen can corrode equipment used in the plasma-based hydrocarbon processing system as disclosed herein. Furthermore, under certain circumstances, oxygen removal may be necessary to meet regulatory standards or other purity requirements. A number of oxygen removal technologies are suitable for use with biogas. As an example, oxygen can be reacted with a reduced metal species, thus oxidizing the metal and consuming the oxygen. The oxidized metal species will then be regenerated back to the active form by reducing the metal species by passing a hydrogen or carbon monoxide containing gas stream over the metal species, generating water or carbon dioxide, respectively. Metal species such as palladium or nickel could be used to catalytically combust oxygen at >500° F. with hydrocarbon species mixed with the $O_2$. As another approach, solid scavengers can be used in a disposable fashion to trap oxygen. For example, $Fe_2S_3$ can react with three molar equivalents of molecular oxygen to form rust and elemental sulfur. As yet another approach, oxygen can be separated from other gases by molecular sieves, such as 5A or 13X molecular sieve, similar to the technology seen in air separation units (ASUs). Other upgrading processes for biogas would be available to skilled artisans using no more than routine experimentation. Upgraded biogas can reach a purity and quality similar to the natural gas in U.S. pipelines, and can be used for the same purposes.

Natural gas as extracted from the earth is predominantly methane, making it a useful source of precursor gas for these systems and methods. Typically, it also includes higher-order hydrocarbons such as ethane, propane, butane, and pentane, along with non-hydrocarbon impurities. The table below (Table 1) illustrates an exemplary composition of natural gas.

TABLE 1

| | | |
|---|---|---|
| Methane | $CH_4$ | 70-90% |
| Ethane | $C_2H_6$ | |
| Propane | $C_3H_8$ | 0-20% |
| Butane | $C_4H_{10}$ | |
| Carbon Dioxide | $CO_2$ | 0-8% |
| Oxygen | $O_2$ | 0-0.2% |
| Nitrogen | $N_2$ | 0-5% |
| Hydrogen sulfide | $H_2S$ | 0-5% |
| Rare gases | Ar, He, Ne, Xe | Trace |

Source: http://naturalgas.org/overview/background

Natural gas is generally processed to remove most of the non-methane components before it is made available for commercial or residential use, so that it is almost pure methane when it is reaches the consumer. As an example, natural gas available commercially can include about 96% methane. While an extensive system of pipelines exists in the United States to bring natural gas to consumer markets after it has been stripped of its impurities, much natural gas is found in areas that are far from these markets and far from the pipeline infrastructure (often termed remote or "stranded" natural gas). In embodiments, the systems and methods disclosed herein can be used in situ, for example at the location of the stranded natural gas, to convert it into acetylene and other useful products; these systems and methods accordingly offer a cost-effective way to utilize this stranded natural gas as a resource.

2. Systems and Subsystems

In embodiments, the plasma-based hydrocarbon processing system as disclosed herein can comprise six subsystems: 1) a gas delivery subsystem, 2) a microwave subsystem, 3) a vacuum subsystem, 4) a cooling subsystem, 5) an effluent separation and disposal subsystem, and 6) a data management and safety subsystem. These subsystems are described in more detail below. The integration of these subsystems is shown schematically on FIG. 2. Desirable outputs from these subsystems and methods can include a high degree of methane conversion, and a high degree of acetylene selectivity and/or a high degree of hydrogen selectivity.

Figure 2:
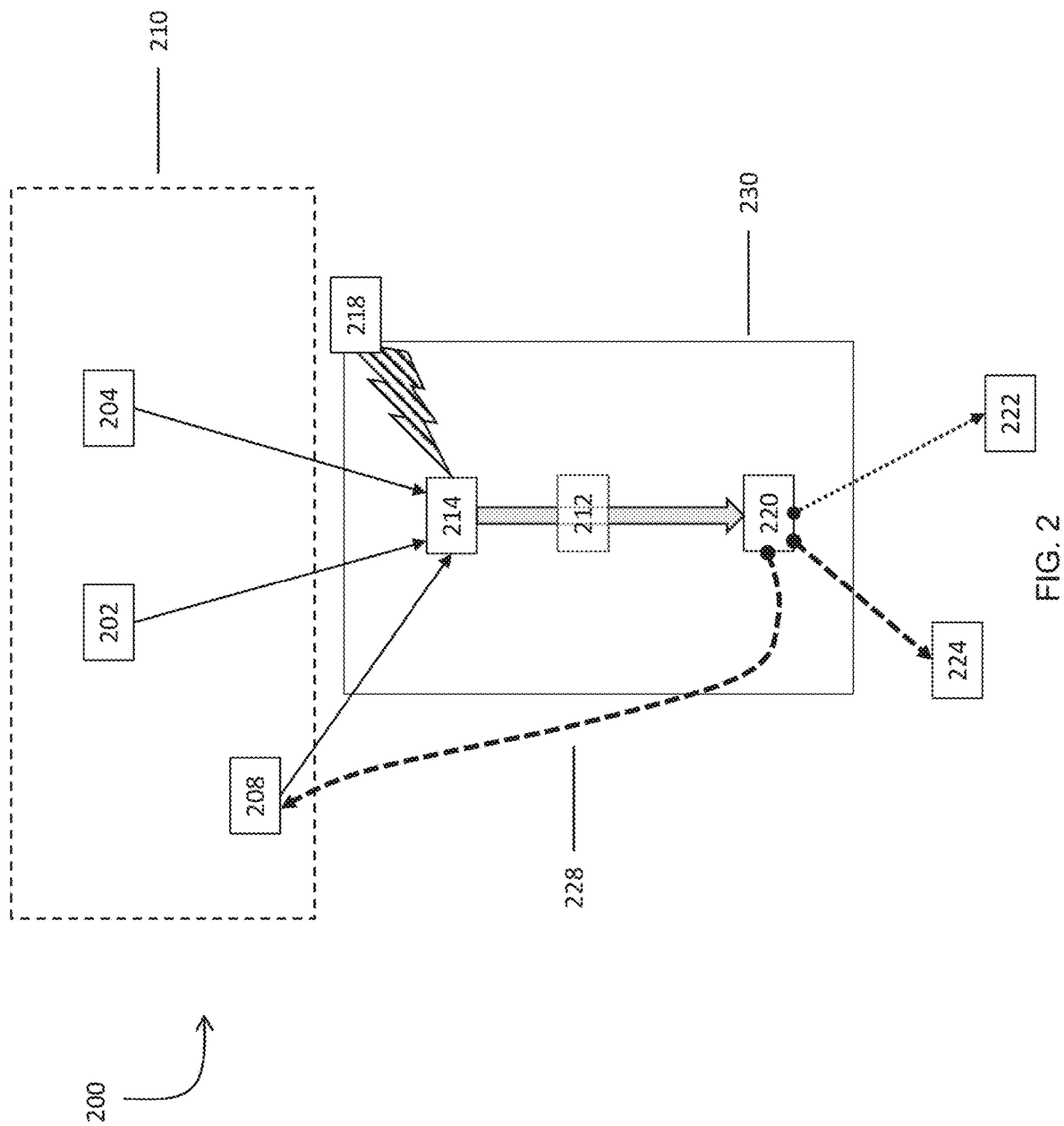
FIG. 2 depicts schematically a plasma-based hydrocarbon processing system and component subsystems.

As shown schematically in FIG. 2, a plasma-based hydrocarbon processing system 200 provides for the conversion of one or more inflow gases 202, 204, and 208 into a mixture of gaseous products contained in an outflow stream 212 emerging from a plasma reaction chamber 214, where the plasma reaction chamber contains the plasma that has been generated by a microwave subsystem 218. In the depicted embodiment, a hydrocarbon inflow gas 202, such as methane, enters the plasma reaction chamber 214 separately from the hydrogen-containing inflow gas 208 that is produced from a recycling of a certain fraction of the outflow stream 212. An optional auxiliary gas 204 such as nitrogen can be introduced separately as shown, or it can be mixed with one or both of the other inflow gases 202 and 208. The various inflow gas streams and their direction into the plasma reaction chamber 214 are encompassed by the gas delivery subsystem 210. The gas delivery subsystem 210 is responsible for producing the appropriate proportions of inflow gases and controlling their flow rates. Once the inflow gases enter the plasma reaction chamber 214, they are energized by microwaves produced by the microwave subsystem 218, which creates a plasma state within the plasma reaction chamber 214. An outflow stream 212 carries outflow (or "produced") gas products including acetylene, hydrogen, and a mixture of unreacted methane and higher-order hydrocarbons. Carbon solids can be entrained by the outflow gas stream 212. An effluent separation and disposal subsystem 220 allows for the separation of waste components from the outflow stream 212 so that they can be disposed of, and further allows for the separation of desirable components into discrete streams as necessary for further commercialization or for reintroduction into the plasma reaction chamber 214 as an inflow gas 208. For example, acetylene 224 can be separated from the outflow stream 212 in the separation/disposal subsystem 220, and it can be used commercially. In embodiments, for example, the acetylene can be further purified for use in chemical reactions. In other embodiments, the acetylene can be further processed, either to form other compounds or to form elemental carbon for other uses or for disposal. In embodiments, the carbon solids entrained by the outflow gas stream 212 can be removed by the separation/disposal subsystem 220 as a discrete product or waste material 222. In the depicted embodiment, a recycled stream 228 that is predominately hydrogen emerges from the separation/disposal subsystem and is recycled back into the plasma reaction chamber 214 as an inflow gas 208. In other embodiments, a portion or the entirety of hydrogen produced by the reactor can be separated from the outflow stream 212 and commercialized separately. In yet other embodiments, the separation of outflow stream 212 components proceeds differently: for example, carbon can be separated entirely, with a mixed hydrogen and hydrocarbon gas stream being segregated for commercialization or other uses. The separation/disposal subsystem can be configured to segregate single gases or gas mixtures in accordance with specific gas processing goals. As shown schematically in FIG. 2, a vacuum subsystem 230 surrounds certain system components to maintain them at a low pressure. A cooling subsystem (not shown) provides appropriate cooling for each system component.

In embodiments, a number of system parameters can be modified to optimize hydrocarbon (e.g., methane) conversion rate and acetylene or hydrogen selectivity, including input gas flow rate (SLM), input pressure, and power per converted hydrocarbon (e.g., methane). Tables 2a and 2b show the effect of varying these parameters in several different instances. A useful metric for comparing results of different system parameters is efficiency, calculated as the energy used per molecule of methane converted ($eV/CH_4$). This metric is easily applied to both industrial uses, such as production cost per kg of product, and scientific uses, such as comparing against bond strengths and calculating thermodynamic efficiency.

TABLE 2a

|  | 1 | 2 | 3 |
|---|---|---|---|
| Reactor I.D. (mm.) | 108 | 108 | 108 |
| $CH_4/H_2/N_2$ Feed flow (SLM) | 383/460/38 | 367/550/37 | 338/676/34 |
| Pressure (Torr) | 40 | 42 | 52 |
| $eV/CH_4$ | 3.90 | 4.07 | 4.42 |
| Effluent (SLM) | 1226 | 1285 | 1353 |
| $CH_4/H_2/N_2/C_2H_2$ Effluent (%) | 1.6/81.5/3.1/13.8 | 1.4/83.1/2.9/12.6 | 1.2/85.2/2.6/11 |
| $C_2H_2$ Selectivity (%) | 93 | 93 | 93 |

TABLE 2b

|  | 1 | 2 | 3 | 4 | 5 |
|---|---|---|---|---|---|
| Reactor I.D. (mm) | 108 | 108 | 108 | 45 | 45 |
| $CH_4/H_2/N_2$ Feed flow (SLM) | 383/460/38 | 367/550/37 | 338/676/34 | 310/628/31 | 310/628/31 |
| Pressure (Torr) | 40 | 42 | 52 | 195 | 254 |
| $eV/CH_4$ | 3.9 | 4.07 | 4.42 | 4.88 | 5.00 |
| Effluent (SLM) | 1226 | 1285 | 1353 | 1216 | 1206 |
| $CH_4/H_2/N_2/C_2H_2$ Effluent (%) | 1.6/81.5/3.1/13.8 | 1.4/83.1/2.9/12.6 | 1.2/85.2/2.6/11 | 2.6/80.4/4.8/11.6 | 3.0/80.2/4.8/11.3 |
| $C_2H_2$ Selectivity | 93 | 93 | 93 | 95 | 94 | a. Gas Delivery Subsystem

In embodiments, a gas delivery subsystem is constructed to direct inflow gases into the plasma reaction chamber. The gas delivery subsystem comprises two components, the delivery conduit and the gas injector. Included in the description of this subsystem are further descriptions of (i) gases fed into the reactor (inflow gases); (ii) the delivery conduit for conveying inflow gases into the plasma reaction chamber, where the delivery conduit includes one or more separate circuits (or "conveying circuits") for gas flow, and where the conveying circuits can include a main feed gas conveying circuit, auxiliary gas conveying circuits for additional gases besides the main feed gas, and/or a recycled gas conveying circuit to allow return of one or more produced gases (e.g., hydrogen) to be used as inflow gases for subsequent reactions, and (iii) the gas injector assembly in fluid communication with the delivery conduit and its component conveying circuits that introduces component inflow gases into the plasma reaction chamber itself.

i. Inflow Gases

Inflow gases can comprise precursor reactant gases such as $C_1$-$C_4$ alkane hydrocarbons in various combinations. Precursor reactant gases are those that provide hydrogens or carbons for further reactions in the plasma state. In embodiments, the inflow gases are methane and hydrogen, with nitrogen optionally combined with the methane. In certain embodiments, methane and hydrogen are reactants. The proportions of reactant gases, along with the optional nitrogen additive, can be varied empirically to optimize the product profile and yield.

Inflow gases used by the plasma-based hydrocarbon processing system can be supplied directly from feed tanks, feed lines, and/or through recycling. As used herein, the term "inflow gas" means any gas that is added to plasma reaction chamber within which the plasma is formed. An inflow gas can be a reactant gas such as methane or hydrogen, which is transformed by the plasma state into various products, as described in FIG. 1. An inflow gas can be an auxiliary additive gas such as nitrogen. An inflow gas can be supplied from external gas sources called "feed lines," or from intrasystem recycling, wherein a gas produced by the system is reintroduced, in whole or in part, into the plasma reaction chamber for subsequent reactions.

An inflow gas entering the system via an external gas source or feed line can be derived from a gas reservoir such as a storage tank, or it can be derived from an extrinsically situated flowing gas lines such as a mixed gas source line (e.g., a natural gas line or biogas line). In embodiments, the inflow gas contains solely (or substantially only) the reactants methane and hydrogen, with no deliberately added additional gaseous additives. The methane in the inflow gas can be obtained as a component of a more complex flowing gas mixture such as natural gas or biogas. In embodiments, methane and, optionally nitrogen, are fed in from feed lines (i.e., storage tanks or flowing gas lines), while hydrogen can be fed in from a storage tank or it can be recycled from the product stream and directed back into the reactor.

A recycled gas stream used for intrasystem recycling is an effluent (i.e., outflow gas) from the plasma reaction chamber, optionally separated into various component gases, with some or all of this gas or these gases reintroduced into the plasma reaction chamber. In embodiments, the hydrogen in the outflow gas products stream is separated from other gases and is recycled in a purified form. In embodiments, a hydrocarbon inflow gas is introduced into the plasma reaction chamber via a flowing gas feed line, for example a natural gas line or biogas line, while hydrogen is introduced into the plasma reaction chamber separately from the hydrocarbon inflow; this hydrogen can be derived, in whole or in part, from a recycled gas stream.

In embodiments, the recycled gas can comprise a hydrogen-rich reactant gas, wherein hydrogen is the main component, with some hydrocarbons also present that are capable of reactions. In embodiments, the recycled gas comprises the hydrogen-rich reactant gas, with the hydrogen-rich reactant gas in the recycled gas in an amount of 80% of the recycled gas or more, or about 85% of the recycled gas or more, or about 90% of the recycled gas or more, or about 95% of the recycled gas or more. A hydrogen-rich reactant gas can consist essentially of hydrogen, i.e., can include about 95% hydrogen or greater, or about 96% hydrogen or greater, or about 97% hydrogen or greater, or about 98% hydrogen or greater, or about 99% hydrogen or greater. In embodiments, the hydrogen-rich reactant gas comprises about 90% of the recycled gas or more, or about 91% of the recycled gas or more, or about 92% of the recycled gas or more, or about 93% of the recycled gas or more, or about 94% of the recycled gas or more. In embodiments, the recycled gas consists essentially of the hydrogen-rich reactant gas, i.e., the hydrogen-rich reactant gas comprises about 95% of the recycled gas or more, or about 96% of the recycled gas or more, or about 97% of the recycled gas or more, or about 98% of the recycled gas or more, or about 99% of the recycled gas or more. In embodiments, the recycled gas comprises a non-reactant gas such as nitrogen in addition to the hydrogen-rich reactant gas. In embodiments, the amount of hydrogen in the recycled gas can be in an amount of 80% or greater, 85% or greater, 90% or greater, or 95% or greater.

In embodiments, the remainder of the recycled gas apart from the hydrogen-rich reactant gas is nitrogen. In other embodiments, nitrogen is added as a separate auxiliary gas, apart from its presence or absence in the recycled gas. Volumes of hydrogen and nitrogen used in the system can be expressed in relation to the total methane flow. For example, the following ratio of inflow gas feeds can be used: 1:0-3:0.1 methane:hydrogen:nitrogen; in other embodiments, the following ratio of inflow gas feeds can be used: 1:1-2:0.1 methane:hydrogen:nitrogen. In embodiments, similar ratios of methane and hydrogen can be used in the absence of nitrogen. In an embodiment, a methane flow into the reactor of 300-400 SLM (approximately 11-14 SCFM) can be used. In an embodiment, a methane flow of about 380 SLM (13.4 SCFM) can be used. In embodiments, these flows are suitable for a reactor power of 100 kW.

In embodiments, the amount of hydrogen inflow gas can be varied in order to select for more or less acetylene production. Increasing the amount of hydrogen entering the reactor increases the amount of this gas available for reacting with methane, thereby improving the conversion selectivity for acetylene production and decreasing the amount of undesirable soot build-up. In embodiments, an increased amount of hydrogen entering the reactor decreases the amount of ethylene in the outflow, as compared to acetylene.

In embodiments, hydrogen is provided from hydrogen cylinders. In other embodiments, hydrogen can be provided by recycling hydrogen that is produced by the overall system: in other words, hydrogen produced from a $C_1$-$C_4$ hydrocarbon feedstock such as methane in the plasma reaction can be reused as a reactant. In certain embodiments, a recycled gas conveying circuit that conveys hydrogen as an inflow gas back into the system can be combined with a separate inflow source of hydrogen, for example from a hydrogen feed tank to tune the input of this gas. This approach can be advantageous at certain times during the production cycle, for example at system start-up when no recycled hydrogen has yet been produced, or to keep hydrogen inflow at a constant level despite variations in hydrogen produced during recycling.

In an embodiment, the gas delivery subsystem can be precharged, for example at system start-up, to balance the mixing of gases and to harmonize the gas flow with the microwave energy. First, the system can be evacuated and set at a near-vacuum pressure. Second, the system can be filled from an external source of hydrogen, either backfilled via hydrogen introduced retrograde into the recycled gas conveying circuit, or front-filled from a separate hydrogen inflow line. Third, a $C_1$-$C_4$ hydrocarbon (e.g., methane) or $C_1$-$C_4$ hydrocarbon/nitrogen mixture can be added as an inflow gas, with flows measured by flowmeters. With the system thus precharged with appropriate gases, the reactor can be energized, and the inflow gases can be processed. As the inflow gases are processed in the plasma reaction chamber, hydrogen is generated in the outflow gas products stream, along with other gas products. Hydrogen captured from the outflow gas products stream then can be recycled into the system, while at the same time the exogenous hydrogen inflow is decreased. This balancing of extrinsic and intrinsic hydrogen inflows (from external feed lines and from recycling) can facilitate a smooth start-up procedure for the overall system.

In embodiments, methane is the main component of the hydrocarbon containing inflow gas for the plasma-based hydrocarbon gas processing described in these systems and methods. In embodiments, methane can be introduced from gas cylinders, from pipelines, or from an inflow of a mixed gas (e.g., natural gas or biogas) as described previously. A set of compressors can be used, so that methane is introduced at a correct pressure, for example at a feed pressure of at least about 2 atm. If natural gas or biogas is used to provide the methane feed gas, the amount of available methane can be monitored, for example by using a benchtop gas chromatograph, and the impurities in the natural gas can be identified and removed. For example, if the natural gas or biogas feed contains sulfur, it can affect the purity of the acetylene product stream; such an impurity must be removed before processing. Various impurities that are commonly found in natural gas or biogas (e.g., carbon dioxide, mercaptans, hydrogen sulfide, and the like) can be removed with a series of pre-scrubbers, where the type of scrubber selected depends on the impurity to be removed.

Desirably, a mixed gas comprising methane can include a high concentration of methane, so that it is substantially free of impurities or other gases. Natural gas derived directly from a natural source without commercial treatment can contain about 90% or greater of methane. However, natural gas that is processed to be available commercially, or equivalently treated biogas, can be substantially free of non-methane gases and impurities. A hydrocarbon-containing inflow gas from such a source is deemed to consist essentially of methane, which term refers to an inflow gas containing about 95% of methane or greater. Such a gas, consisting essentially of methane, can contain, for example, about 95% methane or greater, or about 96% methane or greater, or about 97% methane or greater, or about 98% methane or greater, or about 99% methane or greater. Gases provided from natural sources such as in situ natural gas (as found in wells prior to processing) or such as biogas can contain lesser amounts of methane, but they can be pretreated for use as a hydrocarbon-containing inflow gas so that such gases have higher concentrations of methane; in embodiments, such pretreated gases consist essentially of methane when used as hydrocarbon-containing inflow gases for these systems and methods.

In embodiments, other auxiliary gases can be used as components of the inflow gas stream, for example additives such as nitrogen, carbon dioxide, and/or other reactive or inert gases. In an embodiment, nitrogen can be optionally used as a component of the inflow feed gas; it can also be used as a sealing gas for the vacuum pumps, as described below. In an embodiment, the inflow feed gas contains about 10% nitrogen, although this amount can be varied or tuned to optimize efficiency and selectivity for acetylene production; in other embodiments, nitrogen can be present in amounts ranging from about 0% to about 10%, with the nitrogen either deliberately added or extraneously present, for example as a minor component adventitiously found the feed gas. In other embodiments, no additional nitrogen is included. In addition to its use as an inflow gas component, nitrogen in gas and liquid form can be used as a part of the cooling subsystem to cool various components and provide a nitrogen "buffer" around the reactor, as described below. Carbon dioxide can be included as a separate component of the inflow gas, or it can be mixed into the reactor effluent to serve as an internal standard for gas chromatographic analysis of that effluent. In an embodiment, carbon dioxide is added to the effluent in the amount of 30% of the methane feed in order to achieve good precision in downstream gas chromatography measurements. Other auxiliary gases can be used as inflow gases along with the reactant gases, for example helium for gas chromatography and argon.

ii. Gas Delivery Conduit

The gas delivery conduit conveys the various inflow gases (including reactant gases, additive or auxiliary gases, and recycled gases) into the gas injector; the gas injector delivers the various inflow gases into the plasma reaction chamber. The gas delivery conduit contains conveying circuits dedicated to specific gas streams: the feed gas is carried within the feed gas conveying circuit, additional gases are carried by one or more additional gas conveying circuits, recycled gas(es) are carried by one or more recycled gas conveying circuits. In embodiments, these systems and methods use a hydrocarbon-bearing inflow stream as a main gas feed, for example a methane stream or a mixed gas stream (e.g., natural gas or biogas), with the main gas feed being carried by the feed gas conveying circuit. In embodiments, additional gas streams can also pass through the gas delivery conduit in addition to the main gas feed, adding inert gases such as nitrogen, and/or adding reactants such as hydrogen as separate streams via their designated conveying circuits. Furthermore, in embodiments, a recycled gas stream can be added to the mix through a recycled gas conveying circuit, as described in more detail below; a recycled gas stream can contain hydrogen as the predominant component, along with nitrogen, small quantities of other substances found in the natural gas feed, small quantities of unreacted methane, and other hydrocarbon components produced by the plasma-based hydrocarbon processing system. In embodiments, each conveying circuit is in fluid communication with the gas injector assembly and conveys its gas separately into the gas injector assembly, for example through a dedicated nozzle, valve, or conduit.

Figure 3:
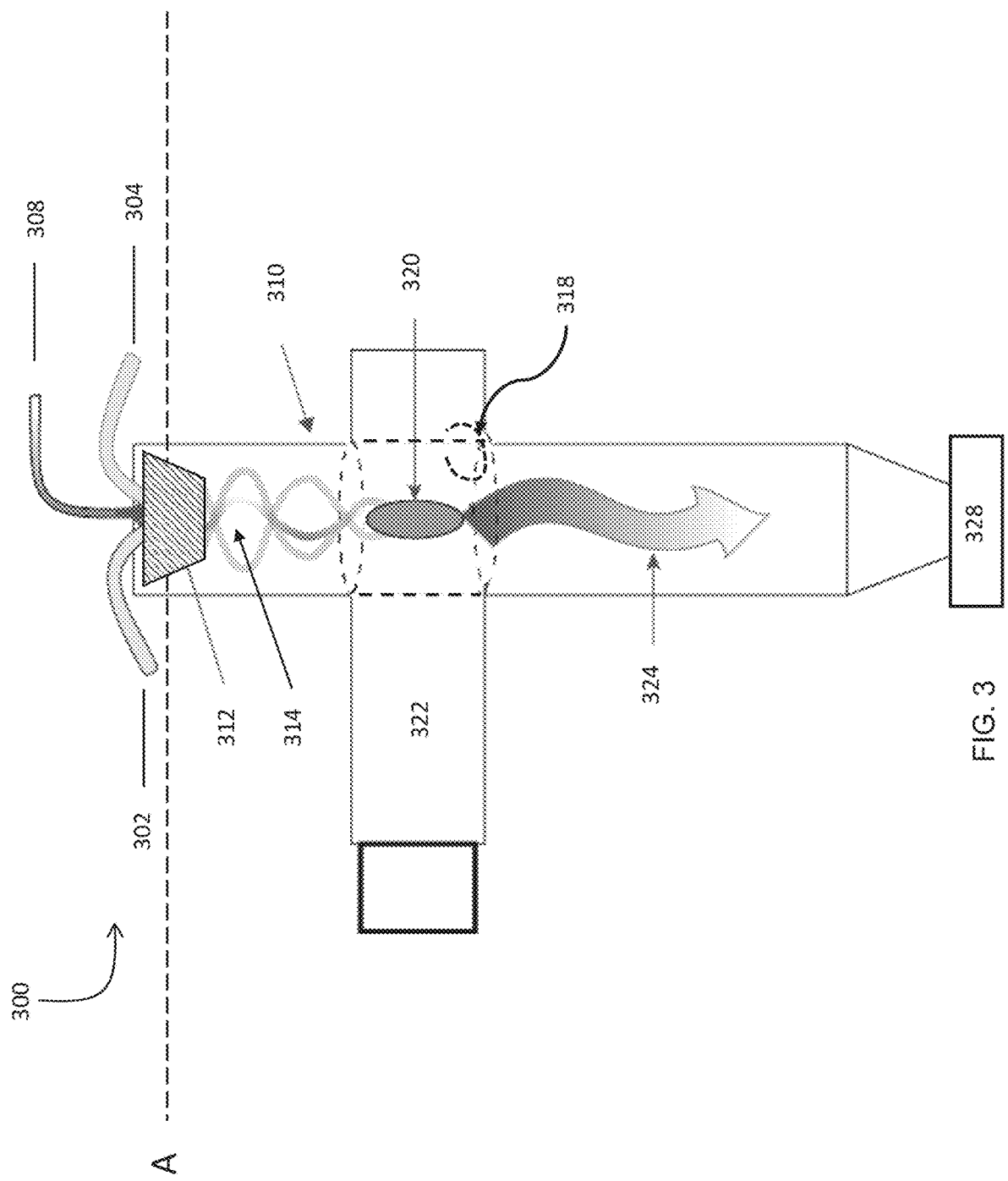
FIG. 3 depicts schematically a gas delivery subsystem.

A schematic diagram of an embodiment of a gas delivery subsystem 300 in accordance with these systems and methods is shown in FIG. 3. As shown in this Figure, a hydrocarbon-bearing inflow gas stream 302 is combined with a hydrogen-bearing inflow gas stream 304 and an optional auxiliary gas stream 308 to enter the plasma reaction chamber 310. In the depicted embodiment, the three gas streams enter through a gas injector 312 (described below in more detail) which disperses the various flows in directions and with velocities such that a vortex intermingling 314 of the three separate flows is produced within the plasma reaction chamber 310. The intermingled gases in the vortex intermingling 314 enter a reaction zone 318 of the plasma reaction chamber 310, where they are energized by the microwave energy produced in the microwave subsystem 322 to form the plasma 320 within the reaction zone 318 of the plasma reaction chamber 310. In the depicted embodiment, the inflow gases 302, 304 and 308 each enter the gas injector 312 as separate streams through separate inlets, and each enters the plasma reaction chamber 310 through its own outlet from the gas injector. The flow direction, flow velocity and flow rate from each outlet is oriented so that it produces the vortex intermingling 314 of the gases within the plasma reaction chamber 310.

Inflow gases can be introduced into the plasma reaction chamber in constant or variable flow patterns, and in continuous flow patterns or discontinuous flow patterns, and in any combination of these patterns. In embodiments, a variable flow pattern can be regular or irregular in its variability, and it can include intermittent pulses or surges of flow superimposed on an underlying wave form describing the flow pattern. A sinusoidal flow pattern would be an example of a variable flow pattern, as would a stepwise or "boxcar" flow pattern using square waves to delineate different amounts of flow. In embodiments, these variable flow patterns can include periods where there is no flow, so that the variable flow pattern would be discontinuous. In embodiments, gases can be introduced through all of the inlets simultaneously, or gases can be introduced through different inlets at different times. Gases can be introduced at different flow rates and at different flow patterns at each inlet. For example, a feed gas can be introduced continuously with a constant flow pattern, while one or more auxiliary gas streams can be introduced sporadically, i.e., discontinuously. Or, for example, the feed gas can be introduced discontinuously (i.e., with interruptions in its inflow), with one or more auxiliary gases introduced variably and/or discontinuously so that the auxiliary gases are flowing while the feed gas is not. Or, as another example, a feed gas can be introduced continuously with a continuous flow pattern, while one or more auxiliary gas streams can be introduced continuously, but with a different flow pattern than the feed gas. Other combinations of continuous/discontinuous patterning and flow pattern variability can be arranged to accomplish specific gas processing goals, for example, to decrease soot formation in the plasma reaction chamber, or to increase acetylene selectivity, or to allow for intermittent cleaning of the reaction tubing interior.

As previously described, gases that are energized into the plasma state undergo a spectrum of reactions, so that a hydrocarbon feed gas is transformed into other hydrocarbons plus hydrogen. FIG. 3 shows an outflow stream 324 emerging from the plasma 320 that contains the desired hydrocarbon product or products, certain extraneous hydrocarbon products, and hydrogen gas. The components of the outflow stream 324 are separated from each other by means of the effluent separation/disposal system 328, described previously.

iii. Gas Injector

The gas injector introduces the various inflow gas streams into the plasma reaction chamber through a plurality of inlets. In embodiments, the gas injector containing the flow channels for the various inflow gas streams can be printed out of a high temperature resin. It can be deployed within or is disposed in fluid communication with the reactor at a variable distance from the plasma reaction chamber within the reactor, where the term "plasma reaction chamber" refers to the region within the reactor where the microwave energy encounters the feed gas streams. In an embodiment, the gas injector can be positioned at the proximal end of the reactor, permitting antegrade gas flow from proximal to distal along the long axis of the reactor. In other embodiments, the gas injector can be positioned at the distal end of the reactor, or can be positioned at any other location along the long axis of the reactor. In embodiments, the gas injector is positioned centrally within the reactor tube, with gas flow directed peripherally. In other embodiments, the gas injector is positioned peripherally within the reactor tube, with gas flow directed centrally. Gas flow exiting the nozzles can be aimed at any angle along the long axis of the tube, so that gas can flow proximally or distally in an axial direction. The nozzles can be arranged to yield symmetric or asymmetric vortex flow.

In embodiments, the inflow gas flows can be aimed by the gas injector so as to create a spiral or vortical gas flow, which assists with mixing the various gas streams. The gas injector is configured to provide a separate nozzle or port for each inflow gas stream as it enters the reactor. The vortical flow can be produced from a gas injector device disposed centrally in the reactor with two or more nozzles or ports, where each inflow gas is separately delivered through its own subset of the one or more nozzles or ports. In an embodiment, these nozzles or ports, located centrally within the reactor, can be aimed peripherally, and can be angled to create the desired gas flow pattern. In other embodiments, vortical flow can be produced by gases flowing into the reactor through a gas injector having two or more nozzles or ports arrayed along the periphery of the reactor, where each inflow gas is separately delivered through its own discrete subset of the two or more nozzles or ports. In embodiments, the vortical flow serves to confine the plasma toward the interior region of the reactor. Additional vortex flow configurations, such as reverse vortex flow, can also be employed, as would be understood by those skilled in the art.

Figure 4A:
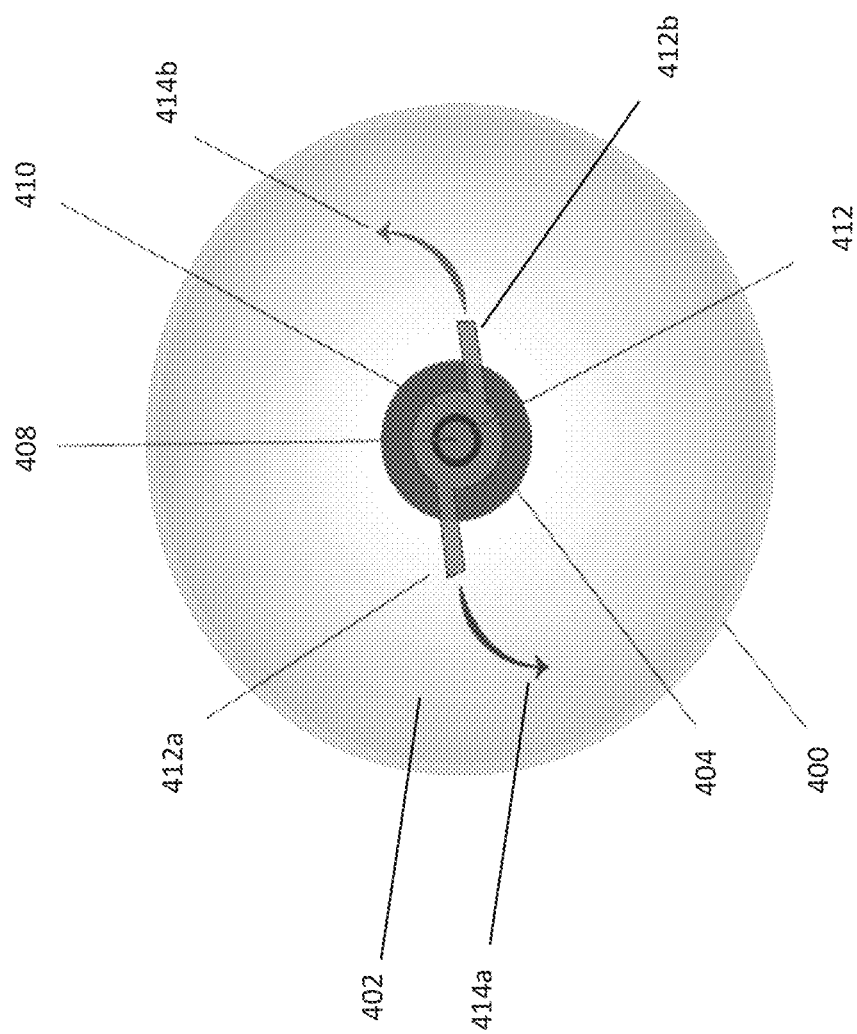
FIG. 4A and FIG. 4B illustrate embodiments of gas injectors.
Figure 4B:
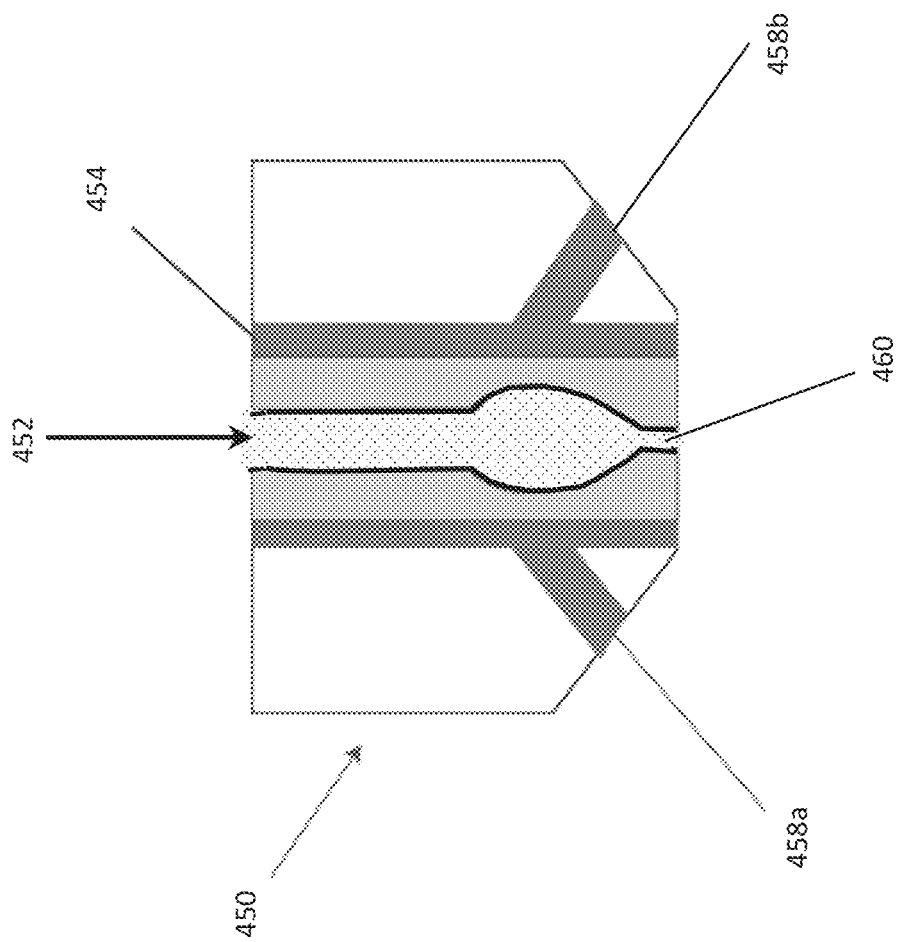

FIGS. 4A and 4B depict an embodiment of a gas injector that is compatible with these systems and methods. FIG. 4A shows a transverse cross-section of the proximal part of the reaction chamber 402 of a plasma reactor 400, within which the gas injector 404 is centrally located; the approximate location of the depicted cross-section in FIG. 4A is shown as Line A in FIG. 3. The gas injector 404 shown in this FIG. 4A encases two coaxial but separate gas flows, a central gas flow 408 and a secondary gas flow 410. The central gas flow 408 contains one gas, for example the main feed gas that can contain methane, the primary reactant. The secondary gas flow 410 contains a separate and distinct gas, for example an additional gas such as hydrogen or an auxiliary gas; this gas can also be a recycled gas such as hydrogen. Alternatively, the central gas flow 408 can contain the additional gas, while the secondary gas flow can contain the main feed gas. In other embodiments (not illustrated), the recycled gas flow can be maintained in a separate coaxial chamber distinct from a flow channel for an auxiliary gas, with each flow channel having its own set of one or more gas nozzles entering the plasma reaction chamber 402. For the injector design depicted in FIG. 4A, the central gas flow 408 exits the gas injector 404 centrally through a central gas nozzle 412 aimed distally and seen here only in cross-section, while the secondary gas flow 410 exits the gas injector 404 through gas nozzles 412a and 412b, which are aimed peripherally. As shown in this Figure, the secondary gas nozzles 412a and 412b are directed at an angle that allows the secondary gas flows 414a and 414b to enter the plasma reaction chamber 402 to form a gas vortex within the reactor 400.

FIG. 4B shows a longitudinal section of an embodiment of a gas injector 450, incorporating the principles illustrated in FIG. 4A. The gas injector 450 depicted in FIG. 4B shows the coaxial arrangement of the central gas flow 452 surrounded by the secondary gas flow 454. The gas injector 450 is positioned centrally within the reactor (not shown in the Figure), and the gas flows from the central gas flow 452 and the secondary gas flow 454 exit the gas injector 450 to flow into the reactor. The secondary gas nozzles 458a and 458b can be arranged at angles (as seen in FIG. 4A), so that secondary gas exiting these nozzles is aimed to create a vortex flow. As well, the gas exiting the primary gas nozzle 460 can be directed to create or to contribute to a vortex flow. In embodiments, the vortex flow created in the reactor 400 by the gas injector 450 permits gas mixing, which in turn can optimize the exposure of the gas streams to the plasma.

b. Microwave Subsystem

In embodiments, the microwave subsystem comprises the various components used to generate, guide, and apply microwave power to form the non-thermal plasma that transforms the feed gas into its products.

Figure 6:
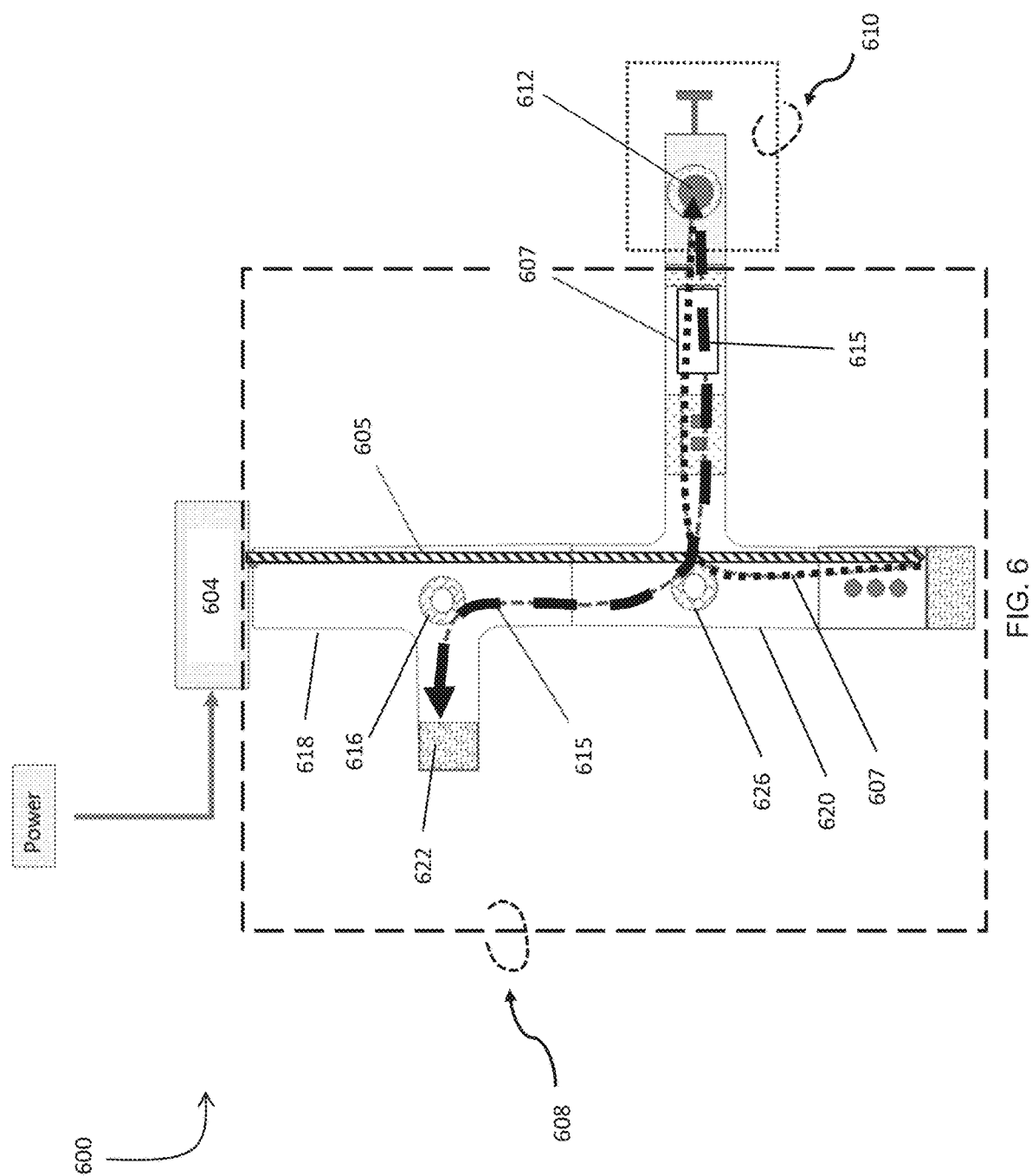

A schematic diagram for an embodiment of a microwave subsystem is shown in FIGS. 5 and 6 below. FIG. 5 provides an overview of the subsystem's components. As shown in FIG. 5, an embodiment of the microwave subsystem 500 includes a power supply 502, a magnetron 504, a waveguide assembly 508, and an applicator 510, with the microwave energy produced by the magnetron 504 encountering the inflow gas in a plasma reaction chamber 512 within an elongate reactor tube 514 (seen here in cross-section) to create the plasma. The reactor tube 514 can be made of quartz, as is described below in more detail. In an embodiment, the power supply 502 requires 480 V, 150 A of AC electrical power to generate 20 kV, 5.8 A of low ripple DC power with an efficiency of 96% to energize the magnetron. In an embodiment, the magnetron 504, also rated at 100 kW, produces microwave power at 83-89% efficiency. In embodiments, the microwaves produced are in the L-band, having a frequency of 915 MHz.

As shown in this Figure, the microwaves enter a waveguide assembly 508 that directs them to the applicator 510, which in turn directs the microwaves to the plasma reaction chamber 512 in the reactor tube 514. In the depicted embodiment, the waveguide assembly 508 comprises two circulators 518 and 520, which direct the microwaves towards the applicator 510 and which prevent reflected microwave power from coupling back into the magnetron 504 and damaging it. Each circulator 518 and 520 contains a ferrite array 516 and 526 respectively that deflects reflected microwaves in order to direct them towards the applicator 510 and plasma reaction chamber 512, as described below in more detail. Each circulator 518 and 520 has its respective water load 522 and 524 at its end to collect the reflected microwaves. As depicted, the second circulator 520 includes a power tuner 528 that steps down power using a three-stub tuner 530 in the arm that is distal to its junction with the applicator. In the arm of the second circulator 520 that interfaces with the applicator 510, a three-stub tuner 532 is arranged distal to the dual-directional coupler 534; this arrangement is intended to minimize microwave reflection and optimize the microwave energy directed into the applicator 510. A quartz window 538 is inserted between the second circulator 520 and the applicator 510 to prevent arcing. When the plasma is off and the microwaves are on, a standing wave is set up in the applicator 510 between the three-stub tuner 532 and a sliding shorting plate 540 on the end of the applicator 510 such that the electric field is sufficient to initiate breakdown of the feed gases in the reactor tube 514 that contains the plasma reaction chamber 512. The reactor tube 514 runs through the broad wall of the applicator 510 but is not in direct contact with the microwave waveguide 508. Once the initiation of the plasma state is achieved, the three-stub tuner 532 can then be adjusted to match the impedance of the incoming microwave signal to the plasma-loaded applicator 510. Microwave energy entering the applicator 510 is tuned to peak at the center of the plasma reaction chamber 512, using the shorting plate 540 as needed to change the dimensions of the cavity within which the plasma is formed.

To optimize the power for producing the plasma, it is desirable to match the impedance of the waveguide 508 to the impedance of the applicator 510 in the presence and the absence of the plasma. Plasma impedance is dynamic however, and can change based on the operating pressures, gas flows, and gas compositions in the plasma reaction chamber 512. In embodiments, the microwave subsystem can be equipped with a standard three-stub autotuner 532, which has three metal stubs inserted into the waveguide. The depth to which each of these stubs is inserted into the waveguide alters the phase of the microwaves entering the reactor 510 and allows for power matching into the plasma. Microwave power and phase measurement in the autotuner 532 allow the autotuner 532 to modify stub depth algorithmically, so that reflected power (i.e., the power not absorbed by the plasma), is minimized. In embodiments, a dual directional coupler 534 with attached power diodes (not labeled) can be included, to measure forward and reflected power in the subsystem. The coupler 534 can be fitted with two small holes that couple microwaves with a known attenuation to the diodes, which convert the microwave into a voltage. In embodiments, reflected power is less than 1% of total microwave power sent into the system. In embodiments, the microwave applicator 510 is a single-mode resonant cavity that couples the microwaves to the flowing gas feed in the plasma reaction chamber 512. A sliding electrical short 540 can be built into the applicator 510 to change total cavity length. In embodiments, the plasma for the 100-kW demo unit can generate upwards of 10 kW of heat, which can be removed via water and gas cooling subsystems.

The plasma is created in the plasma reaction chamber 512 within the elongate reactor tube 514. In embodiments, the reactor tube 514 can comprise a long aspect ratio fused quartz tube, with an outer diameter. between about 30 and about 120 mm, a length of approximately 6 ft, and a thickness varying from about 2.5-6.0 mm. In an embodiment, the reactor tube can have an outer diameter of 50 mm, or an outer diameter of 38 mm. In embodiments, tube sizes can have an outer diameter (OD) and corresponding inner diameter (ID) of 120/114 mm OD/ID, or 120/108 mm OD/ID, or 80/75 mm OD/ID, or 50/46 mm OD/ID, or 38/35 mm OD/ID. In embodiments, the reactor tube 514 has a consistent diameter throughout its length. In other embodiments, the reactor tube 514 can have a varying diameter, with certain portions of the tube 514 having a smaller diameter, and other areas having a larger diameter. In embodiments, a tube can have an outer diameter of about 50 mm at the top and about 65 mm at the bottom. In embodiments, the tube can have a narrower diameter at a preselected portion of the tube, for example, approximately in the middle of the tube. Quartz is advantageous as a reactor tube 514 material because it has high temperature handling, thermal shock resistance, and low microwave absorption.

FIG. 6 shows, in more detail, a microwave subsystem 600, such as was depicted in FIG. 5, and the paths of microwave energy 605, 607, and 615 flowing therein; in FIG. 6, certain features of the microwave subsystem 600 are shown schematically but, for clarity, were not labeled as they were in FIG. 5. As shown in the embodiment depicted in FIG. 6, microwave energy, generated by the magnetron 604, is directed forward along a forward energy path 605 from the magnetron 604 to the distal end of the waveguide assembly 608, from which it is reflected along an antegrade (forward) reflected path 607. The direction of the antegrade (forward) reflected path 607 is shaped by its encounter with the ferrite array 626 in the second circulator 620, which deflects the reflected microwaves 607 towards the applicator 610 and the plasma reaction chamber 612. Microwaves can also be reflected retrograde from the applicator 610 along a retrograde (reverse) reflected path 615, which passes backwards through the second circulator 620 into the first circulator 618, where the microwaves in this path 615 are collected by the water load 622 within the first circulator 618. The retrograde (reverse) reflected path 615 is deflected by the ferrite array 626 in the second circulator 620, and then by the ferrite array 616 in the first circulator 618 to establish its final direction. In an embodiment, forward power in the system is approximately 25 kW, with reflected power 1% of this or less, with the goal of 0% reflected microwave energy. In embodiments, the forward power in the system is approximately 30 kW; in other embodiments, the forward power in the system is approximately 100 kW. In yet other embodiments, forward power levels of about 8 kW, about 10 kW, or about 19-20 kW can be employed. In embodiments, the system can advantageously encompass a forward power at levels less than about 100 kW.

Figure 7:
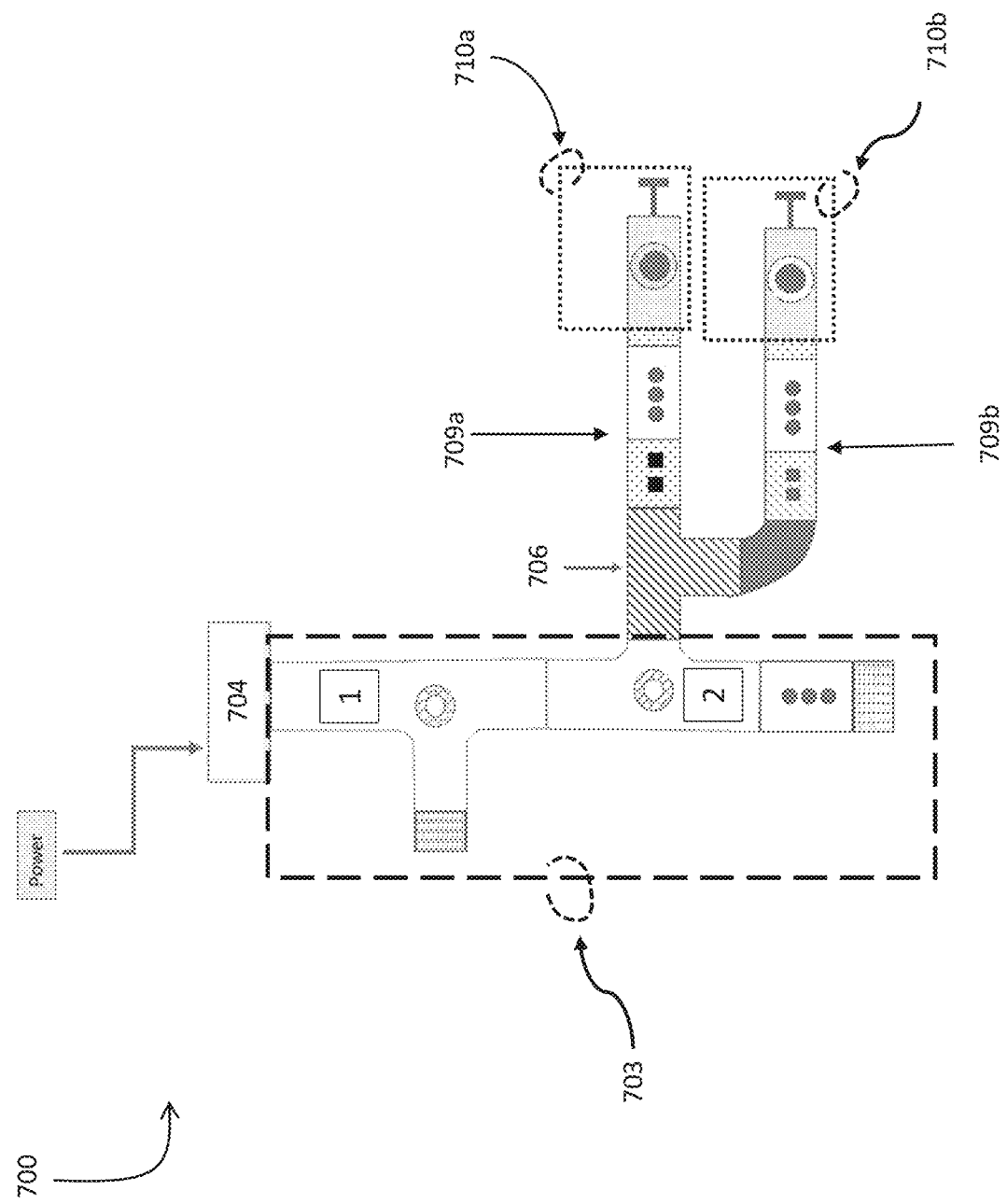

In an embodiment, the microwave subsystem includes a single arm pathway towards the plasma reaction chamber, as depicted in FIG. 5 and FIG. 6. In other embodiments, a double-arm applicator pathway can be employed, as shown below in FIG. 7. As shown schematically in FIG. 7, a double-armed microwave subsystem 700 comprises a magnetron 704 producing microwave energy that enters the circulator assembly 703, which comprises two circulators, labeled "1" and "2." Microwave energy passes through the circulators substantially as depicted in FIG. 6, to enter a power splitter 706 that directs the microwaves into two waveguide arms 709*a* and 709*b*, within which arms the microwaves are aimed towards their respective applicators 710*a* and 710*b*. In embodiments, the double-arm waveguide 709*a* and 709*b* plus applicators 710*a* and 710*b* can split the incident power in a 50:50 ratio, but in other embodiments, a selected ratio of power splitting can be engineered.

Certain maintenance measures within the microwave subsystem can extend the lifespan of the components and optimize the product output. In embodiments, for example, the reactor can be cleaned periodically. It is understood that carbon soot build-up can occur in the reactor tube when non-thermal plasma technology is used to convert methane to acetylene, and the presence of soot can lead to localized areas of overheating on the quartz surface with subsequent damage to the reactor tube. In addition, soot that accumulates distal to the microwave coupling can become conductive, leading to formation of undesirable arcs. Therefore, in embodiments, regular cleaning of the reactor is undertaken in order to minimize these problems. Cleaning can be undertaken on a periodic basis, or based on the discontinuous demands for commercial operation, or in response to observable characteristics of the plasma or effluent. For cleaning purposes, several steps are typically employed: 1) de-energizing the plasma process with in the plasma reaction chamber, either by switching off the microwave power creating the plasma, or by shifting the gas inflow from the process gas to an inert cleaning gas or gas mixture (e.g., pure $N_2$ or a combination of nitrogen with air or with other cleaning gases), or both; 2) discontinuing the feed gas inflow and introducing an inert gas mixture (e.g., nitrogen) that purges the inflow lines of the flammable feed gas; 3) filling the reactor with the cleaning gas (e.g., nitrogen mixed with air); 4) re-energizing the plasma reaction chamber with microwave energy to create a plasma state from the cleaning gas, including monitoring and adjusting the microwave energy and the pressure to permit effective cleaning; 5) reversing the process once the reactor tube is clean, with evacuation of the cleaning gas or displacement of the cleaning gas by the feed gas, leading to filling the reactor tube with the feed gas, and subsequent energizing of the feed gas to form a plasma.

In embodiments, soot deposition (and therefore the need for cleaning) can be minimized by increasing the hydrogen component of the inflow gases; this approach, however, has the drawback of decreased efficiency in hydrocarbon (e.g., methane) conversion. In other embodiments, soot deposition can be managed directly by periodic manual cleaning; this approach has the drawback of requiring physical interventions to access the internal surfaces of the reactor tubing where the soot accumulates. In yet other embodiments, soot deposition can be managed by periodically changing the gas inflow into the plasma reaction chamber from the hydrocarbon:hydrogen feedstock used to produce acetylene to a hydrogen:nitrogen mix which, at low power, forms a plasma that removes soot that has been deposited on the inner surface of the reactor tube. In an embodiment, a pure $CO_2$ plasma can be used as a cleaning plasma. In an embodiment, a hydrogen:nitrogen gas mixture can be used, with a H:N ratio of 5-15:1 can be used, at a power of about 8 kW. In an embodiment, this gas-based cleaning protocol can be carried out on a periodic basis (for example, with a cleaning run of 1-2 minutes every hour or two), aiming for a 1-2% downtime for cleaning out of the continuous run scheme. In other embodiments, a nitrogen:air mixture at a 50:4 ratio can be used, resulting in a cleaning time of about three minutes every 2-3 hours.

An embodiment of this system contains parallel microwave reactor setups multiplexed together, with a first reactor and a second reactor joined after the reactor tube and heat exchanger and isolation valves for each reactor but sharing vacuum pumps. A first reactor's magnetron can be shut off and, and the reactor isolated by the isolation valve, then opened to an alternate vacuum system, while the second reactor is operating to energize the feedstock gas in its plasma reaction chamber. A cleaning plasma can then be utilized for the first reactor. Once the cleaning is done, the first reactor system will be evacuated of the cleaning gas mixture and purged with nitrogen, then purged again by the respective mixture of new feed gas and recycled gas used for the process, then reopened to the main vacuum system and reignited. The second reactor can be cleaned in turn, using the same sequence. In some embodiments, the total number of parallel reactors can be increased to include three or more reactors, with their cleaning cycles sequenced such that the total throughput of the multiplexed system is constant while any one reactor is undergoing cleaning. This cleaning step can therefore be cycled through the multiplexed reactor system individually or in small groups indefinitely, with cycles timed such that there is no loss in product throughput over continuous use.

c. Vacuum Subsystem

In embodiments, a vacuum system is arranged around all components between the gas injector providing gas inflow to the reactor and the product outflow stream distal to the reactor. Maintaining a low pressure in the system contributes to its efficiency (where efficiency is measured by eV of energy per mol of methane converted to acetylene). In embodiments, a vacuum is maintained in the reactor, or a low pressure environment is produced, on the order of about 30 to about 120 Torr, or 60 to about 100 Torr, or 70 to about 80 Torr. In embodiments, a low pressure environment on the order of about 120 to about 280 Torr, or about 150 to about 200 Torr, or about 170 Torr. In an embodiment, an operating pressure of about 70 Torr is maintained for all hydrocarbon feed gases except ethane, which is processed at an operating pressure of about 120 Torr.

Figure 8:
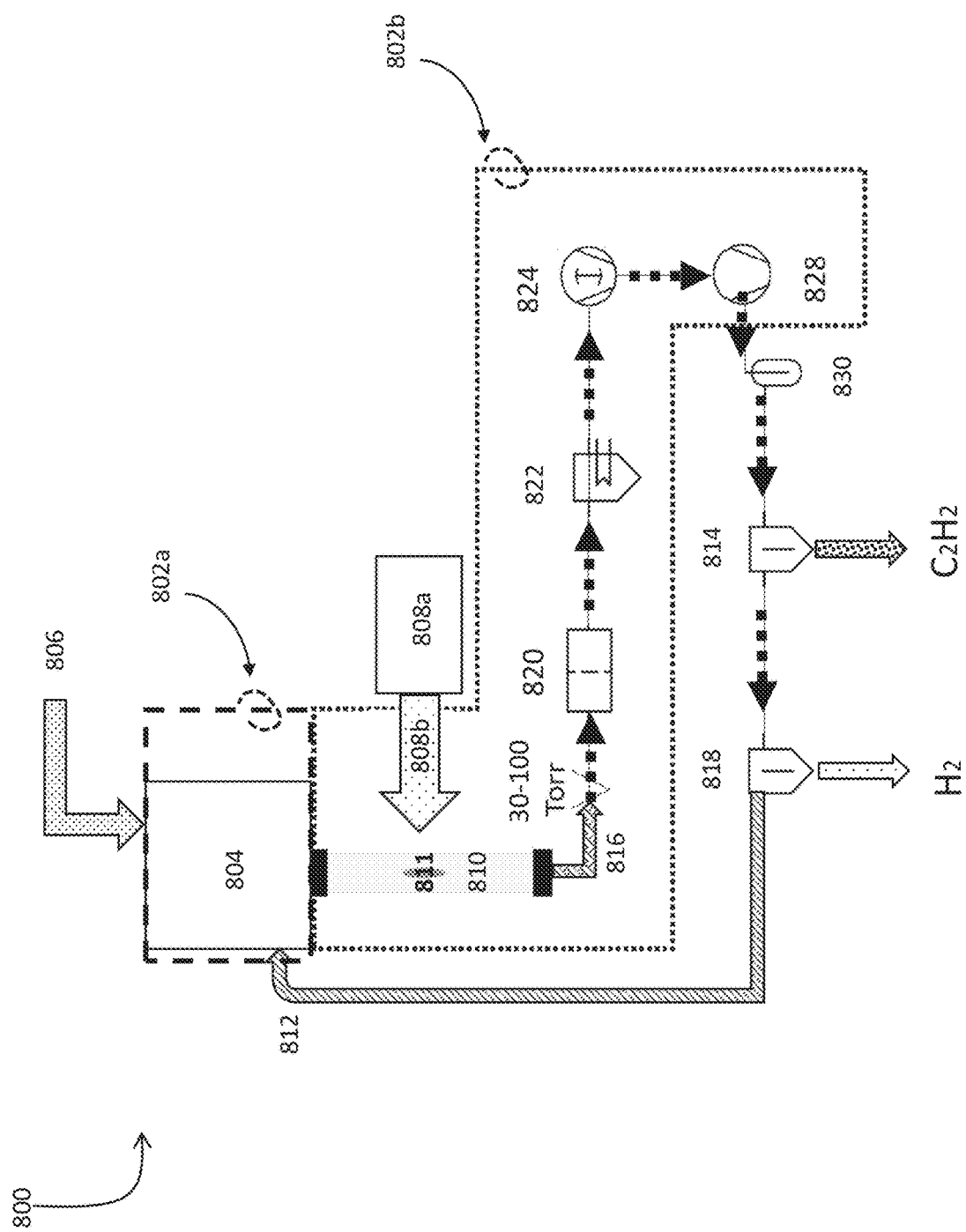
FIG. 8 is a schematic showing a vacuum subsystem integrated with other subsystems of a plasma-based hydrocarbon processing system.

A simplified schematic of a plasma-based hydrocarbon processing system 800 highlighting the vacuum subsystem 802*a* and 802*b* is shown in the FIG. 8, with arrows indicating the direction of gaseous flow throughout the system 800. The vacuum subsystem 802*a* and 802*b* envelopes certain components of the processing system 800 to maintain a pressure in those components in the range of about 30 to about 120 Torr Alternately, the same system can maintain a pressure in those components in the range of about 120 to about 280 Torr, or about 150 to about 200 Torr, or about 170 Torr. As depicted in FIG. 8, the vacuum subsystem designated by the dashed line 802*a* creates a first reduced-pressure environment around the reactor 810 and its outflow stream 816, and around various components downstream from the reactor 810, all as described in more detail below; the vacuum subsystem designated by the dashed line 802*b* creates a second reduced pressure environment around the gas delivery subsystem 804. For purposes of clarity, a portion of the vacuum subsystem is identified by dashed line 802*a* and a portion of the vacuum subsystem is identified by dashed line 802*b*; these two dashed lines can represent separate subsystems, or they can be merged together to represent a single vacuum subsystem. Subsystems and components shown in this Figure for clarity include: (i) the gas delivery subsystem 804 that passes the inflow gases, including hydrocarbon feed gas 806 and hydrogen-containing recycled gas 812, through their respective feed gas inlets (not shown) into the reactor 810; (ii) a microwave delivery system 808*a* that forms the microwaves 808*b* that act upon the inflow gases (i.e., the hydrocarbon feed gas 806 and the hydrogen-bearing recycled gas 812) in the reactor 810 to effect chemical transformations in the two inflow gases 806 and 812 in the plasma reaction chamber 811 region of the reactor 810, with the products of these chemical transformations exiting the reactor 810 as the outflow stream 816; (iii) an effluent separation and disposal system comprising an acetylene separator 814 and a hydrogen separator 818 that separates the outflow stream 816 into its gaseous components, with the remainder of the outflow stream 816 distal to the acetylene separator 814 and the hydrogen separator 818 becomes the recycled gas stream 812. As mentioned previously and as shown in this Figure, certain components situated downstream from the reactor 810 are also contained within the vacuum subsystem as designated by dashed line 802*a*, such as a filter 820 for the outflow stream 816, a heat exchanger/separator 822, and a series of pumps 824 and 828. In this Figure, a cold trap 830 for removing higher order hydrocarbons is situated outside the vacuum subsystem as designated by dashed line 802*a*, as are the acetylene separator 814 and the hydrogen separator 818.

The filter 820 shown in the Figure is intended to remove carbon solids from the outflow stream 816. In embodiments, the plasma process makes a small amount of carbon solids as a by-product; for example, carbon solids can be produced in the range of 0.1-0.5%. Therefore, it is desirable to filter the outflow stream 816 to remove these carbon solids in order to prevent these particles from fouling the downstream components of the system. Since the filter 820 is the first surface that the outflow stream 816 encounters after leaving the reactor 810, the gas in this stream is very hot (on the order of 400-1000° C.). Therefore, the material for the filter 820 is selected so that it can withstand such temperatures, with or without additional cooling. In embodiments, the filter 820 can be made of ceramic materials or of stainless steel, with cooling added as needed.

d. Cooling Subsystem

In embodiments, a cooling subsystem can be implemented to control the operating temperatures for the various components of the gas processing system described herein. In embodiments, the plasma formed in the reactor reaches a temperature between 2000-3000 K (1700-2700° C.), exiting the reactor at a temperature of about 400-1100° C. To protect the downstream components of the system from heat damage, cooling is provided. In addition, it is desirable to cool the reactor itself, for example to keep the outer temperature of the reactor tube below 500° C. Moreover, the reactor tube is more likely to retain heat during gas-based cleaning (as described above) vs during acetylene production, so that more cooling power can be required intermittently to protect the reactor tube from heat stress. In embodiments, the cooling for the system includes two types of cooling: water cooling and gas cooling. Water cooling can be used for many of the components of the system, for example the magnetron, the power supply, the vacuum pumps, the applicator, and the like. Gas cooling can be employed for other components as appropriate, for example, the reactor tube, the reactor itself, and the various O-ring seals in the system. In embodiments, nitrogen is used for gas cooling. Nitrogen has the additional benefit of replacing atmospheric gases in enclosed parts of the system, thus enhancing safety. In an embodiment, the reactor tube and the applicator can be enclosed in a sealed, nitrogen-purged (oxygen-free) environment, where the presence of nitrogen provides cooling and also serves as a safety mechanism: by replacing the oxygen in the environment around the reactor system, the nitrogen gas coolant reduces the chance of explosion if a leak is created.

e. Effluent Separation and Disposal Subsystem

In embodiments, the outflow stream emerges from the low-pressure environment created by the vacuum subsystem, and then undergoes further management to separate the desired gaseous products from each other and from the waste products. Methane and other hydrocarbon-containing gases such as ethane, propane, butane and the like produce acetylene and hydrogen when energized in a non-thermal plasma as described herein, along with particulate carbon and higher-order hydrocarbons. To optimize the economics of the process and to provide a customized gas flow for recycling, a set of components is positioned distal to the vacuum subsystem to segregate certain of the gaseous components in the outflow stream from each other.

In embodiments, it is envisioned that a plasma-based hydrocarbon processing system and the methods of its use described herein convert methane in a stoichiometry that is net hydrogen positive, with 1.5 moles of hydrogen being generated for every mole of methane consumed. The outflow stream thus contains a mixture of hydrocarbons, including the desirable product acetylene, along with a predominance of hydrogen. In embodiments, this hydrogen can be separated from the outflow stream, for example by using a membrane separator to separate the hydrogen from the remainder of the effluent. After separation, hydrogen can be purified and commercialized as a separate gas product; alternatively, or in addition, hydrogen can be, in whole or in part, recycled into the system, as illustrated in previous Figures. In other embodiments, acetylene can be separated from the outflow stream instead of or in addition to hydrogen separation. For example, acetylene can be absorbed in an absorption column and then desorbed and collected. In an embodiment, the outflow stream from the reactor can first be treated to remove particulate carbon and condensates, and then acetylene can be removed. After the acetylene is removed, the hydrogen can be optionally removed, captured, or recycled.

As the outflow stream leaves the plasma reaction chamber, it contains a combination of gases, volatilized higher-order hydrocarbons, and particulate carbon. As previously described, the particulate carbon can be filtered out immediately downstream from the reactor chamber. In embodiments, the outflow stream can subsequently be passed through a cold trap in order to remove certain higher-order hydrocarbons from the outflow stream as condensates. After passing through the cold trap, the outflow stream can be further separated. For example, other higher-order hydrocarbons can be removed from the outflow stream as described below. These compounds are typically deemed waste products, and they can be discarded or disposed of after their removal. Following or simultaneously with the removal of higher-order hydrocarbons, acetylene and hydrogen are separated from the outflow stream via the effluent separation and disposal subsystem. The separation process proceeds using one or more separation technologies, such as adsorption technologies, absorption technologies, chemical reaction technologies such as oxidization or catalyst-mediated conversion, and the like.

i. Adsorption

In certain embodiments, for example, the outflow stream can be passed through an adsorption column, where the column contains a high surface-area adsorbent material that can selectively remove acetylene or higher-order hydrocarbons from the outflow stream flowing therethrough. In embodiments, adsorbent material can include appropriately sized materials such as activated carbon, zeolites, silica aerogels, molecular sieves, metal-organic frameworks (MOF s), coordination polymers, clays, diatomaceous earth, or pumice. The adsorbent material can be a powder or a film, or it can be formed into spherical pellets, rods, or other shapes which may be useful. These adsorbent materials can be modified by calcination at elevated temperatures, ion-exchange, or doping with molecules that increase adsorption affinity or capacity. Additionally, a combination of two or more adsorbent materials can be used to take advantage of multiple physical properties. The adsorbent materials can be contained within a single adsorbent column or divided into multiple adsorbent columns to trap different impurities from the outflow stream in distinct locations. Advantageously, adsorbent materials can be selected to minimize product loss as the outflow stream passes through the adsorbent column: in some instances, higher-order hydrocarbon impurities have a higher affinity for the adsorbent material than does the desired product; in other instances, the impurities can displace the product molecules off the surface of the adsorbent. In either case, product loss is minimal.

Under certain circumstances, adsorbents can be disposed of after a single use if the capacity of the adsorbent and the concentration of impurities allows for sufficient impurities to be removed before disposal. Under other circumstances, for example if disposal is unfeasible for economic or logistical reasons, the adsorbent can be regenerated and re-used cyclically. Methods for regenerating the adsorbent include pressure reduction, solvent washing, heating, and displacement by another gas. During regeneration, the impurities can be desorbed off the surface of the adsorbent, or they can be converted in-situ to another chemical that is easier to desorb. If the impurities have been converted to an acceptable derivative molecule, this molecule can be desorbed in-line and released into the process stream. If the impurities are unaltered on the surface of the adsorbent, so that they cannot be released into the downstream flow, they can be diverted to a side stream to be vented, incinerated or collected for waste disposal. In embodiments, an automated system can arrange for alternation between or among multiple adsorber vessels, allowing for regeneration cycles in a continuous operation; such a system has been referred to in the art as a swing adsorber.

Adsorbers can be used for further separation of the outflow stream after the removal of higher-order hydrocarbons. Depending on the preferred mode of adsorption and desorption, a pressure swing adsorber (PSA), a vacuum swing adsorber (VSA), or a temperature swing adsorber (TSA) can be used. For example, in certain embodiments, the outflow stream can be fed into a PSA system in order to separate hydrogen gas from the outflow stream. In the PSA system, the outflow stream is pressurized and fed into an adsorption column in which all non-hydrogen components are adsorbed onto the adsorbent material. With all non-hydrogen materials removed from the stream a purified hydrogen exits the column. In embodiments, the feed for the PSA system can be the outflow stream from the plasma reactor, or it can be the collected gas from the first absorption column described above, or some combination thereof.

Or, for example, the outflow stream can be fed into a TSA system that is adapted for separating higher acetylenes from the outflow stream. As used herein, the term "higher acetylenes" refers at least to alkynes containing 3 and 4 carbon atoms, although it can also be applied to all gaseous alkynes and to gaseous aromatics. Through use of a TSA system, higher acetylenes can be separated significantly, even completely, from an acetylene stream without acetylene loss. In embodiments, the higher acetylene molecules can displace acetylene on the surface of an adsorbent, allowing for extreme selectivity in separating the higher acetylenes from the acetylene stream. In order to accomplish this, the adsorption process advantageously is terminated before the higher acetylenes are themselves displaced by an even heavier molecule like benzene. Therefore, the adsorption cycle in the TSA should be tuned to allow the higher acetylenes to be adsorbed and retained on the adsorbent surface, but to prevent the higher acetylenes from being displaced. Thus, before the higher acetylenes are displaced off the adsorbent surface, the reactor is closed off to the process stream. The adsorbent can then be disposed of and replaced, or alternatively, regenerated. In regeneration, the outflow stream is diverted from the adsorber, and hot air (for example, >300° C. or >350° C.) is passed over the adsorbent bed. Alternatively, the regeneration can be conducted with hot nitrogen or some mixture of air and nitrogen. In embodiments, the gas temperature can be between 120° C. and 350° C. The regeneration gas mixture and the temperature can be varied over the course of the regeneration. Regeneration can also be performed while the adsorber bed is being actively cooled either in certain sections or in its entirety. The locations and amount of optional cooling can also be varied over the course of regeneration. The impurities are released from the adsorbent and either vented or burned. In some iterations, multiple vessels can be used for a continuous operation in which some vessels are adsorbing while others are regenerating.

Adsorber vessels can be covered in an insulating material to maintain an elevated temperature during either operations and/or regeneration. The adsorber design can include many aspects known by those of ordinary skill in the art. For controlling the process and regeneration gas flows, internals devices such as spreaders, distributors, tubes, channels, plates, screens, and the like can be used. Additional internals devices can be used to control the adsorbents locations and/or performance, such as screens, supports, and other packing materials. Additionally, internal objects to improve heat transfer can be used, including materials with higher heat conductivity in a variety of physical shapes, such as rods, tubes, wires, balls, and the like. In embodiments, the amount of filler materials can be anywhere from 0 to 50% of the adsorber volume. Further, adsorbers can include designs and/or systems to actively cool the bed, e.g., tube and shell designs.

In another embodiment, the TSA can be modified to remove carbon dioxide and hydrogen sulfide in addition to higher acetylenes. By operating the TSA under pressure, the adsorbent can simultaneously remove carbon dioxide, hydrogen sulfide, higher acetylenes and aromatic mixtures (e.g., mixtures of benzene, toluene, and xylene isomers, collectively referred to as BTX). This can be achieved by operating the TSA at pressures higher than 5 barg. Other arrangements allowing selective removal of impurities would be readily envisioned by skilled artisans. For example, certain impurities such as $CO_2$ and/or BTX can be removed by a dedicated removal system before the gas stream is directed to the TSA, with the TSA's operating parameters being tuned to remove the residual impurities. Impurities in the gas stream such as alcohols (methanol, ethanol, butanol, and the like), sulfides and mercaptans, acetones and other small ketones, water, ammonia, carbon monoxide and carbon dioxide, oxygen, and the like, can be removed by the temperature swing adsorption process with the adjustment of the TSA parameters and/or with the addition of pressure.

In certain embodiments, the adsorption process can be modified so that acetylene and hydrogen can be separated through the temperature swing adsorption mechanism by modifying the timing of the temperature swing adsorption process or by modifying the amount of adsorbent in the TSA. In embodiments, compared to the adsorption period for a similarly sized adsorber that separates acetylene from higher acetylenes, the adsorption period for separating hydrogen and acetylene is shorter, and may be termed "short-cycle temperature swing adsorption." By exposing the gas stream to temperature swing adsorption during this abbreviated amount of the entire TSA cycle, the short-cycle temperature swing adsorption process separates hydrogen from a mixture of acetylene and higher acetylenes. Short-cycle temperature swing adsorption is, accordingly, especially advantageous if its product, a mixture of acetylene and higher acetylenes, is desirable. The cycling for short-cycle temperature swing adsorption can be understood in more detail as follows: if the length of the entire temperature swing adsorption cycle (from initiation of adsorption to commencement of adsorber regeneration) is $T_x$, a limited period of time at the beginning of the adsorption cycle $T_1$ can be dedicated to separating acetylene and its entrained higher acetylenes from the hydrogen stream, with the TSA remaining offline during the remainder of the adsorption cycle $T_2$, where $T_2=T_x T_1$. This adjusted adsorption schedule for short-cycle temperature swing adsorption employs the first portion of the overall adsorption cycle $T_1$ for separating acetylene and entrained higher acetylenes from hydrogen, with $T_1$ ranging in length to occupy the first 10% to 25% of the entire cycle $T_x$. To employ short-cycle temperature swing adsorption, a TSA system as described above is operated for the first part of its cycle $T_1$ to remove the acetylene and higher acetylenes from the gas stream, allowing hydrogen to pass through. The TSA system is then offline during the remainder of its cycle, $T_2$. Regenerating the TSA adsorbent at the end of $T_2$ will prepare the TSA for another separation cycle.

While the TSA can be used for either a short cycle or a regular cycle of temperature swing adsorption following its regeneration at the end of $T_2$, an alternation of short-cycle and regular cycle temperature swing adsorption using the same TSA device may not be advantageous. Instead, a single TSA device can be dedicated to the short-cycle process; in such a dedicated device, regenerating the TSA adsorbent at the end of $T_2$ prepares the device for another cycle of separating acetylene and higher acetylenes from hydrogen, i.e., short-cycle temperature swing adsorption. The short-cycle temperature swing adsorption process allows acetylene and admixed higher acetylenes to be removed from the gas stream while the hydrogen passes through the TSA, following which hydrogen and acetylene mixture can be processed separately after their passage through the TSA device. As an alternative to varying the duration of the adsorption cycle, as described above, a comparable separation can be achieved by increasing the amount of adsorbent in the TSA device without changing the time frame for exposure to the gas stream, or in concert with changing the time frame for exposure to the gas stream.

As mentioned above, short-cycle temperature swing adsorption separates acetylene, along with higher acetylenes that accompany the acetylenes, from the incoming gas stream. The product produced by short-cycle temperature swing adsorption is thus acetylene in combination with the higher acetylenes. In contrast, the standard TSA separates higher acetylenes from the gas stream, leaving behind a mix of hydrogen and acetylene that will need to be further separated into a hydrogen fraction and a purified acetylene fraction. In contrast to the short cycle temperature swing adsorption process, the standard cycle TSA is offline during the initial part ($T_1$) of the cycle having a time duration $T_x$, and operates during the latter part of the cycle $T_2$; the regular cycle TSA is online during a period that corresponds approximately to the time that the short cycle TSA would be offline. As with the short-cycle TSA, the standard-cycle temperature swing adsorber would commence adsorbent regeneration at the end of the cycle time $T_x$, but in contrast to the short-cycle TSA, the standard cycle TSA would remain offline during the first quarter of the cycle ($T_1$).

For certain uses, the separation of acetylene and higher acetylenes from the residual hydrogen, as carried out by the short-cycle TSA step, yields a commercially acceptable output product. For example, in torch applications, as described in more detail below, it can be acceptable to include the higher acetylenes in the acetylene output product, and the simple separation of the acetylene/higher acetylene mix from residual hydrogen is commercially acceptable. In such applications, a short-cycle TSA can be used as a single stage to separate acetylene-plus-higher-acetylenes output product from the residual hydrogen stream. For other uses, a substantially pure acetylene product is desirable, wherein the higher acetylenes have been removed from the acetylene output product. For these purposes, and the use of the short-cycle temperature swing adsorption can be combined with a standard-cycle temperature swing adsorption in a multistep process. For example, standard-cycle temperature swing adsorption can remove the higher acetylenes from the gas stream as it passes through a first TSA, and then the outflow from the first TSA (such outflow still a mixture of hydrogen and acetylene but with higher acetylenes removed) can be directed into a second TSA that uses short-cycle temperature swing adsorption to separate the purified acetylene from the gas stream, allowing the hydrogen to pass through. While other separation mechanisms (absorption, membranes, etc.), can be used with the short-cycle TSA to remove higher acetylenes from the short-cycle adsorption product, the use of the short-cycle TSA in combination with the standard-cycle TSA can offer an advantageous alternative to using the standard-cycle TSA in combination with membrane-based separation technologies that require pressurizing the gas flow to pass through membranes to effect acetylene/hydrogen separation. In other embodiments, a TSA such as a standard TSA or a short-cycle TSA can be implemented in keeping with the following parameters. In a TSA system with a given adsorbent, volume, temperature, pressure, flow rate, influent composition, and other characteristics that are constant or are given functions of time, the period of time for capturing a specific gas A by the TSA can be termed $T_c(A)$, or the "capture period" for Gas A. In other words, $T_c(A)$ (the capture period for Gas A) is the time between the moment the bed is brought online to the moment just before gas species A reaches an unacceptable concentration in the outflow gas stream. In a short-cycle TSA that is designed to capture acetylene, for example, the capture period of acetylene would be $T_c$ (acetylene) or $T_c$ ($C_2H_2$). For a standard TSA, the first species to be captured is the higher acetylene species, Gas B, that is first to appear in the outflow gas stream; its capture period is termed $T_c(B)$. For the standard TSA, the bed must be taken offline and replaced or regenerated after $T_c(B)$. Similarly, for the short-cycle TSA designed to separate acetylene from the remainder of the gas stream, it must be taken offline and regenerated or replaced after $T_c(C_2H_2)$.

In cases where it is advantageous to have a standard TSA in series before a short-cycle TSA, it may also be advantageous to design the adsorbent beds for each device such that $T_c(B)$ for the standard TSA is equal in duration to $T_c(C_2H_2)$ for the short-cycle TSA. When the adsorbent beds are designed at these aligned scales, the short-cycle TSA can be exposed to a consistent amount of acetylene in each cycle.

In embodiments, the cycle timing for the standard TSA in series before a short-cycle TSA can be arranged as follows. For the standard TSA, the acetylene is being captured throughout $T_c(C_2H_2)$. Then, through $T_r$, the period after the conclusion of $T_c(C_2H_2)$ but before the conclusion of $T_c(B)$, the acetylene is being desorbed from the standard TSA as it is displaced by higher acetylenes which continue to be adsorbed. During $T_c(C_2H_2)$ therefore, the gas that exits the standard TSA is devoid of both acetylene and higher acetylenes. During $T_r$, the gas that passes through the standard TSA is enriched in acetylene but still devoid of higher acetylenes. During this time period $T_r$, the amount of acetylene in the outflow stream from the standard TSA is greater than the amount entering the standard TSA because the acetylene being replaced by higher acetylenes on the standard TSA adsorbent bed is being added to the outflow stream. The total amount of acetylene that flows to into the standard TSA adsorption bed over $T_c(B)$ flows out through the standard TSA outflow stream over the shorter duration $T_r$. The short-cycle TSA therefore is not adsorbing acetylene during the standard TSA's $T_c(C_2H_2)$, because the acetylene is being adsorbed by the standard TSA. During $T_r$, the acetylene exiting the standard TSA reaches and is adsorbed onto the short-cycle TSA. If the short-cycle TSA has been sized properly to have an acetylene saturation time that meets or exceeds $T_c(B)$, the standard TSA's higher acetylene capture period, the gas that passes out of the short-cycle TSA will be devoid of both acetylene and higher acetylenes for the entirety of its active period, that is, the standard TSA's $T_c(B)$. At the end of this active period, both vessels can be taken offline and replaced by fresh vessels and/or regenerated.

In certain embodiments, the stream being processed in a standard or short-cycle TSA may contain a wide variety of products that have weak affinity for the adsorption medium and as such pass readily through to the outflow gas along with the hydrogen. Such weak-affinity gases that may be present in the hydrogen-rich outflow gas include methane, nitrogen, carbon dioxide, and low mass alkane and alkene species. In such cases, the standard TSA will separate higher acetylenes from an outflow gas mixture of acetylene and gases with weak affinity for the adsorbent, and the short-cycle TSA will separate acetylene and higher acetylenes from gases with weak affinity. As a general set of principles, the standard TSA can be used if the desired outflow gas is to comprise a mixture of acetylene and gases with a weak affinity for the adsorbent, while the short-cycle TSA can be used if the desired outflow gas is only to comprise gases with weak affinity for the adsorbent. In order to separate acetylene from higher acetylenes and from gases having a weak affinity for the adsorbent, the standard TSA can be used in combination with the short-cycle TSA, for example with the two in series, standard TSA followed by short-cycle TSA.

A variety of adsorption strategies can be implemented to separate acetylene with the ideal mixture of impurities for hydrogen and acetylene black production, torch gas production, or another application that tolerates or demands an impure stream. These strategies can include the partitioning and recombination of gas streams desorbed from or passing through one or more separation modules.

Partitioning, for example, can be done based on gas flow, adsorbent temperature or pressure, or time online. The composition of the gas captured by the adsorbent is variable based on the temperature, pressure, the period the bed is on-line, the type of adsorbent, and other factors. During regeneration, therefore, the composition of the gas stream released from the adsorbent bed changes as it is heated or depressurized over time. The composition of the released gas can be further controlled by splitting the gas based on the temperature and pressure of the adsorbent when the gas was released.

To accomplish gas separation using this technique, a TSA bed being regenerated is heated over time. The adsorbent bed first releases a hydrogen-rich gas mixture near the starting temperature. Next, nearly pure acetylene is desorbed at moderate temperatures. As the temperature rises further, a mixture of acetylene and higher acetylenes is released from the adsorbent. Finally, heavier compounds remain and must be liberated with the help of hot air as a regeneration gas. This TSA bed has the first portion of released gas (i.e., the hydrogen-rich gas mixture) directed to the active TSA bed to be reprocessed. The second portion of released gas, pure acetylene, can be used as feedstock for chemical processes and the like, as described below in more detail. The third portion, comprising acetylene and higher acetylenes, can be directed to a reactor for conversion into hydrogen and acetylene black, as described below in more detail. The fourth portion, comprising heavier compounds, can be removed with air and vented, restoring the adsorbent to its initial state.

ii. Absorption

In certain embodiments, the outflow stream can be passed through an absorption column, wherein a solvent at an optimized flow rate running counter-current to the outflow stream preferentially absorbs higher-order hydrocarbons from the flowing outflow stream instead of absorbing the desired gas product like acetylene. The higher-order hydrocarbons can then be separated from the solvent in a second column, and the solvent is returned to the absorption column. Examples of solvents with stronger affinity for higher-order hydrocarbons over the desired gas product include methanol, ammonia, toluene, benzene, kerosene, butyrolactone, acetonitrile, propionitrile, methoxypropionitrile, acetone, furfural, N,N-dimethylformamide, N,N-diethylformamide, N,N-dimethylacetamide, N,N-diethylacetamide, N-formylmorpholine, and N-alkylpyrrolidones, for example N-methylpyrrolidone (NMP).

In other embodiments, the outflow stream can be passed through an absorption column, wherein a solvent having a strong affinity for acetylene and preferably running countercurrent to the outflow stream, absorbs acetylene from the flowing outflow stream. The absorbed acetylene can be removed from the solvent by heating the solvent in a second column for restoring the solvent, and the restored solvent then can be returned to the absorption column. Examples of solvents with stronger affinity for acetylene over other outflow gases include methanol, ammonia, toluene, benzene, kerosene, butyrolactone, acetonitrile, propionitrile, methoxypropionitrile, acetone, furfural, N,N-dimethylformamide, N,N-diethylformamide, N,N-dimethylacetamide, N,N-diethylacetamide, N-formylmorpholine, and N-alkylpyrrolidones, e.g., N-methylpyrrolidone (NMP).

iii. Chemical Reactions

In certain embodiments, higher-order hydrocarbons in the outflow stream can be oxidized and thereby removed from the outflow stream. For example, certain higher-order hydrocarbons, particularly diacetylene and substituted acetylenes such as methylacetylene and vinylacetylene, can be difficult to separate from acetylene, and they can be removed by converting them into non-acetylenic compounds. To accomplish this, the outflow stream can be passed through a column or vessel containing an oxidizing agent, such as a concentrated liquid acid capable of acting as an oxidizing agent, such as nitric acid, sulfuric acid, phosphoric acid, and the like. The higher-order hydrocarbons such as diacetylene and the substituted acetylenes can react with the oxidizing agent or concentrated acid to create other hydrocarbon compounds that can be more easily separated from the outflow stream. In certain embodiments, the outflow stream can be contacted with phosphoric acid on a solid support to convert the higher-order hydrocarbons such as diacetylene and the substituted acetylenes into other hydrocarbon products that can be more easily separated from the outflow stream.

In certain embodiments, the outflow stream can be passed through a catalyst bed, using a catalyst that comprises transition metals, transition metal oxides, transition metal salts, or zeolites, in order to convert various higher-order hydrocarbons into other carbon species that are more readily removable from the gaseous product stream. When exposed to a suitable catalyst, these higher-order hydrocarbons can be converted into a more easily removable compound by catalyst-driven mechanisms such as polymerization, oxidation, hydrogenation, and disproportionation. Depending on the mechanistic mode of catalytic conversion and the products obtained, these derivatives of the higher-order hydrocarbons can be removed through further downstream processes such as are described herein.

iv. Other Separation Technologies

In certain embodiments, higher-order hydrocarbons can be removed from the outflow stream by using a condenser, whereby the condenser collects these compounds on a high-surface-area material such as silica gel, activated carbon, activated alumina, zeolites, and the like. For example, certain higher-order hydrocarbons, e.g., methylacetylene and vinylacetylene, can be difficult to separate from acetylene in gaseous form, but their condensation points (5.01° C. and 10.3° C. respectively) contrast to the condensation point of acetylene (−84° C.) making them suitable for removal via condensation from the outflow stream. In this embodiment, a cold bed containing high surface area material at temperatures between −84° C. and 10° C. can effectively condense out higher-order hydrocarbons from the outflow stream.

In certain embodiments, the outflow stream can be passed through a gas separation membrane system, wherein gas molecules are separated via size exclusion. For example, smaller molecules, such as hydrogen, will preferentially flow through the membrane element, forming a permeate stream, while larger molecules, such as methane, acetylene, higher-order hydrocarbons, nitrogen, carbon dioxide, and any other larger molecules, do not flow through the membrane (depending on the porosity of the membrane), forming a retentate stream. In certain embodiments, the permeate steam is a hydrogen-enriched stream and the retentate stream is a hydrogen depleted stream. Gas separation membrane elements can be formed from a variety of substances, for example: hollow fiber polymer membranes where the polymer can be polycarbonate, polyamide, or cellulose acetate; inorganic membranes where the inorganic material can be mesoporous silica, zeolite, a metal-organic-framework, or mixed metal oxides; metal membranes where the metal can be palladium or palladium-silver alloys; and the like. In embodiments, the feed for the membrane separation system can be the outflow stream from the plasma reactor, or it can be the collected gas from the first absorption column described above, or some combination thereof.

Following certain of these outflow separation measures, in embodiments, the outflow stream, containing acetylene, hydrogen, and higher-order hydrocarbons, can be further separated into its components so that the desired gaseous products can be retrieved. In other embodiments, the outflow stream is not subjected to further separation, for example if it is to be used for further chemical processing, or if it is provided to a customer or end-user as a mixed stream.

f. Data Management and Safety Subsystems

Advantageously, the overall gas production system comprises interconnected data management subsystems and safety subsystems, so that the safety measures incorporated in these systems and methods are informed by data collected about the system's performance. In embodiments, data management can include devices, procedures and algorithms for data collection and performance diagnosis, and storage facilities for recording and preserving data. In embodiments, performance diagnosis includes monitoring the state of the system within normal parameters to facilitate overall integration and control, and identifying signs of upcoming or active failure states. Optical diagnostics can be directed at surveillance of the plasma region, for example visible light cameras, mid-IR pyrometers, broadband spectrometers, and the like. Apparatus diagnostics can include pressure transducers, thermocouples, flow meters, microwave power sensors, and the like. Other diagnostic equipment can be used as appropriate, for example full-scale spectrometers and oscilloscopes. In embodiments, various diagnostic modalities can be integrated and monitored automatically and/or manually during a run.

In embodiments, the manual and automatic diagnostic procedures can be integrated with safety procedures, which can include a fault-interlock system. In an embodiment, diagnostic input can be actively monitored by hardware and software. If an anomaly is detected, a fault signal can be triggered that activates a predetermined response pattern. For those most serious faults, such as a sudden corroborated pressure spike, an immediate automated "hard" shutdown can be triggered. For faults of moderate severity, where the consequences are less serious, a slower automated shutdown can be triggered, intended to stop operations over the course of several seconds. For those faults where a parameter is outside the expected range, but no major consequences are anticipated, the operator can be alerted, so that appropriate actions are taken to rectify the situation and clear the fault without requiring a system shutdown.

3. Exemplary Systems and Subsystems a. 100 kW-Powered Plasma-Based Hydrocarbon Processing System A plasma-based hydrocarbon processing system using plasma technology to transform hydrocarbon-containing inflow gas into acetylene and hydrogen can obtain a high degree of source hydrocarbon conversion in combination with a high degree of selectivity for the production of acetylene and/or hydrogen. The system described below uses a 100 kW power supply to generate the microwaves that form the plasma and effect the chemical transformations.

The central reaction of this process takes place when methane (derived, for example, from natural gas or biogas) or another $C_2$-$C_4$ source hydrocarbon is fed into a microwave-energized region, where it breaks down into a plasma. Without being bound by theory, it is postulated that the plasma drives the reaction from the source hydrocarbon to acetylene and hydrogen by decomposing the hydrocarbon into excited $CH_x$ radicals that recombine after the plasma energy state to form a spectrum of hydrocarbon products and hydrogen. Using a $C_2$-$C_4$ hydrocarbon as a feed improves the overall process efficiency as compared to methane, while a high degree of selectivity to acetylene can be maintained. However, using methane as contained in natural gas or biogas has the advantage of operational efficiency and cost-effectiveness.

The methane conversion process in the 100 kW-powered processing system (i.e., using methane as may be found in a natural gas or biogas feed or a pure methane feed) uses approx. 9.5 kWhr per kg of acetylene product formed, with an acetylene yield of 90%: for the feed gas employed, about 90% is converted to acetylene. The resulting product mix is influenced by the non-thermal nature of the plasma temperatures. The gas temperature is 3000-4000 K while the vibrational temperature and electronic temperatures are two to three times higher, pushing the reaction equilibrium to form acetylene with a high selectivity, and with abundant hydrogen as a byproduct. Hydrogen produced by the plasma reaction can be recycled back into this system as a secondary feed gas that is used for subsequent reactions, and/or it can be segregated as a separate gas product. The co-presence of hydrogen and hydrocarbon as components of the reaction reduces the reaction's production of solids. To achieve a desirable proportion of hydrogen and methane for the reaction, the system recycles the produced hydrogen to participate in the methane-based reactions, as described in more detail below.

i. Overall System

The 100 kW-powered plasma-based hydrocarbon processing system comprises four subsystems: gas delivery, microwave, vacuum, and cooling. The gas delivery subsystem contains two inflow lines. The first inflow line is a feed line conveying a mixed gas such as natural gas continuously sourced from a local utility company or such as upgraded biogas, comprising a mixture of predominantly methane, with small amounts of ethane, propane, carbon dioxide, and nitrogen (depending on the source of the raw mixed gas). This inflow can be scrubbed using conventional technologies before it enters the plasma reaction chamber, resulting in an almost pure methane stream, with other residual mixed gas components present on the order of about 100 ppm. The total flow from this inflow line is scalable with the overall microwave power of the system, with a flow of approximately about 3 SLM methane/kW microwave power. A second inflow line conveys recycled gas produced by the reactor that contains about 85 to about 90% hydrogen, with small amounts of methane and nitrogen, for example with amounts of unreacted nitrogen of about 5% to about 6%. The total flow from this inflow line is also scaled with the overall microwave power of the system, with a flow of about 5 SLM recycled gas/kW microwave power.

Each inflow stream is sent into the plasma reaction chamber through its own inlet that injects its flow into an entry region of a quartz tube to flow through the tube to the region in which the plasma is created. The inlet for each inflow stream can be angled by a gas injector device to produce the vortex flow that mixes the streams within the quartz tube as they flow towards the reaction region, i.e., the plasma reaction chamber. The flow of gas entering through each inlet is controlled by mass flow controllers, adjusted to create a hydrogen-to-methane molar ratio of $1.5H_2:1CH_4$. As the methane is transformed into plasma, a spectrum of reaction products is formed within the plasma reaction chamber within the quartz tube.

When methane is used as a feed gas, about 95% of the methane undergoes chemical change within the plasma. Acetylene accounts for 95% of the hydrocarbons produced from the plasma-energized reactions, giving an overall approximate 90% acetylene yield. Hydrogen is the other dominant reaction product from these reactions, accounting for approximately 80% of the total outflow stream by volume.

Figure 9:
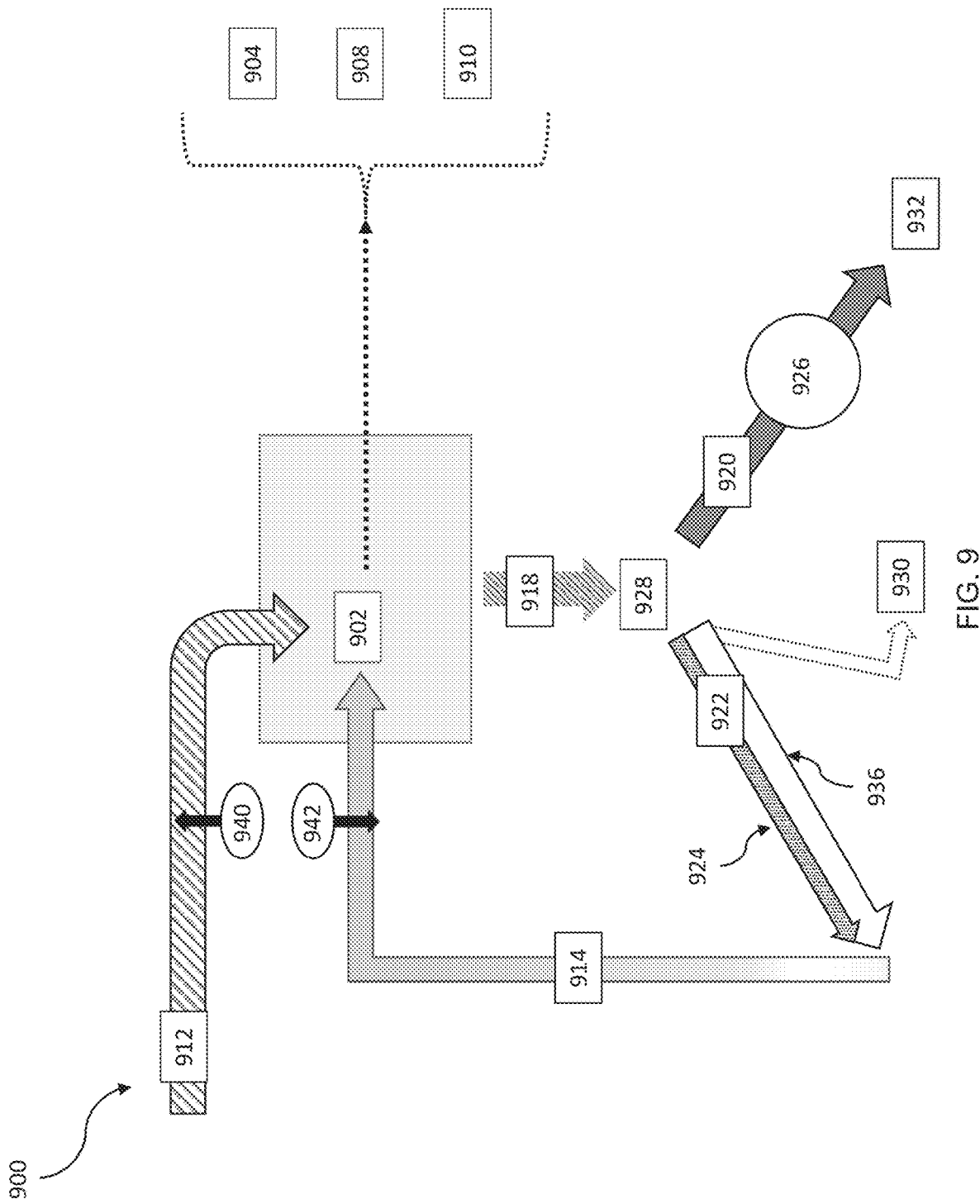
FIG. 9 is a block diagram of a plasma-based hydrocarbon processing system and related subsystems.

An exemplary 100 kW-powered plasma-based hydrocarbon processing system 900 is represented schematically by the block diagram shown in FIG. 9. As shown in this Figure, a central reactor 902, comprising an injection region 904, a reaction region 908, and an outflow region 910, receives two separate gas streams: (1) a feed gas 912 containing a source hydrocarbon (for example the methane in a mixed gas such as natural gas or biogas, or a single $C_1$-$C_4$ hydrocarbon, or a customized blend of $C_1$-$C_4$ hydrocarbons), and (2) a recycled gas flow 914 that includes hydrogen and mixed hydrocarbon-containing gas, and optionally unreactive nitrogen.

As schematically represented in the Figure, the inflow gas streams 912 and 914 are processed in the reactor 902 to form an outflow stream 918 that contains acetylene, hydrogen, and a small proportion of mixed hydrocarbons. The outflow stream 918 is then separated into its gaseous components via a gas separation system 928 (e.g., adsorption, absorption, or a combination thereof) to yield an acetylene stream 920 and a hydrogen-dominant gas stream 922 that contains hydrogen 936 and a mixture of hydrocarbons 924. Thus, diverted from the main outflow stream 918 by the gas separation system 928, the acetylene stream 920 can be purified via further sequestration of impurities in a purification system 926 to yield a purified acetylene gas product 932. Once the acetylene component 920 has been removed from the outflow stream 918, the remaining gas stream 922 is predominantly hydrogen along with a mixture of hydrocarbon reaction products, i.e., is hydrogen-dominant. This hydrogen-dominant gas stream 922 can be subjected to further separation if desired, so that hydrogen gas is isolated as a distinct gas stream 930. The hydrogen gas product stream 930 can be further purified as necessary and sold as a product, or it can be recycled back into the reactor 902 for further reaction with the feed gas 912. In this system 900, instead of recycling the hydrogen gas product stream 930, the mixed hydrogen-dominant gas stream 922 is recycled to form the recycled gas flow 914, which is reintroduced into the reactor 902 for further reaction with the feed gas 912. Mass flow controllers 940 and 942 coordinate the inflow of the feed gas 912 and recycled gas 914 into the reactor 902 to create the desired ratio of hydrogen to methane (or hydrogen to other source hydrocarbon) in the reactor 902.

ii. Reactor

Figure 10:
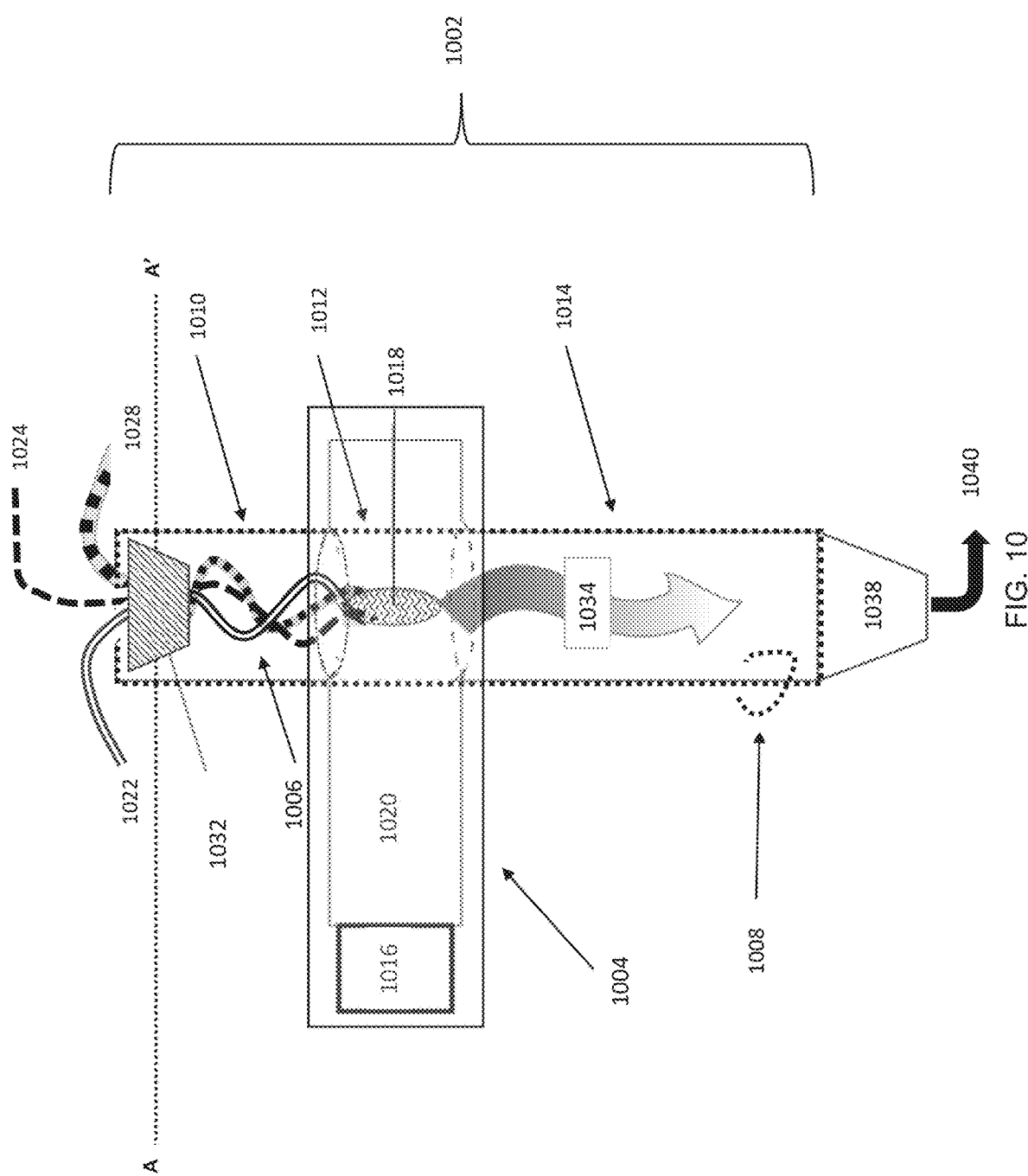
FIG. 10 is a schematic diagram of a reaction chamber and its components.

The reactor identified in FIG. 9 is shown in more detail in FIG. 10. FIG. 10 depicts schematically the reactor 1002, its components, and its integration with the microwave subsystem 1004. As depicted, and as outlined by the grey shadowed box, the microwave subsystem includes a power supply and magnetron complex 1016 for producing the microwaves, and a waveguide assembly 1020 for guiding the microwaves towards a reaction region 1012 within the quartz tube where the microwave plasma 1018 is formed. As shown in FIG. 10, a quartz tube 1008 contains the components of the reactor 1002: the injection region 1010, the reaction region or reaction chamber 1012, and the outflow region 1014. Within the quartz tube 1008, the microwave plasma 1018 is generated by the microwaves (not shown) aimed at the gas flow 1006 within the tube 1008, thereby effecting the transformation of source hydrocarbon into hydrogen and various hydrocarbon-derived products. This quartz tube 1008 is inserted through the broad wall of a microwave waveguide assembly 1020. The size of the quartz tube 1008 depends on the amount of microwave power used in the system. For the depicted system using 100 kW of power to produce microwaves, the quartz tube 1008 has an 80 mm outer diameter, a 75 mm inner diameter, a length of 1700 mm, and is maintained at a pressure of about 70 Torr by downstream vacuum pumps (not shown). The relationship of the quartz tube 1008 and the microwave subsystem 1004 is described below in more detail.

As shown in FIG. 10, the recycled gas stream 1022 mixes with the feed gas stream 1024 within the injection region 1010 of the reactor 1002, each stream entering the injection region 1010 of the reactor 1002 through its own inlet (not shown). The passage of each gas stream through the gas injector device 1032 (also shown schematically in FIG. 11) into the reactor 1002 affects its direction, flow rate, and velocity. As depicted in FIG. 10, an optional gas stream or gas streams 1028 can be directed into the injection region 1010, to be blended with the recycled gas stream 1022 and the feed gas stream 1024 to create a vortical gas flow 1006. After mixing, the gases in the gas flow 1006 flow distally through the quartz tube 1008, to encounter microwave energy produced by the power supply and magnetron complex 1016 and delivered through the waveguide assembly 1020 into the reaction region 1012 of the reactor 1002. The interaction of the microwave energy and the gas within the reaction region 1012 of the reactor 1002 produces the plasma 1018. The outflow gaseous stream 1034 containing the reaction products emerges from the plasma 1018 to enter the outflow region 1038 of the quartz tube 1008, to be passed out of the reactor 1002 for further separation 1040. As shown in this Figure, a microwave subsystem 1004 includes the power supply and magnetron complex 1016 and the waveguide assembly 1020; not shown in this Figure are additional elements of the microwave subsystem that are illustrated and described in the Figures below.

Figure 11A:
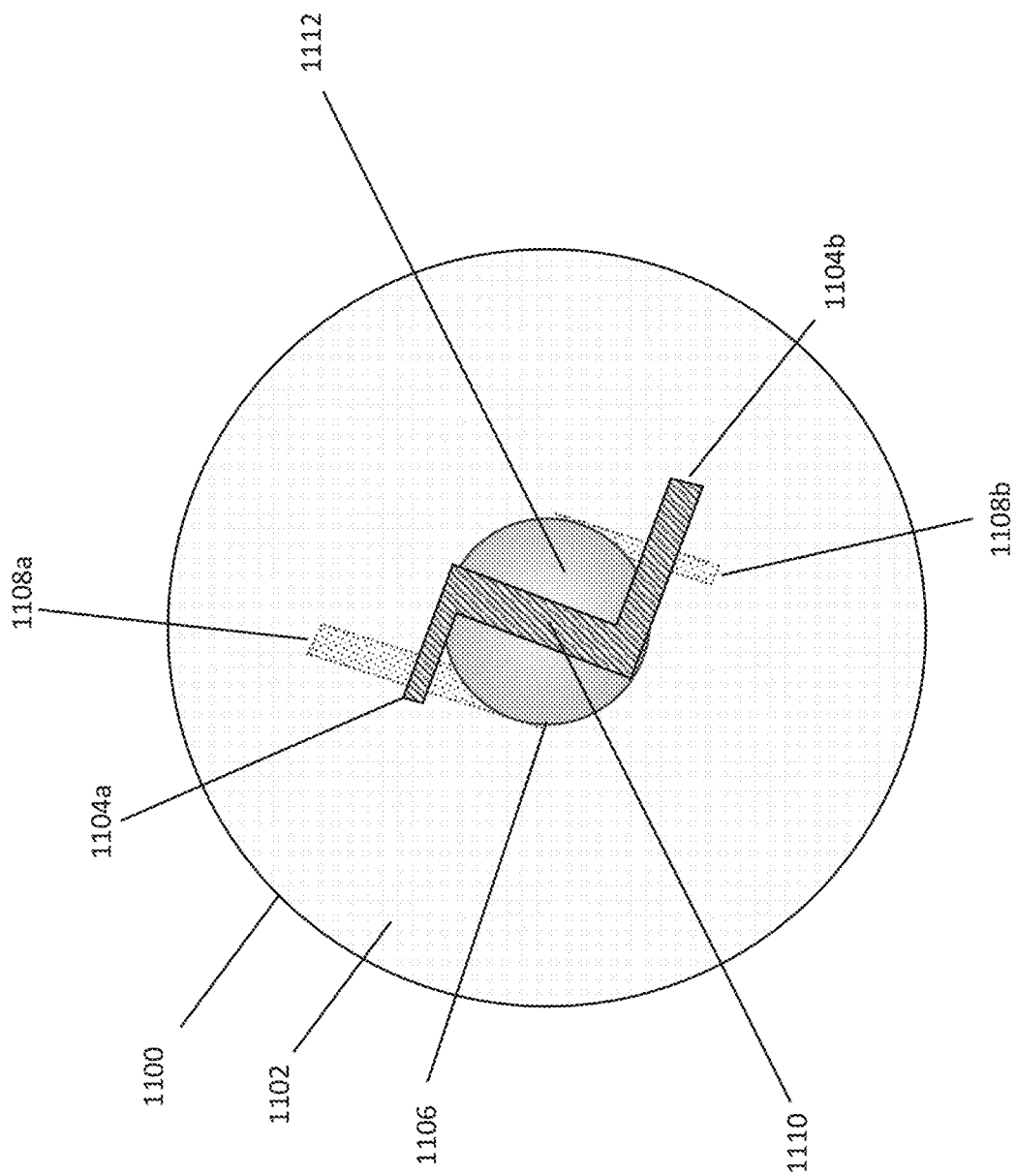
FIG. 11A is a schematic diagram of a gas injector in cross-section.

FIG. 11A is a cross-sectional schematic view (not to scale) of an embodiment of a gas injector suitable for use with the 100 kW-powered plasma-based hydrocarbon processing system, such as the gas injector 1032 depicted in FIG. 10. For exemplary purposes, the cross-sectional view in FIG. 11A corresponds to a cross-section taken at the line A-A' in FIG. 10. FIG. 11A shows a gas injector 1106 situated in a reaction chamber 1102 of a plasma reactor 1100 and providing a plurality of gas flows into the reaction chamber 1102 for those gases to encounter microwave energy as described above. As shown in this Figure, the gas injector 1106 provides flow paths for two distinct gas streams into the reactor 1102, with each gas stream directed through its own nozzle and flow path within the gas injector device 1106 and into the reactor 1102. As illustrated in FIG. 11A, there are four injector ports, two for the recycled gas flow 1104a and 1104 b, and two for the feed gas stream 1108a and 1108b. In the Figure, the two recycled gas nozzles 1104a and 1104b are in fluid communication with a first central flow channel 1110 through which the recycled gas stream enters the gas injector 1106 and is directed to the recycled gas nozzles 1104a and 1104b. Similarly, there is a second centrally-disposed channel 1112 in the gas injector 1106 for feed gas, where this channel is discrete from the first central flow channel 1110 for the recycled gas stream. There are two nozzles for feed gas 1108a and 1108b, in fluid communication with the second centrally-disposed channel 1112, with these nozzles 108a and 1108b entering the reactor 1102 at a different level than the nozzles for the recycled gas 1104a and 1104b. The nozzles for both types of gas flow are oriented in directions that are conducive for the formation of a vortex gas flow within the reactor 1102. The channel for recycled gases 1110 and the channel for feed gas 1112 do not intersect with each other, but rather provide separate gas streams into their respective nozzles 1104a/1104b and 1108a/1108b; neither do the nozzles intersect with each other, but rather provide their gas streams separately into the reactor 1102. The gas flow through each of the nozzles can be coordinated with the other gas flows in the other nozzles in terms of flow rate, path length, and pressure drop.

It would be understood by skilled artisans that the relative position of the feed gas channel 1112 and the recycled gas channel 1110 can be rearranged, for example, as parallel channels, as helices, at different levels within the gas injector 1106, or as other arrangements besides those shown in FIG. 11A, provided that the channels for each gas are kept separate from each other in the gas injector 1106, and further provided that each distinct gas stream enters the reactor 1102 through its own discrete nozzle or nozzles. Moreover, the number, configuration, and direction of the nozzles can be varied, provided that the gas stream for each component gas (i.e., feed gas and recycled gas and any optional additional gas) enters the reactor through its own nozzle, without commingling with the other gas stream.

Figure 11B:
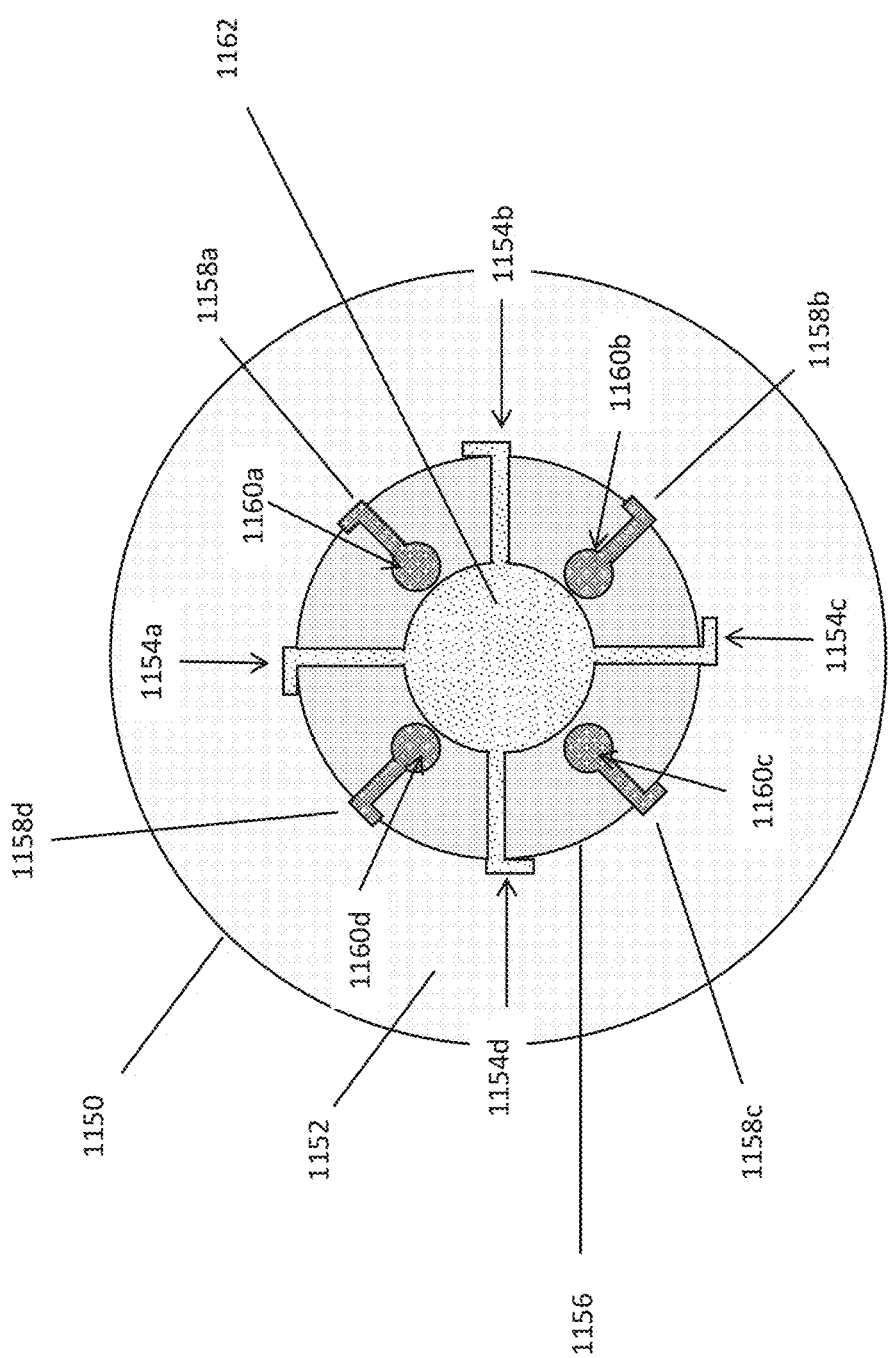
FIG. 11B is a schematic diagram of a gas injector in cross-section.

FIG. 11B is a cross-sectional schematic view (not to scale) of another embodiment of a gas injector suitable for use with the 100 kW-powered plasma-based hydrocarbon processing system, such as the gas injector 1032 depicted in FIG. 10. For exemplary purposes, the cross-sectional view in FIG. 11B corresponds to a cross-section taken at the line A-A' in FIG. 10. FIG. 11B shows a gas injector 1156 situated in a reaction chamber 1152 of a plasma reactor 1150 and providing a plurality of gas flows into the reaction chamber 1152 for those gases to encounter microwave energy as described above. As shown in this Figure, the gas injector 1156 provides flow paths for two distinct gas streams into the reactor 1152, with each gas stream directed through its own set of nozzles within the gas injector device 1156 and into the reactor 1152. As illustrated in FIG. 11B, there are eight injector ports or nozzles, four (1154a, 1154b, 1154c, and 1154d) for a first gas flow, for example the recycled gas flow, and four (1158a. 1158b, 1158c, and 1158d) for a second gas flow, for example a feed gas stream. In the Figure, the four nozzles for the first gas flow (1154a, 1154b, 1154c, and 1154d) are in fluid communication with a central flow channel 1162 through which the first gas stream enters the gas injector 1156 and is directed to the appropriate nozzles 1154a, 1154b, 1154c, and 1154d. The nozzles 1158a, 1158b, 1158c, and 1158d for the second gas flow are each supplied by a separate flow channel 1160a, 1160b, 1160c, and 1160d respectively. Other arrangements of the flow channels to supply the nozzles 1158a, 1158b, 1158c, and 1158d for the second gas flow can be envisioned, provided that the flow channels for the second gas flow do not permit the second gas flow to be commingled with the first gas flow. Instead, each gas flow is conveyed with its own discrete set of nozzles and its own flow channel(s). The nozzles for the first gas flow 1154a, 1154b, 1154c, and 1154d, and the nozzles for the second gas flow 1158a, 1158b, 1158c, and 1158d, are oriented in directions that are conducive for the formation of a vortex gas flow within the reactor 1152. The gas flow through each of the nozzles can be coordinated with the other gas flows in the other nozzles in terms of flow rate, path length, and pressure drop.

iii. Microwave Subsystem

Figure 12:
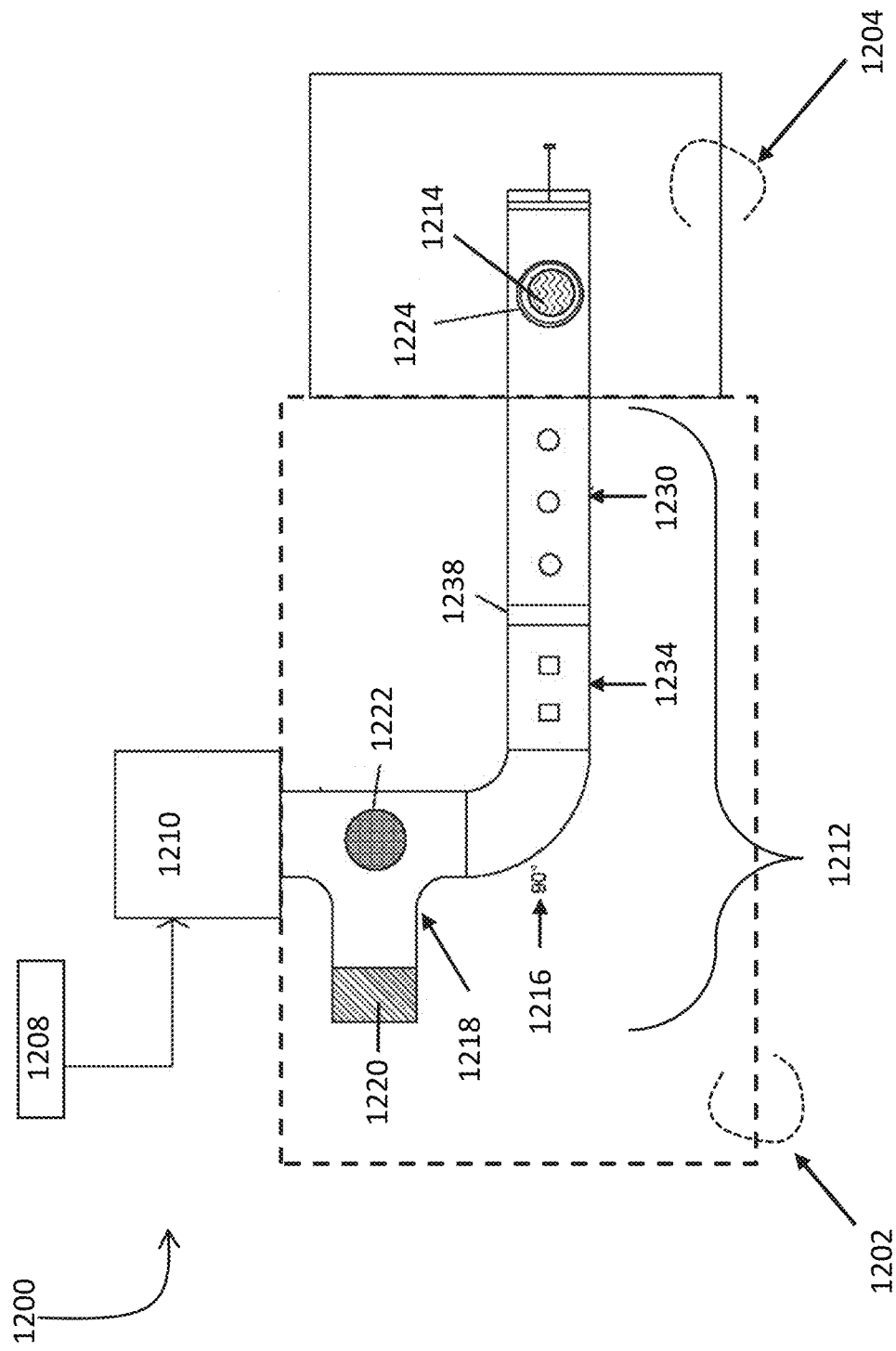
FIG. 12 is a schematic diagram of a microwave subsystem.

The microwave subsystem shown in FIG. 10 is depicted schematically in FIG. 12, and in more detail. Referring to FIG. 10, a reaction region 1012 of the reactor 1002 can be seen intersecting with the waveguide assembly 1020, wherein the microwaves are directed at the gas flow 1006 as it enters the reaction region 1012 to form the plasma 1018. The microwave subsystem 1004 is responsible for generating the microwaves and directing them towards the reactor 1002.

The microwave subsystem is shown in more detail in FIG. 12. As shown in this Figure, the microwave subsystem 1200 comprises a power supply 1208, a magnetron 1210, a waveguide assembly 1202 (which includes a waveguide 1212 and certain other standard microwave components as described below), and an applicator 1204. The power supply 1208 converts 480V, 150 A AC electrical power to 20 kV21 kV, 5.8 A of low-ripple DC power with a conversion of 96% to energize the magnetron 1210. The magnetron 1210, rated at 100 kW, produces continuous microwave power at 83-89% efficiency. The microwaves produced are in the L-band frequency range, approximately 915 MHz. The microwaves are launched into a waveguide assembly 1202, within which a waveguide 1212 directs them through the other components of the system and to the applicator 1204, where they interact with the gas/plasma in the plasma reaction chamber 1214. The waveguide 1212 features a 90-degree bend 1216. One of the components of the waveguide is an isolator 1218 with an attached water load 1220, located distal to the magnetron 1210, to protect the magnetron 1210 from reflected (un-absorbed) microwaves by directing them with a ferritic core 1222 to the water load 1220. The other components of the waveguide assembly 1202 allow the microwaves to be guided towards the plasma reaction chamber 1214 and tuned to optimize the creation of the plasma therein. The applicator 1204 provides the interface between the microwaves and the quartz tube 1224 within which the plasma is created. Plasma is formed within the plasma reaction chamber 1214, the region of the quartz tube 1224 within which the chemical transformations take place. As shown in cross-section in FIG. 12, the quartz tube 1224 is disposed within, but is separated from, the applicator 1204 by an air gap (not labeled).

When the plasma is off and the microwaves are on, a standing wave is formed in the applicator 1204 between the 3-stub tuner 1230 and a sliding shorting plate 1232 on the end of the applicator 1204, such that the electric field is sufficient to initiate breakdown of the gas molecules in the quartz tube. Microwave energy entering the applicator 1204 is tuned to peak at the center of the plasma reaction chamber 1214, using the shorting plate 1232 as needed to change the length of the plasma reaction chamber 1214 and using the 3-stub tuner 1230 to change the phase of the incoming microwaves. Once the plasma has been initiated, the stub locations in the tuner 1230 can be altered preferentially to match the microwave power to the plasma, minimizing un-absorbed power. The 3-stub tuner 1230 contains power and phase sensors (not shown) and can algorithmically adjust the motor-driven stubs to minimize un-absorbed power. A dual-directional coupler 1234, which contains two small pinholes that couple microwaves with a known attenuation, is included in the waveguide 1212 proximal to the 3-stub tuner 1230. Power meters (not shown) are connected to these pinhole ports and convert the microwave power into a voltage, outputting forward and reflected power measurements. A thin quartz window 1238 is added into the waveguide system to prevent environmental debris and dust from entering the waveguide components.

b. Torch System for Acetylene Production

In embodiments, a plasma-based hydrocarbon processing system for producing acetylene and hydrogen can be of any scale and can deliver a range of purities and acetylene concentrations, depending on the desired end use. Plasma-based hydrocarbon processing systems as described previously can be designed for small scale applications and can be adapted to the needs of the end user. To facilitate this customization, a plasma-based hydrocarbon processing system can be configured so that the outflow (effluent) stream from the reactor is separated into gas streams having different compositions, for example, a stream having a higher concentration of acetylene and a stream having a higher concentration of hydrogen. Small-scale plasma-based hydrocarbon processing systems can be designed to deliver pure gas streams, or they can deliver acetylene-hydrogen mixtures, with or without other gases included in the output gas flow. A small-scale system or "mini-unit" as described above can be designed to produce only acetylene-hydrogen mixtures in its reactor, with gas effluent varying from 0.5%-75% acetylene, therefore minimizing the amount of separation required and reducing the complexity of the system. In embodiments, the end user can manipulate the parameters of the separation subsystem to produce a desired composition of acetylene admixed with hydrogen; in embodiments, the parameters of the microwave plasma reactor module in the mini-unit can be adjusted as well, although for more extensive parameter customization, a larger unit is desirable.

In an embodiment, the overall size of the plasma-based hydrocarbon processing system can be scaled, for example from a smaller scale unit such as a table-sized mini-unit (e.g., 4 feet wide by 8 feet long by 4 feet tall) to a large-scale unit that is 20×20×20 feet or larger. In an embodiment, the plasma-based hydrocarbon processing system can be sized so that it is portable. Desirable sizing for a portable unit ranges from the table-sized dimensions (e.g., 4×8×4) to the size of a standard shipping container. While shipping containers vary in size, a standard 20-foot ISO shipping container size would allow transportation of a portable-sized unit; such containers are typically about 8 feet wide, 20 feet long, and 8.5 to 9.5 feet high. Other, smaller, shipping containers can be used for smaller portable devices, for example, those having lengths of 10 feet or 8 feet, combined with height and width dimensions as mentioned above.

Such a small-scale system can be attached to small end-user apparatus (e.g., welding torches such as acetylene or oxy-acetylene torches) or to small storage facilities or storage tanks. In an embodiment, a 5 kW plasma-based hydrocarbon processing system mini-unit with dimensions of 4 feet wide by 8 feet long by 4 feet tall can produce acetylene-hydrogen mixtures of greater than 50% acetylene, in an amount sufficient to feed at least 5 oxy-fuel cutting torches of concurrent, continuous use. In embodiments, power ranges for a plasma-based hydrocarbon processing system mini-unit can range from about 1 kW to about 500 kW, with power ranges selected for desired commercial uses. A plasma-based hydrocarbon processing system such as this can be designed to be portable. As described above, larger units, for example up to the size of a standard ISO 20-foot shipping container, can also be designed to be portable. In embodiments, a portable plasma-based hydrocarbon processing system can be deployed to construction sites, demolition sites, shipyards, or remote operations like pipelines or offshore oil rigs, depending on the availability of a mixed gas stream such as natural gas or biogas, electricity, and water.

Figure 13:
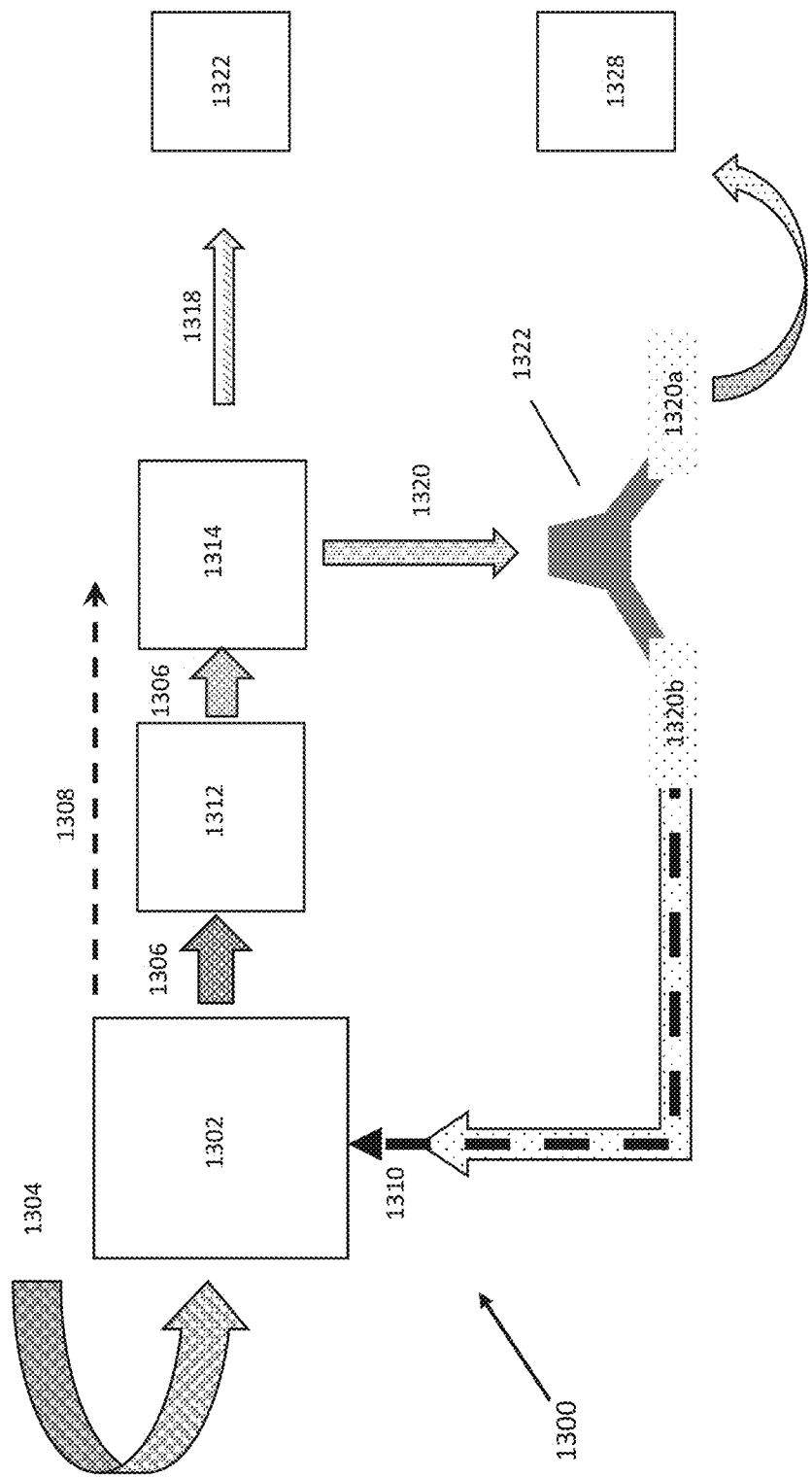
FIG. 13 is a block diagram of a small-scale system for gas processing.

FIG. 13 provides a block diagram of a small scale and scalable plasma-based hydrocarbon processing system 1300 suitable for industrial uses. As shown in FIG. 13, a plasma reactor 1302 substantially as described above has an input feed gas 1304 comprising a hydrocarbon such as methane, ethane, propane, butane, and the like, and derived from tanks or pipelines such as a natural gas line or a biogas tank or line. This input feed gas 1304 has a preselected inflow calibrated to produce an outflow (effluent) gas flow 1306 from the system 1300 ultimately suitable for a particular industrial purpose, for example metal cutting. In embodiments, an input feed gas 1304 such as methane or a methane-dense mixture such as natural gas or biogas can be used. In embodiments, a liquid source of an input feed gas 1304 such as propane or butane is advantageous, since such feed gas sources may be readily available in certain regions or facilities where a native gas source such as natural gas or biogas is not available.

In this Figure, the direction of gas flow is indicated by the arrow 1308 and other directional arrows. As an example of gas flows useful in the system 1300, a gas inflow within the range from about 0 to about 50 SLM can be selected; in an embodiment, a gas inflow of 5 SLM can produce a gas outflow of about 10 SLM. In embodiments, the input feed gas 1304 enters the plasma reactor 1302 as a sole gas input. In other embodiments, a separate gas input from a recycled gas stream 1310 enters the plasma reactor 1302 through a separate inflow nozzle (not shown), to be combined with the input feed gas 1304 within the plasma reactor 1302, for example using a gas injector (not shown) as described in previous Figures.

In an embodiment, the outflow 1306 from the plasma reactor 1302 contains about 14% acetylene, 84% hydrogen, and 2% methane, and it can be further processed by other components of the system. Entrained in the gaseous outflow 1306 are various carbon species byproducts, including higher-order carbon products and carbon particles, that can be removed prior to delivering a gas product to an end-user in certain embodiments. These byproducts can be removed in solid and liquid traps 1312, through which the outflow gas 1306 passes after being processed in the plasma reactor 1302. After the byproducts are removed, the gas stream 1306 is processed through a hydrogen separation system 1314, which can include a hydrogen separation membrane system, a short-cycle temperature swing adsorber, or a pressure swing adsorber that removes hydrogen. Such processing allows an acetylene-rich stream 1318 to be separated from a hydrogen-rich stream 1320, with the acetylene-rich stream 1318 being available to the end-user for industrial purposes, e.g., metal cutting. In other embodiments, there is no advantage to removing the higher-order carbon products, for example if the gaseous effluent is to be used for welding or other industrial uses where a purified acetylene stream is unnecessary. However, it is understood that higher-order carbon products can foul hydrogen separation membranes, so that these species should be removed if a hydrogen separation membrane system is used; alternatively, if a mixed effluent stream that includes the higher-order carbon products is commercially advantageous, a hydrogen separation system such as a short-cycle temperature swing adsorber or pressure swing adsorber can be used instead of a hydrogen separation membrane system.

As shown in the Figure, the acetylene-rich stream 1318, having been processed to remove higher-order carbon products and hydrogen, can be directed to various end uses or storage 1322. For example, the acetylene-rich stream 1318 can be directed into a pressurized tank, from which end-users can withdraw the gas mixture for use in metal cutting torches; advantageously, if the acetylene-rich stream 1318 is stored, the plasma-based hydrocarbon processing system can be run intermittently on an as-needed basis to fill the tank(s) for later use. In an embodiment, the acetylene-rich stream 1318 can contain about 50% acetylene, along with other components such as hydrogen, methane, and other gaseous additives as applicable. The acetylene-rich stream 1318 can be produced at a flow of about 2.1. SLM. In an embodiment, the hydrogen-rich stream 1320 can contain about 4% acetylene and 96% hydrogen, with a total flow of about 7.9 SLM. In embodiments, two or more separation membrane systems can be employed to increase the concentration of acetylene in the acetylene-rich product stream 1318, although a small-scale system can be designed with a single separation membrane system in order to limit the overall size of the apparatus.

In the plasma-based hydrocarbon processing system embodiment illustrated in FIG. 13, the hydrogen-rich stream 1320 can be directed through a splitter 1322, which can separate the hydrogen-rich stream 1320 into two substreams 1320a and 1320b, one (1320a) for end uses, disposal, and/or storage, and one (1320b) for recycling as a recycled gas stream 1310 into the plasma reactor 1302, where it can be processed along with the input feed gas 1304. The splitter 1322 can be formed from components familiar to those of skill in the art, such as Y-valves, mass flow controllers and the like. The hydrogen-rich substream 1320a that is not recycled can be vented, disposed of, collected, burned, or otherwise used, as required by the specific industrial setting.

The hydrogen-rich substream 1320b used for recycling can have the same composition as the substream 1320a that is directed to end uses, disposal, and/or storage. In an embodiment, a recycle flow 1310 of about 5 SLM can be redirected into the plasma reactor 1302, having a composition of about 97.5% hydrogen and 2.5% acetylene, yielding a recycle flow of about 5 SLM hydrogen. With a recycled stream 1310 combined with the input feed gas 1304 to fuel chemical transformations in the plasma reactor 1302, an outflow gas 1306 is produced, as described above. In embodiments, the proportion for recycling can be tuned, based on the user's requirements. For recycling, a mass flow controller that meters the amount of hydrogen-rich gas 1320b for recycling offers particular consistency, with the remainder directed to end-uses, disposal, or storage.

Figure 14:
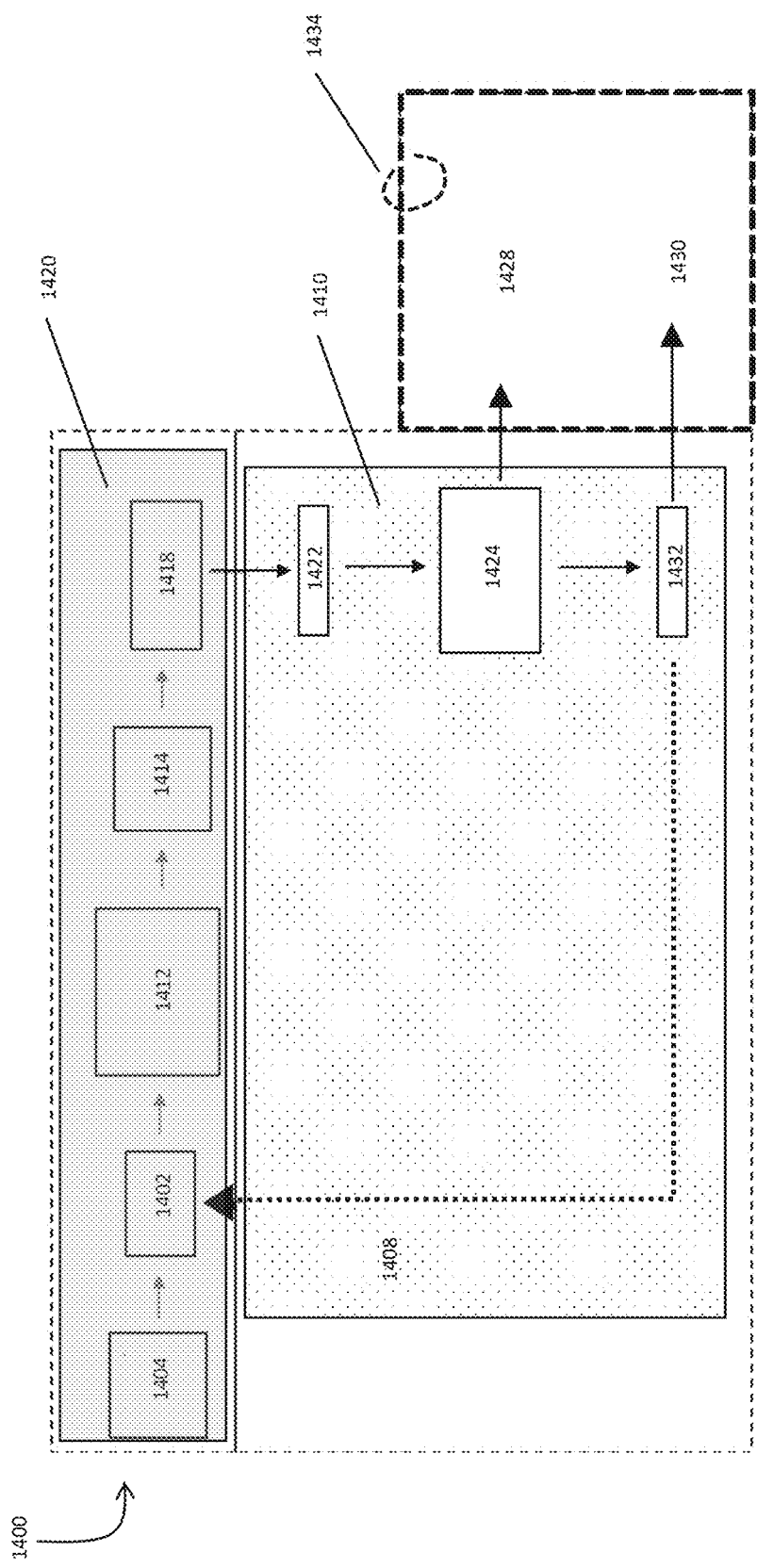
FIG. 14 is a block diagram of a small-scale system for gas processing.

FIG. 14 shows, in more detail, a modular plasma-based hydrocarbon processing system 1400 suitable for small-scale or larger-scale use, with arrows showing directions for gas flow. As shown in FIG. 14, a gas pipeline 1404, for example a natural gas pipeline, can provide the inflow gas for the microwave plasma reactor 1402, although any source of inflow gas can be used (a supply tank containing the gas, for example, as would be available for $C_1$-$C_4$ alkanes, or a line or tank delivering biogas). The inflow gas can be supplemented by a recycled stream 1408 containing a hydrogen-rich gas. Following processing in the microwave plasma reactor 1402, the outflow (effluent) gas passes through a heavy liquids trap 1412 that removes the higher-order hydrocarbons using a combination of a cold trap and/or a carbon adsorber. As a next stage, the outflow gas passes through a filter 1414 that removes particulate matter, for example carbon soot. The gas pressure is then adjusted by a vacuum pump 1418 and then the gas is compressed by a compressor 1422 to pass through a hydrogen separator 1424. The plasma reactor 1402, the heavy liquids trap 1412, the solids filter 1414, and the vacuum pump 1418 are grouped together as the reactor subsystem 1420. This can be located in proximity to the hydrogen recycle subsystem 1410 and the effluent management subsystem 1434, or these subsystems can be in fluid communication with each other but arranged remotely from each other, as is convenient for a particular industrial application.

As mentioned previously, the hydrogen separator 1424 can include one or more hydrogen separation units; in an exemplary embodiment, each hydrogen separation unit can contain one or more hydrogen separation membranes, but other configurations and separator technologies (for example, a short-cycle temperature swing adsorber describe previously or a pressure swing adsorber technology to separate hydrogen) can be employed. The configurations of the hydrogen separator units are adaptable to permit lesser or greater acetylene enrichment in the effluent acetylene-rich stream 1428. Depending on the desired industrial use, this effluent stream 1428 can be used directly as a cutting stream, or it can be stored as a product stream. In an embodiment, the gas remaining after the acetylene-rich stream 1424 is removed contains a large proportion of hydrogen. As previously described, this hydrogen-rich stream can be split into two substreams in a splitter 1432, with one stream 1408 designated for recycle, and one stream 1430 for disposal, venting, burning, commercialization, or other uses as desired.

Effluent management subsystems, substantially as described previously, can be integrated with the reactor subsystem (including a gas delivery subsystem, a microwave subsystem, and a vacuum subsystem, previously described but not shown in FIG. 14) within a single mini-unit for specific applications. The size, number, and complexity of the components required for the effluent separation processes can affect the size of the system overall. In an embodiment, a single plasma reactor can utilize a single hydrogen separation subsystem to provide a small footprint, with the subsystem including one or two hydrogen-separating membranes or other separation subsystem technologies, such as pressure swing adsorption. In an embodiment, separation subsystems, for example for hydrogen separation, can be integrated with the plasma-based hydrocarbon processing system.

In an embodiment of a modular plasma-based hydrocarbon processing system using a single hydrogen separation unit with a single separation membrane, the outflow gas from the reactor can contain the following gaseous components, at a flow rate of 10 SLM: 14% acetylene, 81% hydrogen, 2% methane, and 3% nitrogen. Following processing through a hydrogen separation unit having a single separation membrane, a hydrogen-rich stream is formed, containing the following gaseous components at a flow rate of 7 SLM: 4% acetylene, 96% hydrogen. Simultaneously, an acetylene-rich stream is formed, containing the following gaseous components at a flow rate of 3 SLM: 50% acetylene, 27% hydrogen, 9% methane, and 14% nitrogen. Using this process, 93.75% acetylene retention is accomplished in the acetylene-rich stream, and 86.5% of hydrogen is recycled. The flow rates and mol ratios of the components of the various gas streams for the one-membrane hydrogen separation system are shown in Table 3 below:

TABLE 3

| | Plasma Reactor Effluent | | Acetylene-rich stream | | Hydrogen-rich stream | | Vent/burn | | Recycle Stream | |
|---|---|---|---|---|---|---|---|---|---|---|
| | Flow Rate (SLM) | mol ratio | Flow Rate (SLM) | mol ratio | Flow Rate (SLM) | mol ratio | Flow Rate (SLM) | mol ratio | Flow Rate (SLM) | mol ratio |
| $H_2$ | 8.1 | 0.81 | 0.567 | 0.268 | 7.53 | 0.956 | 3.53 | 0.956 | 4 | 0.956 |
| $CH_4$ | 0.2 | 0.02 | 0.2 | 0.094 | 0 | 0 | 0 | 0 | 0 | 0 |
| $N_2$ | 0.3 | 0.03 | 0.3 | 0.142 | 0 | 0 | 0 | 0 | 0 | 0 |
| $C_2H_2$ | 1.4 | 0.14 | 1.05 | 0.496 | 0.35 | 0.044 | 0.164 | 0.044 | 0.186 | 0.044 |
| Total | 10 | | 2.12 | | 7.88 | | 3.694 | | 4.186 | |

A double-membrane hydrogen separation unit can extract more hydrogen from the reactor's outflow gas, yielding a hydrogen-rich stream containing 1.2% acetylene and 98.8% hydrogen, at a flow of 7 SLM. With this system, an acetylene-rich stream is formed containing the following gaseous components at a flow rate of 3 SLM: 45% acetylene, 38% hydrogen, 7% methane, and 10% nitrogen. The flow rates and mol ratios of the components of the various gas streams for the two-membrane hydrogen separation system are shown in Table 4 below:

TABLE 4

| | Plasma Reactor Effluent | | Acetylene-rich stream | | Hydrogen-rich stream | | Vent/burn | | Recycle Stream | |
|---|---|---|---|---|---|---|---|---|---|---|
| | Flow Rate (SLM) | mol ratio | Flow Rate (SLM) | mol ratio | Flow Rate (SLM) | mol ratio | Flow Rate (SLM) | mol ratio | Flow Rate (SLM) | mol ratio |
| H2 | 8.1 | 0.81 | 1.09 | 0.376 | 7.006 | 0.988 | 3.53 | 0.988 | 4 | 0.988 |
| CH4 | 0.2 | 0.02 | 0.2 | 0.069 | 0 | 0 | 0 | 0 | 0 | 0 |
| N2 | 0.3 | 0.03 | 0.3 | 0.103 | 0 | 0 | 0 | 0 | 0 | 0 |
| C2H2 | 1.4 | 0.14 | 1.05 | 0.452 | 0.088 | 0.012 | 0.038 | 0.012 | 0.05 | 0.012 |
| Total | 10 | | 2.12 | | 7.094 | | 3.568 | | 4.05 | |

A wide variety of industrial uses can be envisioned for small scale or modular plasma-based hydrocarbon processing systems as described herein. As mentioned above, a major industrial use for acetylene is in the metalworking industry, for example in metal cutting. For these purposes, an appropriately sized plasma-based hydrocarbon processing system in accordance with this disclosure can be used directly or via storage tanks to provide fuel for metal cutting. In addition, the plasma-based hydrocarbon processing system can be coupled with other systems to provide product versatility and to increase efficiency in the metalworking industry. As an example, in oxy-acetylene steel cutting facilities, the plasma-based hydrocarbon processing system can be used in conjunction with air separation units (ASUs). The ASU can separate air into nitrogen-rich and oxygen-rich streams, which can then be combined with the gas stream(s) used by or produced by microwave plasma reactor unit. Using this combination of apparatus, an operator can generate all the gas feedstock required for steel fabrication on-site.

4. Integrated Industrial Applications

In embodiments, a plasma-based hydrocarbon processing system, for producing acetylene and hydrogen, as described above, can deliver either of these products into subsystems for further processing, so that a fully integrated industrial application is constructed that incorporates precursor production (i.e., acetylene and/or hydrogen produced by the plasma-based hydrocarbon processing system) and precursor utilization to form industrially useful products.

a. Vinyl Chloride Monomer (VCM) Manufacture

As an example, the acetylene produced by the plasma-based hydrocarbon processing system can act as the precursor for other industrial processes, such as VCM manufacturing. A plasma-based hydrocarbon processing system as described above can be modified so that it maximizes and optimizes the acetylene produced, and it can be integrated with those processes required to convert the acetylene into VCM.

Figure 15A:
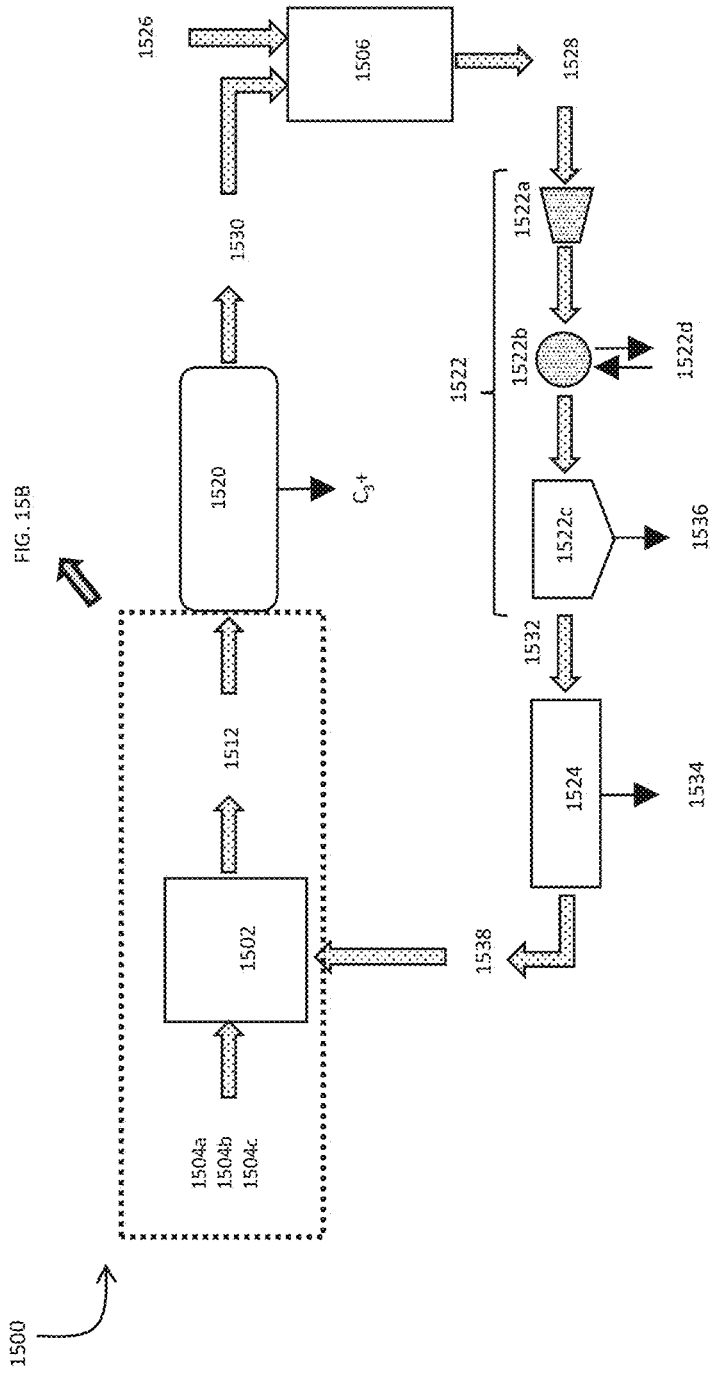
FIG. 15A is a block diagram of a system for use in an integrated process for VCM manufacture.

In exemplary embodiments, an integrated process for VCM manufacture can be envisioned as set forth in FIG. 15A. As shown in FIG. 15A, a system for VCM production 1500 can be based on a plasma-based hydrocarbon processing system, using certain of the components of the plasma-based hydrocarbon processing system that have already been described. In more detail, FIG. 15A depicts a system for VCM production 1500 comprising a plasma-based hydrocarbon processor 1502, a VCM reactor 1506, and a plurality of separators 1520, 1522, and 1524. The plasma-based hydrocarbon processor 1502 operates in keeping with the principles described and illustrated in the Figures above; it can use any of the plasma-based hydrocarbon processing systems described herein. As integrated with the other components of the VCM production system 1500, the plasma-based hydrocarbon processor 1502 is responsible for converting one or more inflow gases into a mixture of gaseous products contained in an outflow stream emerging from a plasma reaction chamber, where the plasma reaction chamber contains the plasma that has been generated by a microwave subsystem. Details of these components of the plasma-based hydrocarbon reactor are substantially similar to analogous components described herein, and as illustrated in previous Figures.

Figure 15B:
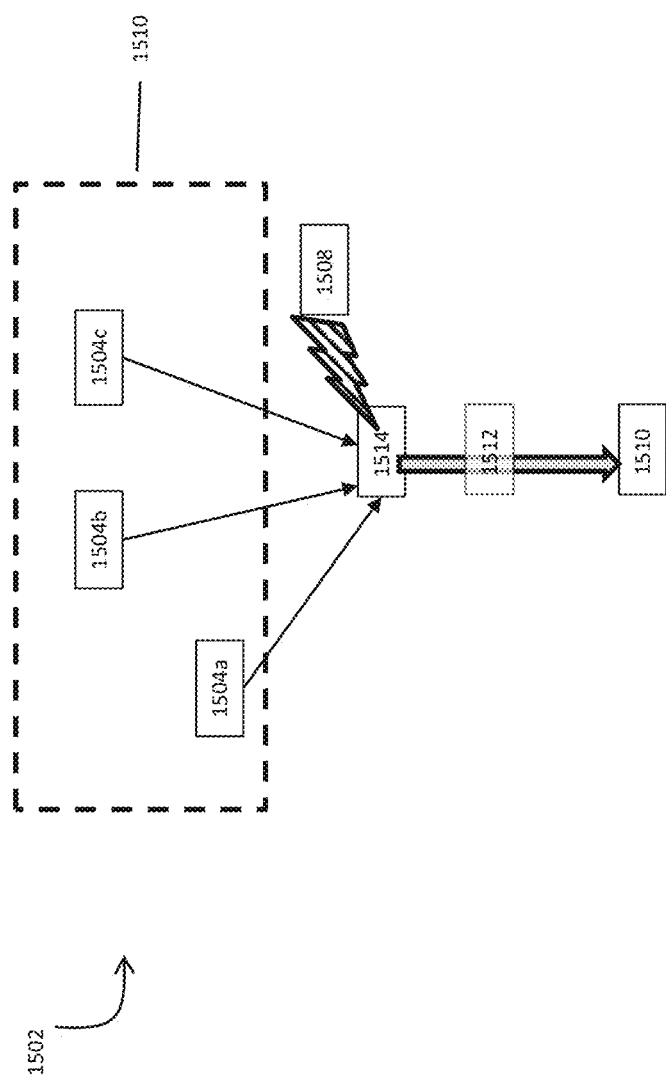
FIG. 15B is a block diagram of a plasma-based hydrocarbon processor suitable for use in an integrated process for VCM manufacture.

An embodiment of the plasma-based hydrocarbon processor 1502 suitable for use with the integrated VCM production system 1500 is shown in more detail in FIG. 15B. The embodiment depicted in FIG. 15B shows one example of a plasma-based hydrocarbon processor 1502 suitable for use with the integrated VCM production system shown in FIG. 15A. Other embodiments of plasma-based hydrocarbon processors as have been described herein can also be used with the VCM production system 1500. FIG. 15B shows a plasma-based hydrocarbon processor 1502 having a gas delivery subsystem 1510 that delivers one or more inflow gases 1504a, 1504b, 1504c into the plasma reaction chamber 1514 where they are energized by the microwave subsystem 1508 to form a plasma that yields chemical products that emerge from the plasma reaction chamber 1514 to form an outflow stream (or effluent stream) 1512 of outflow gas products. The outflow stream (or effluent stream) 1512 is then subjected to downstream processing 1510, to be described in more detail in conjunction with FIG. 15A. The inflow gases 1504a, 1504b, 1504c can include hydrogen gas, a hydrocarbon such as methane (either in pure form or as a component of a gas mixture such as natural gas), and other gases, all as previously described for the plasma-based hydrocarbon processing systems disclosed herein. In embodiments, one or more of the inflow gases 1504a, 1504b, and 1504c, can be a recycled gas. The outflow stream 1512 comprises acetylene and hydrogen, as previously described for the various embodiments of plasma-based hydrocarbon processing systems as set forth above.

Returning to FIG. 15A, the plasma-based hydrocarbon processor 1502 receives the one or more inflow gases 1504a, 1504b, 1504c, where at least one of the gases is a hydrocarbon gas, for example methane. In embodiments, the inflow hydrocarbon gas can be natural gas, as described above for the plasma-based hydrocarbon processing system, which comprises methane. Emanating from the plasma-based hydrocarbon processor 1502 is an outflow stream (or effluent stream) 1512 containing a mixture of acetylene, hydrogen, higher acetylenes and other products including higher hydrocarbons (collectively, ($C_3^+$)). To prepare the outflow stream 1512 for use in the VCM reactor 1506, the outflow stream 1512 is passed through the first of a plurality of separators, a first separation system 1520, which is an effluent separator that removes the higher acetylenes and aromatics ($C_3^+$) from the outflow stream 1512, yielding a purified effluent stream 1530 that is delivered to the VCM reactor 1506. A stream of hydrogen chloride gas 1526 is also delivered to the VCM reactor 1506. The acetylene contained in the purified effluent stream 1530 combines with the hydrogen chloride gas 1524 in the VCM reactor 1506 to produce VCM, as illustrated by the following formula:

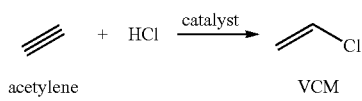

acetylene                     VCM

Emerging from the VCM reactor 1506 is a VCM reactor effluent 1528 that enters a second separation system 1522. This second separation system 1522 is a condensing system comprising a compressor 1522a to compress the VCM reactor effluent 1528 and a chiller 1522b that lowers the temperature of the VCM reactor effluent 1528, allowing the VCM to condense out of the VCM reactor effluent 1528 as a liquid, which can then be removed from the fluid stream by the liquid-gas separator 1522c as a liquid form of VCM 1536. The chiller 1522b can be operated by circulating refrigerant 1522d or any other mechanism familiar to artisans of ordinary skill. A stream of residual gas 1532 emerges from the liquid-gas separator 1522c for further processing by a third separation system 1524, which separates purified hydrogen from the residual gas 1532, leaving behind a stream of gas 1538 that can be recycled into the plasma-based hydrocarbon processor 1502.

In an embodiment, a plasma-based hydrocarbon processor 1502 can be set up substantially in the form of the 100 kw plasma-based hydrocarbon processing system described above; while this system has been described as having a magnetron power of 100 kW, it is understood that other amounts of power for the system can also be employed to power the plasma-based hydrocarbon processor. In this exemplary embodiment, the inflow gases 1504a and 1504b for the plasma-based hydrocarbon processor are natural gas (mostly methane) and recycle gas (mostly hydrogen). These inflow gases 1504a and 1504b react in the plasma-based hydrocarbon processor 1502 to produce the acetylene in the outflow stream 1512. As has been already detailed above for the plasma-based hydrocarbon reactor technology, the outflow stream 1512 comprises other substances as well, including hydrogen, higher acetylenes, aromatics, etc. The outflow stream 1512 is therefore processed by the first separation system 1520 to remove the higher hydrocarbons ($C_3^+$), such as the higher acetylenes and aromatics. As has been described above, effluent separation subsystems suitable for use as components of the first separation system 1520 can include prescrubbers, temperature swing adsorbers, and the like. As a result of its encounter with the first separation system 1520, the outflow stream 1512 emanating from the plasma-based hydrocarbon processor 1502 is purified of these higher hydrocarbons ($C_3^+$) and emerges as the purified effluent stream 1530. The purified effluent stream 1530 is combined with hydrogen chloride gas 1526 within VCM reactor 1506, where a reaction between the two gases is catalyzed to form VCM; the VCM thus formed is discharged from the VCM reactor in a VCM-containing gas stream, the VCM reactor effluent 1528. The VCM reactor effluent 1528 is then processed by the second separation system 1522, which condenses the liquid VCM 1536 and allows the residual gas 1532 to pass through to the third separation system 1524, which provides a hydrogen separator that separates the purified hydrogen product 1534 from the recycle gas stream 1538 returning to the reactor 1502. The hydrogen separator can be, for example, an $H_2$ membrane, an $H_2$ pressure swing adsorber, or other technologies described herein for hydrogen separation. While the system for VCM production 1500 has been exemplified by reference to the 100 kw plasma-based hydrocarbon processing system described above, it is understood that other versions of the plasma-based hydrocarbon processing systems disclosed herein are also suitable for use in this integrated system and method. It is understood that the system for VCM production 1500 can use a plasma-based hydrocarbon processing system of any scale, and delivers a range of purities and acetylene concentrations. As an example, the plasma-based hydrocarbon processing systems described above for small scale applications can be used with the system for VCM production.

Figure 16:
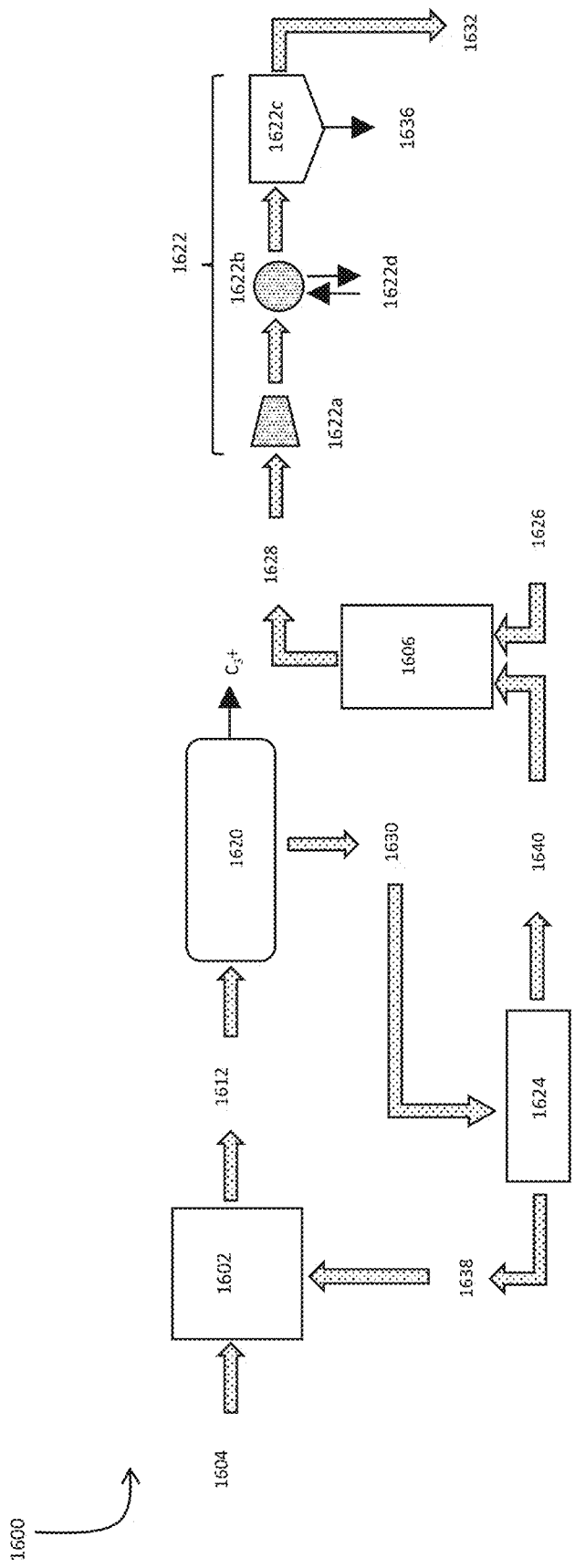
FIG. 16 is a block diagram of a system for use in an integrated process for VCM manufacture.

FIG. 16 depicts an alternative embodiment of a system for VCM production integrated with a plasma-based hydrocarbon processing system, using certain of the components of the plasma-based hydrocarbon processing system that have already been described. In more detail, FIG. 16 depicts a system for VCM production 1600 comprising a plasma-based hydrocarbon processor 1602, a VCM reactor 1606, and a plurality of separators 1620, 1622, and 1624. The plasma-based hydrocarbon processor 1602 operates according to the principles described and illustrated in the Figures above; it can use any of the plasma-based hydrocarbon processing systems described previously. As integrated with the other components of the VCM production system 1600, the plasma-based hydrocarbon processor 1602 is responsible for converting one or more inflow gases 1604 into a mixture of gaseous products contained in an outflow stream emerging from a plasma reaction chamber (not shown), where the plasma reaction chamber contains the plasma that has been generated by a microwave subsystem (not shown). Details of these components of the plasma-based hydrocarbon reactor are substantially similar to analogous components described above and illustrated in the foregoing Figures. However, while the components of the system 1600 are substantially similar to those illustrated in FIG. 15A and FIG. 15B, their arrangement is different. As shown in FIG. 16, the inflow gas 1604 enters the plasma-based hydrocarbon processor 1602, where it mixes with any other inflow gases (including recycled gas 1638) and where it is transformed into an acetylene-containing effluent stream 1612 via its encounter with the plasma within the plasma-based hydrocarbon processor 1602. The effluent stream 1612 then passes into a first separation system 1620, where higher hydrocarbons ($C_3^+$) (e.g., acetylenes and aromatic compounds) are removed. The purified effluent stream 1630 emerging from the first separation system 1620 passes into a second separation system 1624, which separates hydrogen from the fluid stream. Hydrogen can be recycled 1638 into the plasma-based hydrocarbon processor 1602 for further reactions therein. The hydrogen separation system 1624 also produces a concentrated effluent stream 1640 that contains acetylene, which can then be reacted with hydrogen chloride gas 1626 within the VCM reactor 1606 to yield VCM. The VCM-containing gas stream, the VCM reactor effluent 1628, then enters the third separation system 1622, which condenses the VCM from the VCM reactor effluent 1628 through a series of components substantially similar to those described in FIG. 15A. In more detail, this third separation system 1622 comprises a compressor 1622*a* to compress the VCM reactor effluent 1628 and a chiller 1622*b* that lowers the temperature of the VCM reactor effluent 1628, allowing the VCM to condense out of the VCM effluent as a liquid, which can then be removed from the fluid stream by the liquid-gas separator 1622*c* as a separate liquid VCM product 1636. The chiller 1622*b* can be operated by circulating refrigerant 1622*d* or any other mechanism familiar to artisans of ordinary skill. The stream of residual gas 1632 that emerges from the liquid-gas separator 1622*c* contains mainly hydrogen, and the residual gas stream 1632 can then be discarded or further processed through a hydrogen separator (either by routing it (not shown) to the hydrogen separator 1624 previously described, or another hydrogen separator not shown).

Figure 17:
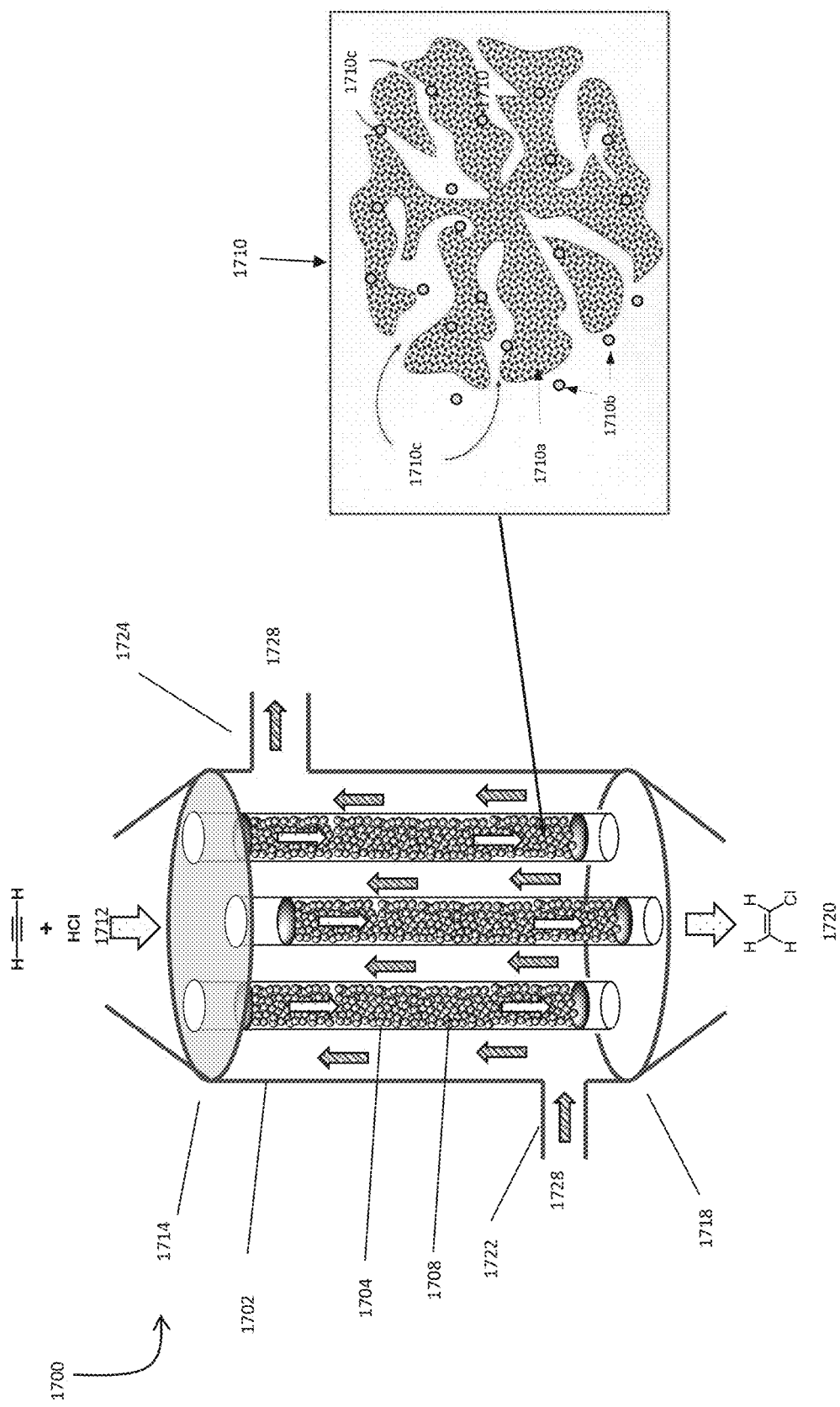
FIG. 17 is a schematic illustration of a VCM reactor suitable for use in an integrated process for VCM manufacture.

FIG. 15A and FIG. 16 each depicts a VCM reactor (1506, 1606) that converts acetylene and hydrogen chloride gas into VCM. An embodiment of an exemplary VCM reactor for use with the aforesaid systems and methods for VCM manufacture is shown in more detail in FIG. 17. The VCM reactor 1700 comprises an external housing 1702 within which is supported a catalytic bed, which in the depicted embodiment is formed from a plurality of catalyst-containing cylindrical tubes 1704. The housing can be made of stainless steel or any other suitable substance, as is known in the art. The catalyst-containing tubes 1704 can be made of glass or any other suitable substance as is known in the art. A plurality of catalyst pellets are deployed within the catalyst-containing tubes 1704 to form a packed bed 1708. Each of the catalyst pellets 1710 comprises a support 1710*a* attached to which or in proximity to which are a plurality of catalyst particles 1710*b*; the support 1710*a* is configured with pores 1710*c* through at least some of which the purified effluent stream containing acetylene passes to contact the catalyst particles, thereby increasing the surface area across which the reactants can contact the catalyst particles 1710*b*. Reactants 1712 (acetylene and HCl gas) enter a proximal end 1714 of the catalyst-containing tubes 1704, and pass through the tubes 1704 distally to their distal end 1718. As the reactants 1712 pass through the tubes 1704, they contact the catalyst particles therein and undergo a catalytic reaction to form the desired product VCM 1720. The VCM 1720 emerges from the distal end 1718 of the catalyst-containing tubes 1704. An elevated reaction temperature may be desirable, in which case heated oil or any other heated substance can be circulated within the reactor to surround the catalyst-containing tubes 1704. In the depicted embodiment, hot oil 1728 enters at an inlet 1722 located on a distal portion of the reactor housing 1702, and it exits at an outlet 1724 located on a proximal portion of the reactor housing 1702. In embodiments, a hot oil temperature between 150 and 220° C. is advantageous. Other temperatures can be maintained by varying the temperature of the circulating heating substance or cooling substance as appropriate. Other modifications of reactor design can be substituted for this example without departing from the spirit and scope of the disclosed invention, as would be understood by those of ordinary skill in the art.

Catalysts suitable for use with the VCM reactor system described herein are familiar in the art and can be prepared by individuals with ordinary skill by following published procedures, such as those set forth in the following references, whose contents are incorporated herein by reference. Examples of catalysts suitable for use with these systems and methods include, without limitation: $HgCl_2$ on activated carbon (disclosed, for example, in U.S. Pat. No. 2,446,123); $Au_2(S_2O_3)_3$ on activated carbon (disclosed, for example, in U.S. Pat. No. 9,409,161), $HAuCl_4$ on activated carbon (disclosed, for example, in *J. Catal.*, 2013, 297, 128-136); $AuCl_3$ on mesoporous carbon material (disclosed, for example, in *Catal. Sci. Technol.*, 2015, 5, 1035-1040) $HAuCl_4$, $H_2PtCl_6$, $RhCl_3$, $IrCl_3$, and/or $PdCl_2$ on activated carbon (disclosed, for example, in *J. Catal.*, 2008, 257, 190-198); $CuCl_2$ and $BiCl_3$ on silica gel (disclosed, for example, in *Fuel Process. Technol.*, 2013, 108, 12-18); $(PPh_3)AuCl$ on activated carbon (disclosed, for example, in *Catal. Sci. Technolog.*, 2016, 6, 7946-7955), $RuCl_3$ on activated carbon (disclosed, for example, in *RSC Adv.*, 2017, 7, 23742-23750). Bimetallic catalytic systems for acetylene hydrochlorination are also suitable for use with the VCM reactor system described herein, including AuCl, AuLa, AuBa, AuNi, AuCs, $AuTiO_2$, and AuCoCu; descriptions of suitable bimetallic catalyst systems can be found in *ACS Catal.*, 2015, 5, 5306-5316.

b. Vitamins A and E Manufacturing

As another example, the acetylene and hydrogen produced by the plasma-based hydrocarbon processing system can act as the precursor for other industrial processes, such as the manufacturing of Vitamins A and E and their respective chemical intermediates. A plasma-based hydrocarbon processing system as described above can be modified so that it maximizes and optimizes the acetylene produced, and it can be integrated with those processes required to convert the acetylene into these vitamin products. In addition, such a system can produce hydrogen, which can be used in manufacturing vitamin products.

In embodiments, a plasma-based hydrocarbon processing system for producing acetylene and hydrogen, as described above, can deliver either of these products into subsystems for further processing, so that a fully integrated industrial application is constructed that incorporates precursor production (i.e., acetylene and/or hydrogen produced by the plasma-based hydrocarbon processing system) and precursor utilization to form industrially useful products. For example, the acetylene produced by the plasma-based hydrocarbon processing system can act as the precursor for other industrial processes, such as the manufacture of Vitamins A and E, provitamin beta-carotene, and their respective chemical intermediates. Acetylene, along with $C_3$-feedstock (e.g., Acetone, diketene, ethyl acetoacetate, isopropenyl methyl ether) and hydrogen, is a vital raw material for the commercial productions of vitamins A and E, and provitamin β-Carotene (collectively, "vitamin products"). A plasma-based hydrocarbon processing system as described above can be modified so that it maximizes and optimizes the acetylene produced, and it can be integrated with those processes required to convert the acetylene into these products.

Figure 18:
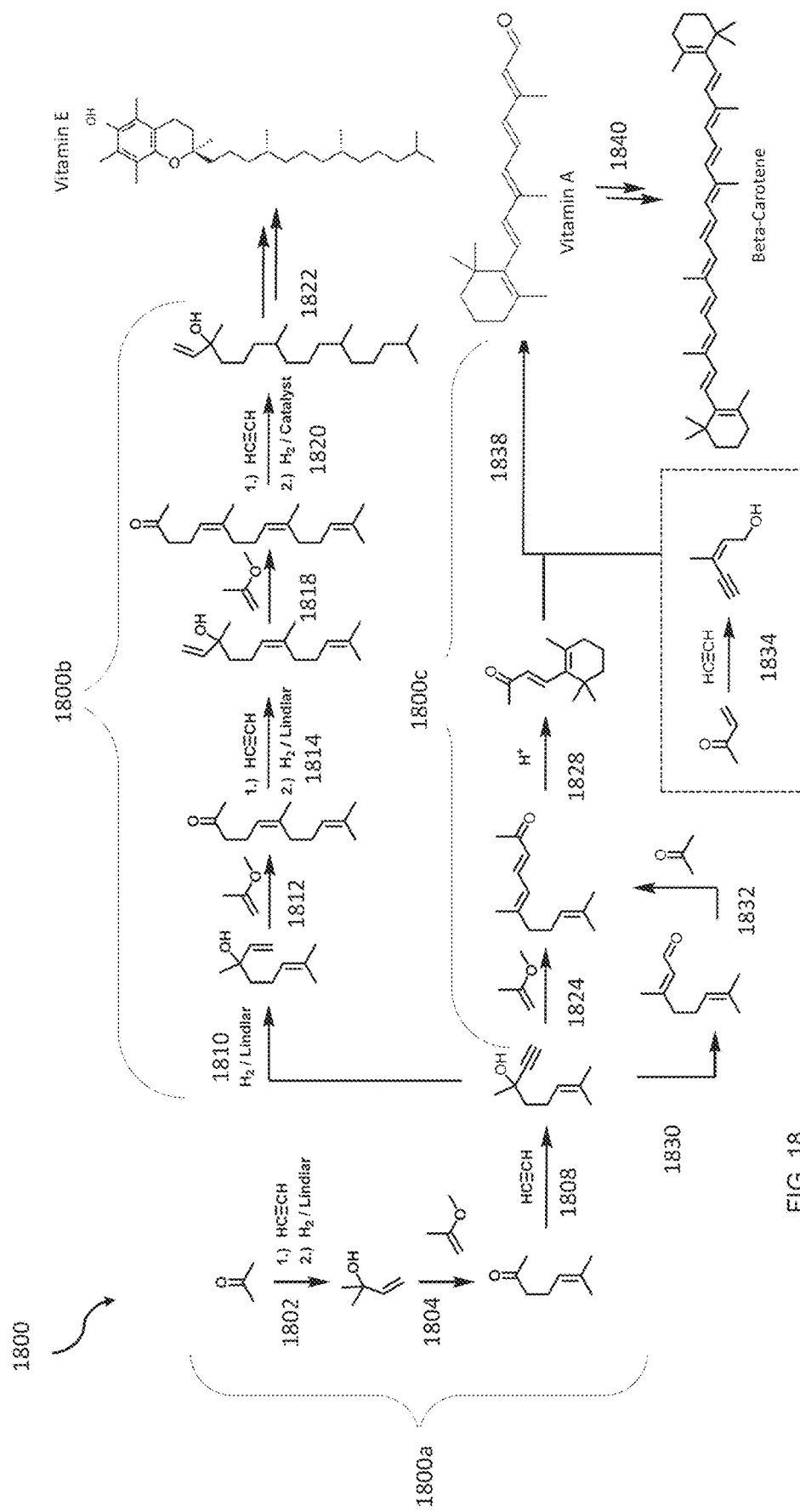
FIG. 18 shows an embodiment of a multistep synthetic pathway for production of Vitamins A and E and beta-carotene.

A representative multistep synthetic pathway showing the chemical intermediates useful for the manufacture of Vitamins A and E and the provitamin beta-carotene is set forth in FIG. 18. From an overall mass balance perspective, 1 kg of vitamin products consists of 0.25 kg $C_2H_2$ in Vitamin E, and 0.27 kg $C_2H_2$ in Vitamin A, and 0.29 kg $C_2H_2$ in β-Carotene. The synthetic paths 1800 shown in FIG. 18 permit the synthesis of vitamin products using acetylene as the main hydrocarbon ingredient. As shown in FIG. 18, a common initial pathway (1800*a*, comprising Steps 1802, 1804, 1808) produces the common precursor dehydrolinalool, which is then transformed into Vitamin E via pathway 1800*b* (comprising Steps 1810, 1812, 1814, 1818, 1820 and 1822), or which is then transformed into Vitamin A through pathway 1800*c* (comprising Step 1824, or alternatively Steps 1830 and 1832, then Steps 1828, 1838, and 1840; Step

1834 shows the pathway by which a precursor for step 1838 is formed). As used herein, the term "Vitamin A" refers to and includes the four main forms of Vitamin A: retinal, retinol, retinoic acid, and retinol-esters (e.g., retinol acetate). For simplicity, the structure of Vitamin A is depicted as retinol in FIGS. 18, 19 and Table 5 (below). Beta-carotene is formed from Vitamin A as represented schematically in Step 1840.

In the first step of the common initial pathway 1800a (Step 1802), there are two separated reaction sequences to this step: ethynylation and hydrogenation. The former involves reacting acetone with acetylene in the presence of a base/solvent combination (as described below). In this step, acetylene's terminal hydrogen atom is deprotonated by the base, allowing the acetylide to attach to the carbonyl of the acetone. The second sequence following ethynylation, as depicted in this Figure, is hydrogenation by Lindlar catalyst that hydrogenates the alkyne to alkene moiety. Overall, step 1802 produces 2-methylbut-3-en-2-ol, which in Step 1804 reacts with isopropenyl methyl ether to form 6-methylhept-5-en-2-one. In Step 1808, acetylene is reacted with 6-methylhept-5-en-2-one (from Step 1804) to produce dehydrolinalool, the common precursor for Pathways 1800b and 1800c. For convenience, names of reagents, intermediates, and products shown in FIG. 18 are set forth in Table 5. Note, chemical structures shown in FIGS. 18, 19 and Table 5 do not refer to a specific E/Z and R/S stereoisomer configuration for their respective chemicals' names. For simplicity, only a single stereoisomer structure is shown in the figures and tables. Moreover, the chemicals names used herein are understood by artisans of ordinary skill to refer to all possible stereoisomers, including, but not limited to, a single stereoisomer, a non-racemic mixture of stereoisomers, and a racemic mixture of stereoisomers of the same compound.

TABLE 5

| Structure/Formula | Name(s) |
|---|---|
|  | Acetone<br>Propan-2-one |
| HC≡CH | Acetylene<br>Ethyne |
|  | But-3-en-2-one |
| 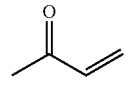 | 2-methylbut-3-en-2-ol |
| 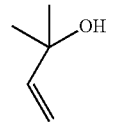 | 3-methylpent-2-en-4-yne-1-ol |
| 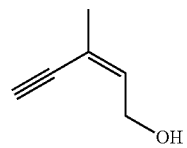 | Isopropenyl methyl ether<br>2-methoxyprop-1-ene |
| 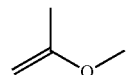 | 6-methylhept-5-en-2-one |
| 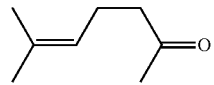 | Dehydrolinalool<br>3,7-dimethyloct-6-en-1-yn-3-ol |
| 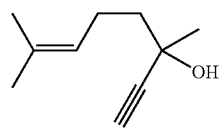 | Linalool<br>3,7-dimethylocta-1,6-dien-3-ol |
| 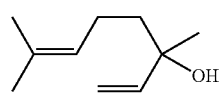 | 6,10-dimethylundeca-5,9-dien-2-one |

TABLE 5-continued

| Structure/Formula | Name(s) |
|---|---|
| | 3,7,11-trimethyldodeca-1,6,10-trien-3-ol |
| | 6,10,14-trimethylpentadeca-5,9,13-trien-2-one |
| | 3,7,11,15-tetramethylhexadec-1-en-3-ol |
| | Vitamin E<br>2,5,7,8-tetramethyl-2-(4,8,12-trimethyltridecyl)chroman-6-ol |
| | Pseudoionone<br>6,10-dimethylundeca-3,5,9-trien-2-one |
| | Citral<br>3,7-dimethylocta-2,6-dienal |
| | β-ionone<br>4-(2,6,6-trimethylcyclohex-1-en-1-yl)but-3-en-2-one |
| | Vitamin A<br>3,7-dimethyl-9-(2,6,6-trimethylcyclohex-1-en-1-yl)nona-2,4,6,7-tetraenal |
| | β-Carotene<br>2,2'-(3,7,12,16-tetramethyloctadeca-1,3,5,7,9,11,13,15,17-nonaene-1,18-diyl)bis(1,3,3-trimethylcyclohex-1-ene) |

Following Pathway 1800b results in the formation of Vitamin E through Steps 1810, 1812, 1814, 1818, 1820, and 1822. In more detail, Step 1810 hydrogenates dehydrolinalool in the presence of a Lindlar catalyst to form linalool. Step 1812 combines linalool with isopropenyl methyl ether to form 6,10-dimethylundeca-5,9-dien-2-one. In Step 1814, this product is first reacted with acetylene, and then catalytically hydrogenated, to produce 3,7,11-trimethyldodeca-1,6,10-trien-3-ol. This product is then reacted with 2-methoxy-1-propene (Step 1818), to form a product that is reacted with acetylene and then catalytically hydrogenated (Step 1820) to form 3,7,11,15-tetramethylhexadec-1-en-3-ol, which is converted via Step 1822 by a catalyzed Friedel-Craft alkylation to form Vitamin E, for example, following those procedures set forth in CHIMIA 2014, 68, 485-491, the contents of which are included herein by reference.

Pathway 1800c results in the formation of Vitamin A, through Steps 1824 (or alternate Steps 1830 and 1832) through Steps 1828 and 1838. Either Step 1824 or Steps 1830 and 1832 result in the formation of pseudoionone, which can then be converted into beta-ionone by acidification, as shown in Step 1828. To form pseudoionone in Step 1824, isopropenyl methyl ether is added to dehydrolinalool. Alternatively, pseudoionone is formed through Steps 1830 and 1832, by first converting dehydrolinalool to citral using a vanadium catalyst through an internal rearrangement process, and then combining citral with acetone to produce pseudoionone. Pseudoionone can then be converted into beta-ionone by acidification in Step 1828. Once beta-ionone is formed, it can be combined with 3-methylpent-2-en-4-yn-1-ol (formed from acetylene and methyl vinyl ketone in step 1834) to yield Vitamin A. Vitamin A, in turn, can be used as a precursor for other molecules, for example, Beta-carotene, represented schematically by Step 1840.

Underpinning the complex synthetic pathway for vitamins/provitamins as shown in FIG. 18 are controlled ethynylation reactions where acetylene selectively adds methyl ketone groups. These reactions proceed by a singular deprotonation of acetylene's C—H bonds by a strong base followed by addition of a ketone electrophile (e.g., acetone) resulting in a C—C bond formation, as illustrated by the following formula:

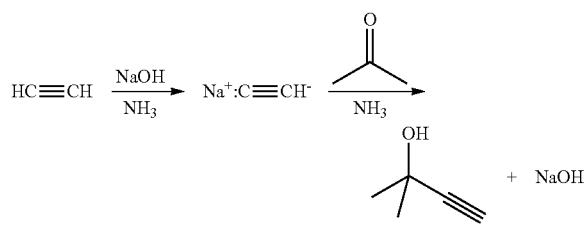

In many cases, only a catalytic amount of base is needed to be added to the reactor to effect the necessary deprotonation. In commercial applications, potassium hydroxide and liquid ammonia is the preferred base/solvent combo, as illustrated above. Other base/solvent combination that can be used for ethynylation reactions include but limited to potassium hydroxide/dimethyl sulfoxide, sodium/methanol, potassium hydride/tetrahydrofuran, and sodium amide/diethyl ether. The base-mediated reaction occurs once per acetylene molecule, preventing over-alkylation of the acetylene. This simple stepwise reaction is repeated numerous times in an ethynylation, hydrogenation, and condensation reaction sequence as depicted in FIG. 18 to construct the long terpenoid structures that form the backbone of the final vitamin products. These ethynylation reactions can be performed in batch-wise or semi-continuously, typically using sodium hydroxide in ammonia to deprotonate acetylene, which operates catalytically, reducing the amount of base required.

Figure 19:
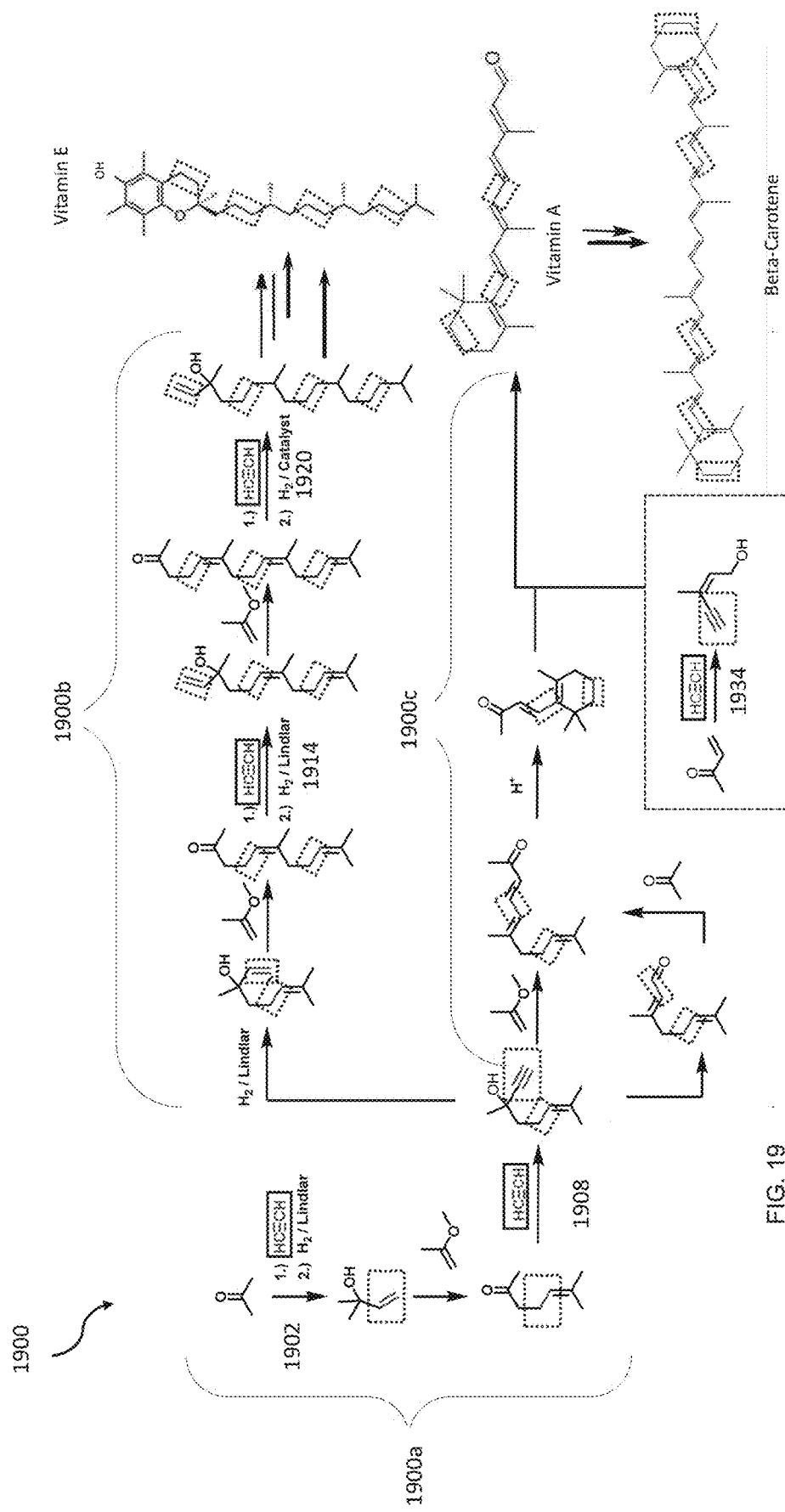
FIG. 19 shows the multistep synthetic pathway of FIG. 18 with certain details highlighted for clarity.

FIG. 19 depicts a multistep synthesis 1900 that is identical to that shown in FIG. 18, with certain details in pathways 1900a, 1900b, and 1900c highlighted for clarity. In this Figure, dashed boxes are placed within the structures in the reactions to show those carbon atoms contributed by acetylene to synthetic intermediaries and final products, and solid boxes are placed around the acetylene molecules themselves. The illustrations in FIG. 19 demonstrate schematically the centrality of acetylene to the synthesis of vitamin products. In FIG. 19, the incorporation of acetylene is seen in Steps 1902, 1908, 1914, 1920, and 1934. Acetylene for each of these steps can be provided by a plasma-based hydrocarbon processing system, as described herein.

An illustrative example of such a plasma-based hydrocarbon processing system that would be useful for producing acetylene and hydrogen for vitamin manufacturing has been previously described in conjunction with FIG. 9. As previously shown in FIG. 9 above and described in more detail herein, the inflow gas streams 912 and 914 are processed in the reactor 902 to form an outflow stream 918 that contains acetylene, hydrogen, and a small proportion of mixed hydrocarbons. The outflow stream 918 is then separated into its gaseous components via a gas separation system 928 (e.g., adsorption, absorption, or a combination thereof) to yield an acetylene stream 920 and a hydrogen-dominant gas stream 922 that contains hydrogen 936 and a mixture of hydrocarbons 924. Thus diverted from the main outflow stream 918 by the gas separation system 928, the acetylene stream 920 can be purified via further sequestration of impurities in a purification system 926 to yield a purified acetylene gas product 932. The purified acetylene gas product 932 is available for use in further industrial processes, such as the synthesis of vitamin products depicted in FIGS. 18 and 19.

Using the systems and methods disclosed herein, acetylene and hydrogen can be produced on-site from natural gas or other hydrocarbon raw materials to be used for vitamin and provitamin manufacturing. These systems and methods can allow vitamin manufacturers to control their own acetylene production capacity and rates of resource utilization while providing an acetylene source of high purity.

Figure 20:
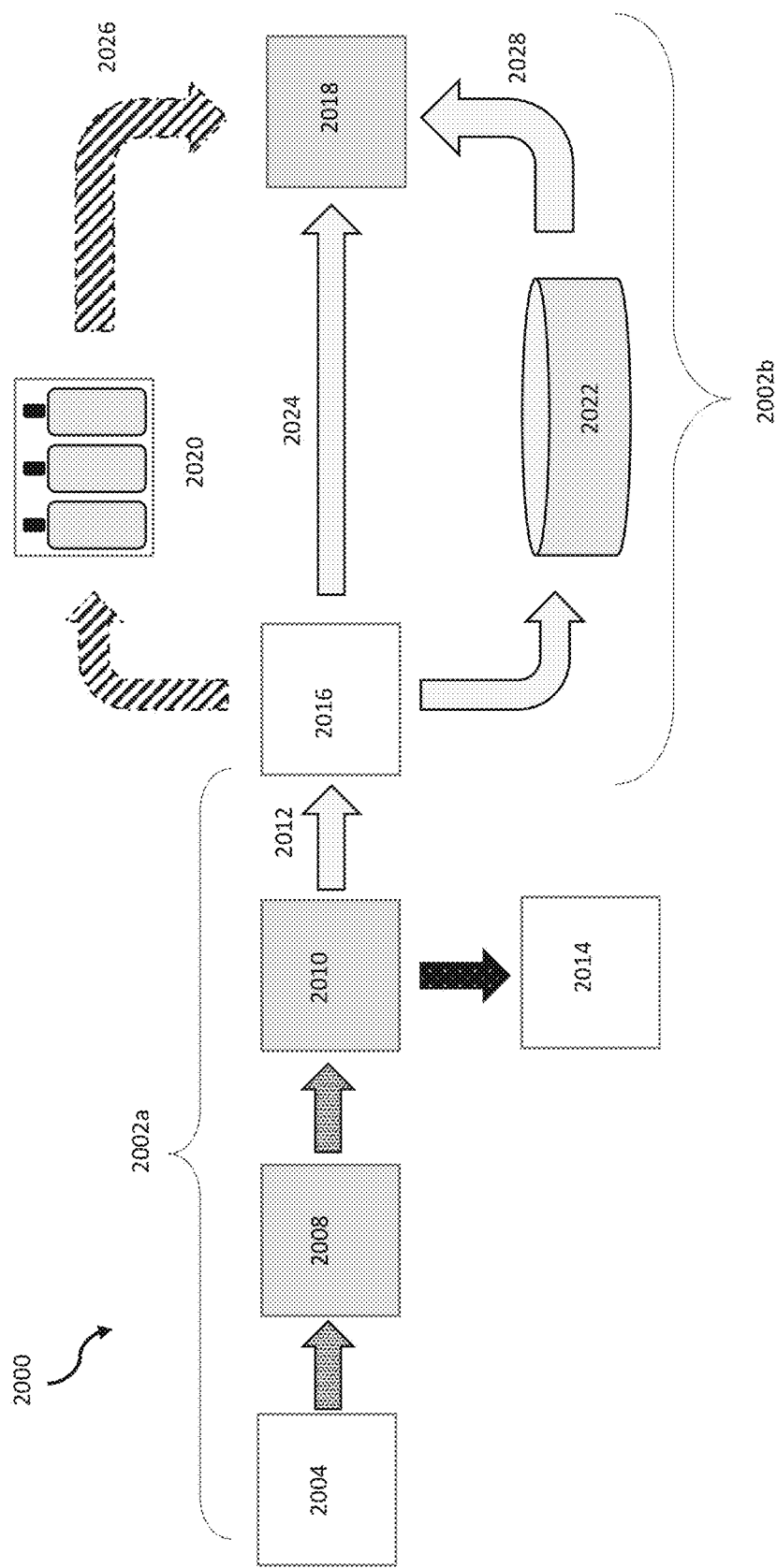
FIG. 20 is a block diagram showing steps of a process for producing vitamin products using acetylene.

FIG. 20 depicts a general scheme showing the steps of the process for producing vitamin products 2000, using acetylene and hydrogen produced by a plasma-based hydrocarbon processing system as has been disclosed herein. Note that the scheme shown in FIG. 20 can take advantage of a variety of plasma-based hydrocarbon processing systems such as have been disclosed herein, whereby acetylene and/or hydrogen is produced using such a system, and whereby the gas(es) so produced are then used, in whole or in part, for producing vitamin products. Pathway 2002a shows the steps for producing acetylene from raw materials in accordance with these systems and methods. As an initial step, raw materials are provided 2004 for further processing, wherein the raw materials comprise a hydrocarbon-containing inflow gas, and can further comprise a recycled gas. The raw materials are then processed 2008 into outflow gas products comprising acetylene, hydrogen, and acetylene byproducts in a reactor having a gas delivery subsystem, a plasma reaction chamber, and a microwave subsystem, as described previously, with the acetylene, hydrogen, and byproducts exiting the reactor to enter a set of separators for further separation and purification steps 2010. In embodiments, the step of processing 2008 comprises the steps (not shown) of injecting the hydrocarbon-containing inflow gas into the plasma reaction chamber; energizing the hydrocarbon-containing inflow gas in the plasma reaction chamber with microwave energy to create a plasma; forming outflow gas products in the plasma, wherein the outflow gas products comprise acetylene and hydrogen; flowing the outflow gas products to exit the plasma reaction chamber, whereupon the outflow gas products are processed with a set of separation and purification steps 2010. The separation and purification steps 2010, comprising the steps of effluent separation, acetylene separation, and hydrogen separation, yield a set of component gases comprising a pure acetylene product 2012, which pure acetylene product 2012 then is distributed 2016 so that it enters a process for vitamin manufacturing 2018.

The separation and purification steps also produce off-gases 2014 such as acetylene byproducts and pure hydrogen that are removed or isolated from the pure acetylene product 2012.

As mentioned above, the pure acetylene product 2012 produced by the separation and purification steps 2010 is distributed 2016 for further use in vitamin manufacture 2018. The pure acetylene can be distributed 2016 for this purpose via direct delivery 2024 (i.e., without any intermediate diversions or sequestrations of gas); in addition, the pure acetylene product 2012 can be distributed 2016 for storage 2022, or for a commercialization process 2020 such as bottling, with either of these destinations available to be subsequently used for vitamin manufacturing 2018 (as shown in paths 2026 and 2028). The distribution process 2016 is intended to optimize the utilization of the acetylene produced by the plasma-based hydrocarbon processing pathway 2002a by adjusting the inflow of the acetylene 2012 produced though this pathway 2002a to conform to the needs of the process for vitamin manufacturing 2018, for example, via a feedback mechanism whereby the inflow of the acetylene 2012 is increased or decreased depending on a measurement for requisite acetylene provided by the vitamin manufacturing system. The steps shown by the pathways within 2002b illustrate ways by which pure acetylene 2012 produced by the plasma-based hydrocarbon processing pathway 2002a can enter the synthetic process for manufacturing vitamin products 2018. One option involves acetylene bottling 2020, wherein the pure acetylene 2012 is bottled in a compressed form and delivered 2026 to the manufacturing plant for subsequent use in producing vitamin products 2018. Acetylene bottling 2020, familiar in the art, is well known to have commercially important drawbacks however, including safety concerns and logistical difficulties. A second option involves the storage of the acetylene in a gas holding tank 2022 at near atmospheric pressure, with subsequent delivery 2028 for vitamin manufacture 2018. While this approach offers advantages compared to acetylene bottling 2020, safety concerns and logistical difficulties still exist. Direct delivery 2024 of pure acetylene 2012 for vitamin manufacture 2018 is a highly desirable option. Using the systems and methods disclosed herein and illustrated in the Figure to follow, a predictable source of highly purified acetylene 2012 can be provided for use in vitamin manufacture 2018, desirably via direct delivery 2024 into vitamin manufacturing processes 2018.

Figure 21:
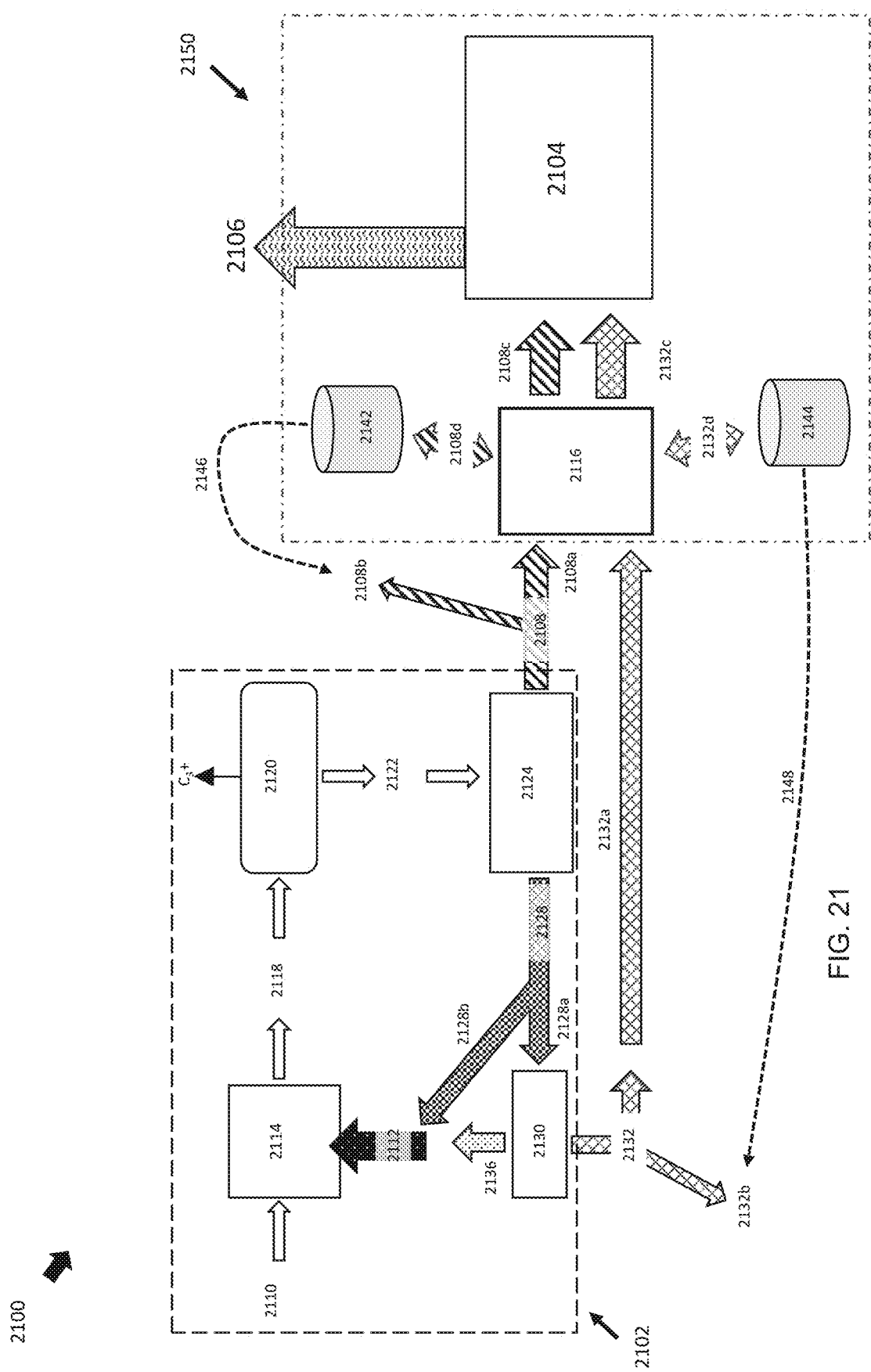
FIG. 21 is a schematic diagram of an integrated system for vitamin manufacturing.

FIG. 21 shows in more detail how the systems and methods disclosed herein can be integrated with systems and processes for manufacturing vitamin products. In embodiments, this Figure illustrates how the systems and methods disclosed herein efficiently produce a highly purified acetylene that is suitable for direct and/or controllable delivery to the manufacturing processes, and how the systems and methods disclosed herein can optimize delivery of acetylene to vitamin manufacturing systems and processes in keeping with the variable demands of these processes, while minimizing the need for ancillary storage facilities.

FIG. 21 shows an embodiment of an integrated acetylene-based vitamin synthesis system 2100 in which a plasma-based hydrocarbon processing system 2102 as described herein interfaces with a system 2150 for manufacturing vitamin products 2106, for example, the vitamin products or precursors thereof shown in the synthetic diagrams in FIGS. 18 and 19. In the depicted embodiment, the vitamin manufacturing system 2150 comprises a vitamin reaction plant 2104, a controlling system (or "controller") 2116, an acetylene receptacle 2142, and a hydrogen receptacle 2144. In the depicted embodiment: (i) the reactions described in FIG. 18 and FIG. 19 for manufacturing of vitamin products 2106 are carried out by suitable reactors (not shown) within the vitamin reaction plant 2104; (ii) the acetylene receptacle 2142 and the hydrogen receptacle 2144 are available to store acetylene and hydrogen gases that are produced by the plasma-based hydrocarbon processing system 2102 or that are obtained from other sources; and (iii) the controller 2116 controls the flow of acetylene and hydrogen from the plasma-based hydrocarbon processing system 2102 into the vitamin reaction plant 2104 and/or the receptacles 2142 and 2144 as needed. While the depicted embodiment includes the receptacles 2142 and 2144, it is understood that the plasma-based hydrocarbon processing system 2012 as disclosed herein can also provide acetylene and/or hydrogen for direct delivery as described above, without a need for receptacles or other containers for storing excess gas. In such an embodiment, the controller 2116 controls the flow of acetylene and hydrogen from the plasma-based hydrocarbon processing system 2102, for example, from the acetylene and hydrogen separators, respectively, into the vitamin reaction plant 2104 without intermediate diversions or sequestrations of gas(es). It is further understood that other arrangements or components for the vitamin manufacturing system 2150 can be envisioned by skilled artisans as embodiments of an integrated acetylene-based vitamin synthesis system 2100 employing the plasma-based hydrocarbon processing system 2102 as described herein.

In more detail with reference to FIG. 21, the plasma-based hydrocarbon processing system 2102 yields a highly purified acetylene product 2108 that can be delivered into the system 2150 for manufacturing vitamin products 2106. In the depicted embodiment, the plasma-based hydrocarbon processing system 2102 comprises a hydrocarbon inflow stream 2110 (e.g., natural gas) and a recycled gas stream 2112, a microwave reactor 2114 comprising a plasma reaction chamber (not shown) into which the hydrocarbon inflow stream 2110 and the recycled gas stream 2112 are delivered, wherein they are energized by a microwave subsystem (not shown) to form a plasma that yields chemical products that emerge from the plasma chamber to form an outflow stream 2118 of outflow gas products, all as have been described above in detail. In the depicted embodiment, the outflow stream 2118 is subjected to further processing and separation, including passage through a set of separator subsystems.

The set of separator subsystems, all of which have been described previously in more detail, include: (i) an effluent separator 2120 for the removal of higher acetylenes and aromatic impurities ($C_3^+$) (using for example, a temperature swing adsorber or a prescrubber), yielding a purified effluent stream 2122; (ii) an acetylene separator 2124 for the separation of the highly purified acetylene product 2108 from the purified effluent stream 2122 via acetylene purification columns or the like, to yield a remaining effluent stream 2128; and (iii) a hydrogen separator 2130 (e.g., a pressure swing absorber or a membrane separator).

The embodiment shown in FIG. 21 provides one sequencing of the separator steps and subsystems. In the depicted embodiment, the remaining effluent stream 2128 divides into two streams, 2128a and 2128b. The first remaining effluent stream 2128a undergoes further treatment in the hydrogen separator 2130, with the purified hydrogen product 2132 being separated therefrom. The other remaining effluent stream 2128b is diverted before entering the hydrogen separator 2130 and instead is recycled, forming a recycled gas stream 2112 (either alone or, as depicted, in conjunction with other gas streams such as the residual gas stream 2136 exiting the hydrogen separator 2130), with the recycled gas stream 2112 being available for use in the microwave reactor 2114 as described previously. The residual gas stream 2136 can be used to form the recycled gas stream 2112, either blended with other recyclable gas streams such as the remaining effluent stream 2128b (as depicted in this Figure) and/or combined with other gas streams (not shown), or used alone to form the recycled gas stream 2112.

Purified hydrogen product 2132 can be directed in a dedicated hydrogen stream 2132a for ultimate use in the vitamin reaction plant 2104; alternatively, purified hydrogen product 2132 can be directed away from the vitamin manufacturing system 2150 in an external hydrogen stream 2132b for separate sale, storage, or disposal. In more detail, the purified hydrogen product 2132a can be directed by the controller 2116 to a holding tank or other receptacle 2144 for use in the vitamin reaction plant 2104. The receptacle 2144 can be configured as a holding tank for temporary storage, wherein the purified hydrogen 2132d resides for a preselected period of time based on the needs of the overall vitamin manufacturing system 2150. Similarly, the purified acetylene product 2108 can be directed in a dedicated acetylene stream 2108a for use in the vitamin reaction plant 2104; alternatively, purified acetylene product 2108 can be directed away from the vitamin manufacturing system 2150 in an external acetylene stream 2108b for separate sale, storage, or disposal. In more detail, the purified acetylene product 2108a can be directed to a holding tank or other receptacle 2142 for use in the system for manufacturing vitamin products. The receptacle 2142 can be configured as a holding tank for temporary storage, wherein the purified acetylene 2108d resides for a preselected period of time based on the needs of the overall vitamin manufacturing system 2150.

In embodiments, a controller 2116 is positioned to receive acetylene and hydrogen from (respectively) the dedicated acetylene stream 2108a and the dedicated hydrogen stream 2132a, and to deploy these reactants for use in the vitamin manufacturing system 2150. As shown in the schematic, the controller 2116 can pass the purified acetylene 2108 into the vitamin reactor plant 2104 via an acetylene inflow stream 2108c, wherein the acetylene inflow stream 2108c contains the purified acetylene product 2108 produced by the plasma-based hydrocarbon processing system 2102. In addition or alternatively, the controller 2116 can divert some or all of the purified acetylene 2108 into the receptacle 2142 for temporary storage via a storage circuit 2108d, and the controller can direct the release of purified acetylene from the receptacle 2142 via the storage circuit 2108d so that it enters the acetylene inflow stream 2108c for use in the vitamin reactor plant 2104 to produce vitamin products 2106. Similarly, as shown in the schematic, the controller 2116 can pass the purified hydrogen 2132 into the vitamin manufacturing system 2104 via a hydrogen inflow stream 2132c, wherein the hydrogen inflow stream 2132c contains the purified hydrogen product 2132 produced by the plasma-based hydrocarbon processing system 2102. Additionally or alternatively, the controller 2116 can divert some or all of the purified hydrogen 2132 into a receptacle 2144 for temporary storage via a storage circuit 2132d, and the controller can direct the release of purified hydrogen from the receptacle 2144 via the storage circuit 2132d so that it enters the hydrogen inflow stream 2132c for use in the vitamin reactor plant 2104 to produce vitamin products 2106. Each receptacle 2142 and 2144 can further be in fluid communication with the external stream for its respective gas contents (for acetylene, 2108b, and for hydrogen 2132b), via an offload conduit (shown as the dashed line 2146 for acetylene and the dotted line 2148 for hydrogen).

Purified acetylene 2108 that is stored in the receptacle 2142 can be dissolved in a solvent within the receptacle 2142, for example, solvents such as N-methyl pyrrolidone, and dimethylformamide, and/or liquid ammonia. In embodiments, the acetylene gas 2108d directed to the receptacle 2142 is compressed before reaching the receptacle 2142 via a compressor (not shown), so that the receptacle 2142 can provide sufficient storage for the manufacturing facility's needs in a smaller space. In embodiments, the acetylene gas 2108d can be compressed via a compressor (not shown) into the receptacle 2142 along with an inert carrier gas or a non-inert gas such as gaseous ammonia, or the acetylene gas 2108d can be compressed into the inert carrier gas or non-inert gas such as gaseous ammonia that is already contained in the receptacle 2142. In embodiments, the acetylene 2108a can be directed by the controller 2116 to bypass the receptacle 2142 and be directed as a direct delivery distribution via the acetylene inflow stream 2108c into the vitamin reactor plant 2104; in other embodiments, the acetylene 2108 needed for various steps of vitamin synthesis is obtained from the acetylene stored in the receptacle 2142, with said acetylene being directed by the controller 2116 from the receptacle 2142 into the vitamin reactor plant 2104 via the acetylene inflow stream 2108c, as controlled by the controller 2116. It is understood that the controller 2116 can control the inflow 2108c of acetylene for vitamin manufacture that is provided from any available source, including any combination of the plasma-based hydrocarbon processing system 2102, the acetylene receptacle 2142, and any other source (not shown) providing acetylene of appropriate purity for vitamin manufacture. A similar set of options is available for hydrogen, so that the hydrogen 2132a can be directed by the controller 2116 to bypass the receptacle 2144 and be directed as a direct delivery distribution via the hydrogen inflow stream 2132c into the vitamin reactor plant 2104; in other embodiments, the hydrogen 2132 needed for various steps of vitamin synthesis is obtained from the hydrogen stored in the receptacle 2144, with said hydrogen being directed by the controller 2116 from the receptacle 2144 into the vitamin reactor plant 2104 via the hydrogen inflow stream 2132c, as controlled by the controller 2116. It is understood that the controller 2116 can control the inflow 2132c of hydrogen for vitamin manufacture from any available source, including any combination of the plasma-based hydrocarbon processing system 2102, the hydrogen receptacle 2144, and any other source (not shown) providing hydrogen of appropriate purity for vitamin manufacture.

In embodiments, the controller 2116 contains a feedback loop or similar processing system(s) that modulate the rate of processes carried out by the plasma-based hydrocarbon processing system 2102 in order to allow for just-in-time production of purified acetylene 2108 or hydrogen 2132 as required by the vitamin manufacturing system 2104; for example, in embodiments, the controller 2116 permits intermittent production of purified acetylene 2108 or hydrogen 2132, or controls the rate of their production or controls their diversion outside the system, for example, into external streams for acetylene 2108b or hydrogen gas 2132b. In embodiments, the controller 2116 can regulate the amount of hydrogen that is extracted by the hydrogen separator 2130 from the remaining effluent stream 2128a, and/or the controller can regulate the volume of the remaining effluent stream 2128 that is diverted 2128b to comprise the recycled gas stream 2112. Other interfaces between the controller 2116 and the plasma-based hydrocarbon processing system 2102 can be envisioned by skilled artisans in order to synchronize the needs of the vitamin reactor plant 2104 with the output from the plasma-based hydrocarbon processing system 2102.

As further exemplification, in embodiments, a number of variations to the system 2100 can be implemented in order to allow for intermittent production, just-in-time production, or interrupted production of acetylene and/or hydrogen for vitamin manufacturing. As shown in FIG. 21, the hydrocarbon inflow stream 2110 is energized in the microwave reactor 2114 along with the recycle gas 2112, producing acetylene and hydrogen in the outflow stream 2118. As shown, the outflow stream 2118 is further processed to provide purified acetylene 2108 for the vitamin manufacturing system 2150. If it is necessary to stop production of acetylene and hydrogen, for example, if throughput of the gas(es) is not required for vitamin manufacture and/or sufficient gas(es) have been provided for vitamin manufacture and capacity of the receptacles 2142 and/or 2144 is not adequate for storing the excess gases, the microwave reactor 2114 can be powered down to stop the production of acetylene and hydrogen, including as applicable shutting off the delivery of hydrocarbon-containing inflow gas 2110. Following such a shutdown, the recycle gas 2112 can be simply recirculated (not shown) within the system 2102. In other embodiments, the recycle gas 2112 that is recirculated can also bypass one or more purifications steps (e.g., 2120, 2124, and 2130) if needed. In a preferred embodiment, the recirculating recycle gas bypasses 2124 and 2130, and the exiting gases (2128 and 2108) from the acetylene purification columns 2124 are re-circulated to re-enter the acetylene purification columns 2124. Gas flow pathways and operating conditions to dissociate the plasma-based hydrocarbon processing system 2102 from the vitamin manufacturing system 2150 can be coordinated based on the vitamin manufacturing system's needs or on other preselected parameters.

In embodiments, the controller 2116 accomplishes this coordination. The interaction of the components of the integrated acetylene-based vitamin synthesis system 2100 as mediated by the controller 2116 allows the supply side of the system (i.e., the plasma-based hydrocarbon processing system 2102) to respond quickly to the requirements from the demand side of the system (i.e., the vitamin manufacturing system 2150), for example, rapidly changing the volume of acetylene produced, or starting/stopping the production and delivery of acetylene and hydrogen to the vitamin reactor plant 2104 as needed, or diverting more or less of the hydrogen-containing remaining effluent stream 2128 for recycling 2112.

Steps for the manufacture of Vitamins A and E and their precursors are familiar to artists of ordinary skill in the art, with the plasma-based hydrocarbon processing system 2102 as described herein providing some or all of the acetylene and/or hydrogen used in those manufacturing processes. Therefore, the synthetic processes for the manufacture of vitamin products 2106 that have been described previously in FIGS. 18 and 19 are not depicted in FIG. 21. However, as an example of how the systems of FIG. 21 can perform the synthetic processes of FIGS. 18 and 19, a series of reactors (not shown) can be disposed within the vitamin reactor plant 2104 and can be charged with appropriate reagents to carry out the reactions as shown in FIG. 18 and FIG. 19, as would be understood by artisans of ordinary skill. The acetylene and hydrogen to be delivered into those reactors can be preliminarily compressed (not shown) as necessary. In embodiments, reaction paths can be provided within the vitamin manufacturing system 2150 to provide acetylene and/or hydrogen for one or more of the depicted reactions as shown in FIG. 18 and FIG. 19, for example, ethynylation reactions and hydrogenation reactions as required by the steps in the synthetic pathways, with isolation of reaction products and further ethynylation and/or hydrogenation thereof in accordance with the steps in the synthetic pathways.

Figure 22:
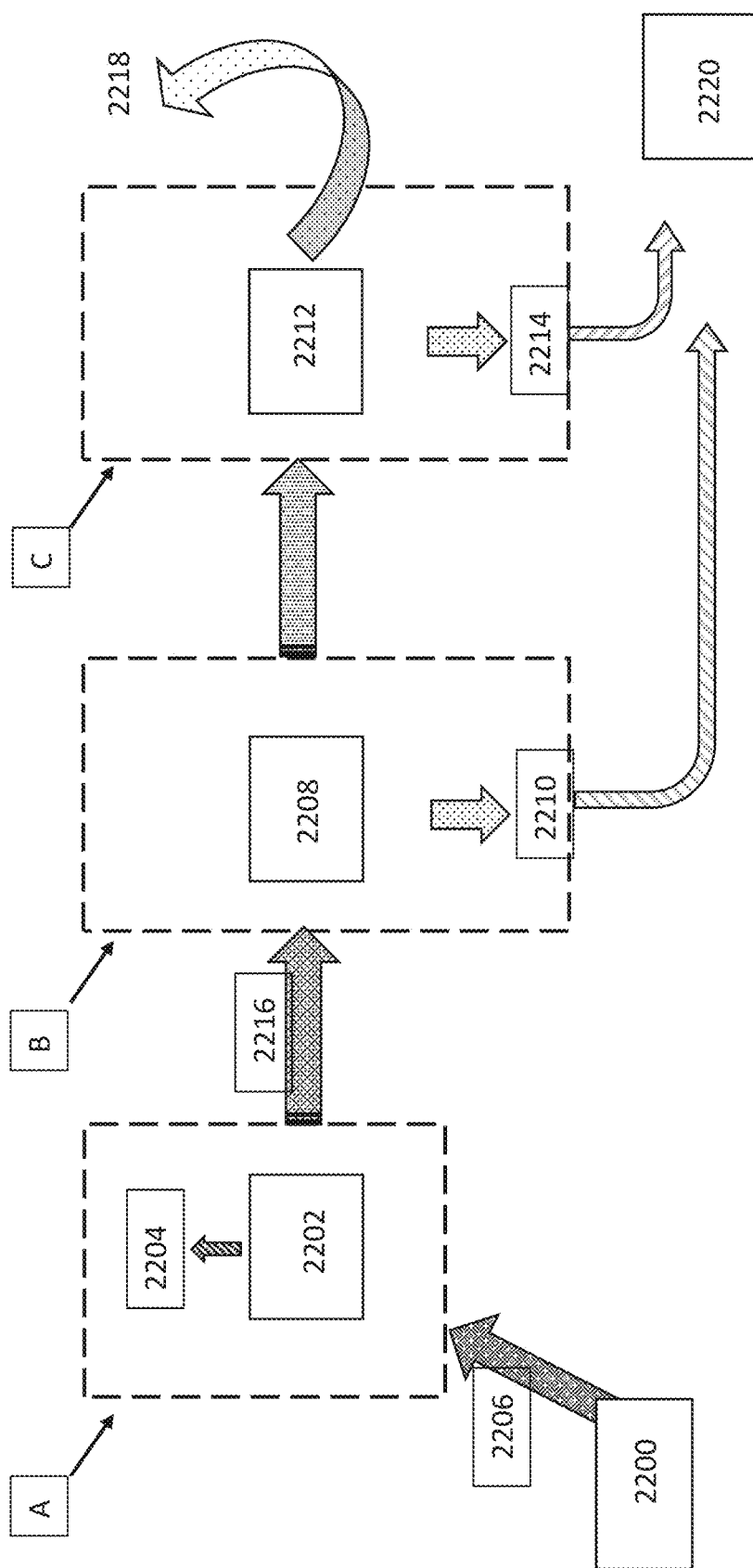
FIG. 22 is a block diagram illustrating features of an integrated system for vitamin processing.

While FIG. 20 and FIG. 21 show a particular order of the separator subsystems, it is understood that, in other embodiments, the ordered position of the effluent separator, the acetylene separator, and the hydrogen separator can be rearranged. FIG. 22 shows one arrangement of these components. As illustrated in FIG. 22, inflow 2206 from the plasma-based hydrocarbon processing system 2200 described above first enters (i) an effluent separator 2202 for removal of higher acetylenes and aromatic impurities 2204 (collectively forming Block A in the Figure) as described above, forming an effluent stream 2216 without higher acetylenes and aromatic impurities. The effluent separator 2202 is in fluid communication with (ii) an acetylene separator 2208, which receives the effluent stream 2216 and removes a purified acetylene product 2210 therefrom (collectively forming Block B in the Figure) as described above. The acetylene separator 2208 in turn is in fluid communication with (iii) a hydrogen separator 2212 for removal of a purified hydrogen product 2214 (collectively forming Block C in the Figure), with any residual gas depicted as remaining gas 2218. As depicted, remaining gas 2218 can be recycled for further use in the plasma-based hydrocarbon processing system 2206. This arrangement has been described above and illustrated in FIGS. 20 and 21. As has been previously described, the purified hydrogen product 2210 and the purified acetylene product 2214 are suitable for use in the vitamin manufacturing system 2220. Other arrangements of the depicted blocks are also compatible with the systems and methods disclosed herein. In embodiments, for example: Block A ($C^+$ separation) can precede Block C ($H_2$ separation), which precedes Block B ($C_2H_2$ separation); Block C ($H_2$ separation) can precede Block A ($C^+$ separation), which precedes Block B ($C_2H_2$ separation); or Block C ($H_2$ separation) can precede Block B ($C_2H_2$ separation), which is followed by Block A ($C^+$ separation), with any recycling based on the ordering of the blocks. In embodiments, one or more of the Blocks can be omitted. For example, if pure hydrogen is provided into the system from an external source, hydrogen separation (Block C) can be omitted. Or, for example, a vitamin manufacturing system can have a lower purity requirement than is provided by these systems and methods, in which case Block A ($C^+$ separation) can be omitted. In other embodiments, hydrogen can be provided from an external source to the vitamin manufacturing system and a lower purity for acetylene is satisfactory for use; in this case, only Block B ($C_2H_2$ separation) is required.

c. Acetylene Decomposition

As another example, the acetylene produced by the plasma-based hydrocarbon processing system can be used as a precursor for acetylene decomposition processes, which yield hydrogen gas and acetylene black. A plasma-based hydrocarbon processing system as described above can be modified so that it maximizes and optimizes the acetylene produced, and the system can be integrated with processes required to convert the acetylene into hydrogen gas and acetylene black. In embodiments, a plasma-based hydrocarbon processing system for producing acetylene, as described above, can deliver this product as a feedstock into an acetylene decomposition subsystem for further processing, so that a fully integrated industrial application is constructed that incorporates precursor production (i.e., acetylene produced by the plasma-based hydrocarbon processing system) and precursor utilization to form the desired product, which can be either acetylene black or hydrogen, with the simultaneous production of either hydrogen gas or acetylene black (respectively) as a useful byproduct. Using the systems and methods disclosed herein, acetylene can be produced on-site from natural gas or other hydrocarbon raw materials to be used for acetylene decomposition, with production of acetylene black and hydrogen. These systems and methods can allow manufacturers to control their logistics and rates of resource utilization by taking advantage of an integrated acetylene source of high purity.

Figure 23:
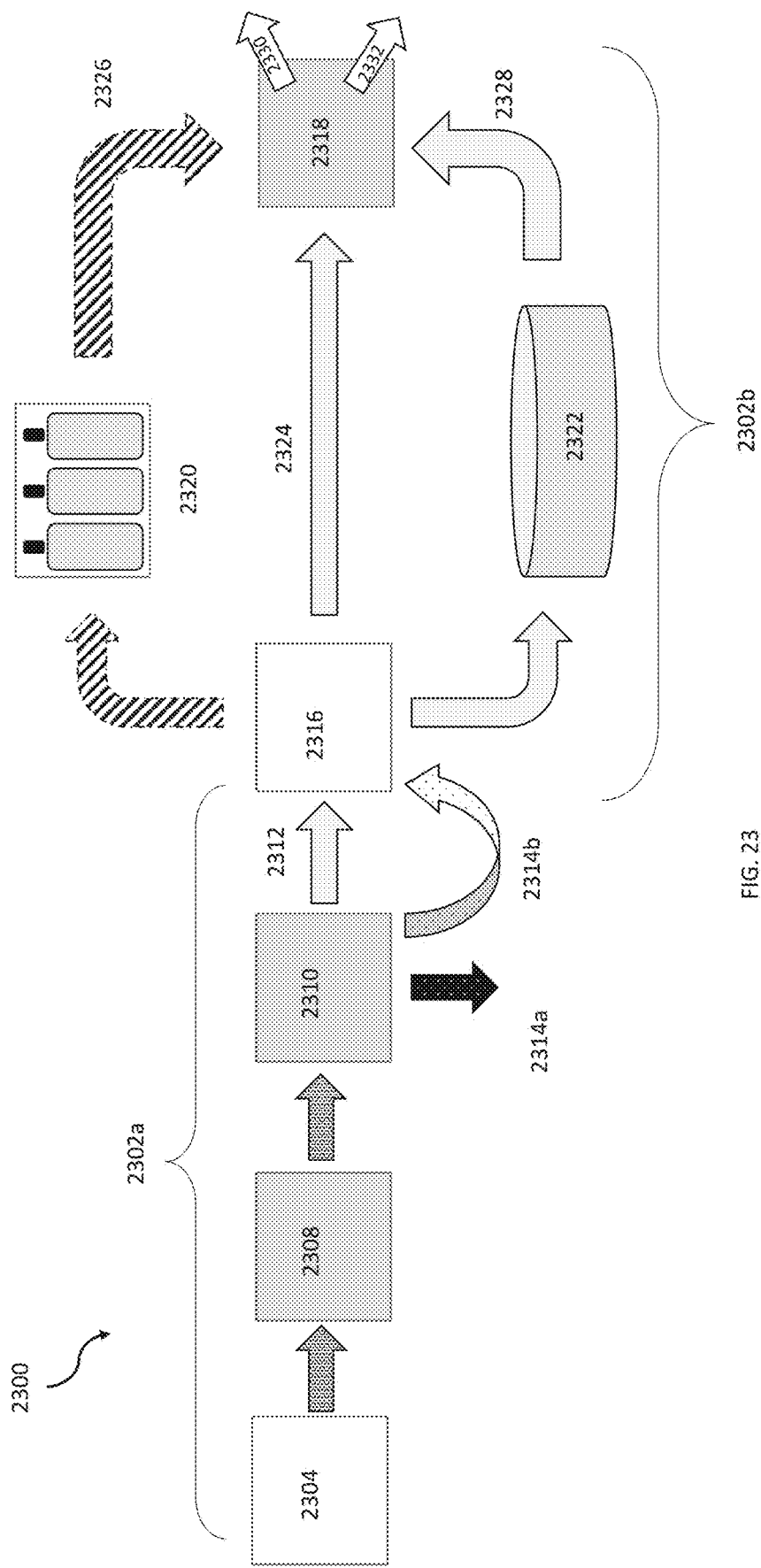
FIG. 23 is a block diagram showing steps of a process for producing acetylene black using acetylene or an acetylene-rich gas.

FIG. 23 provides a block diagram showing a general scheme with a series of steps for the process 2300 for producing acetylene black and hydrogen, using the acetylene produced by the plasma-based hydrocarbon processing system that has been disclosed herein. Note that the scheme shown in FIG. 23 can take advantage of a variety of plasma-based hydrocarbon processing systems such as have been disclosed herein, whereby acetylene is produced using such a system, and whereby the gas so produced is then used, in whole or in part, for producing acetylene black and/or hydrogen.

Pathway 2302a shows the steps for producing acetylene from raw materials using a plasma-based hydrocarbon processing system as previously disclosed. As an initial step in the process 2300, raw materials are provided 2304 for further processing, wherein the raw materials comprise a hydrocarbon-containing inflow gas, and can further comprise a recycled gas. The raw materials are then processed 2308 into outflow gas products comprising acetylene, hydrogen, and acetylene byproducts using a reactor having a gas delivery subsystem, a plasma reaction chamber, and a microwave subsystem, as described previously, with the acetylene, hydrogen, and byproducts exiting the reactor to enter a set of separators for further separation and purification steps 2310. In embodiments, the step of processing 2308 comprises the steps (not shown) of injecting the hydrocarbon-containing inflow gas into the plasma reaction chamber; energizing the hydrocarbon-containing inflow gas in the plasma reaction chamber with microwave energy to create a plasma; forming outflow gas products in the plasma, wherein the outflow gas products comprise acetylene and hydrogen; flowing the outflow gas products to exit the plasma reaction chamber, whereupon the outflow gas products are processed with a set of separation and purification steps 2310. The separation and purification steps 2310, comprising the steps of effluent separation, acetylene separation, and hydrogen separation, yield a set of component gases comprising an acetylene-rich gas stream 2312, which stream 2312 then is distributed 2316 so that it enters a process for manufacturing acetylene black 2302b. The separation and purification steps also produce off-gases such as acetylene byproducts and pure hydrogen that are removed 2314a from the acetylene-rich stream 2312, or are, in whole or in part, rejoined 2314b to enter the manufacturing process 2302b with the acetylene-rich stream 2312 as feedstock for the acetylene decomposition reactor 2318 that produces acetylene black 2330 and hydrogen 2332 from the acetylene in the acetylene-rich stream 2312. The hydrogen that is part of the offgas stream 2314a produced by the separation and purification steps can be all, or in part, recycled (not shown) back to the beginning of the pathway 2302a, as a recycled gas stream that becomes one of the raw materials 2304 for the plasma-based hydrocarbon processing system. In embodiments, hydrogen from the offgas stream 2314a can, all or in part, directly or indirectly, be collected as a desired, final product.

A separation system using adsorbers, as discussed above, is well suited for producing an acetylene-rich stream 2312 that can be distributed 2316 into the process for manufacturing acetylene black 2302b. As shown in this Figure, the separation and purification steps 2310 process the outflow gas products so that the acetylene-rich stream 2312 can be separated from the off-gases (whether removed from the system 22314a or rejoined 2314b to enter the manufacturing process 2302b), yielding just an acetylene-rich stream 2312 that provides the feed for the acetylene decomposition reactor 2318. The specific nature of the acetylene-rich stream 2312, however, can be engineered to meet the needs of the acetylene decomposition reactor 2318 and related processes, as shown schematically in the process for manufacturing acetylene black 2302b.

In embodiments, it may be advantageous to use an acetylene separator (not shown) to carry out the separation and purification steps 2310, such as a short-cycle TSA with or without a standard TSA, as described above. In such an arrangement, the higher acetylenes captured by a short-cycle TSA (for example, with no standard TSA) can be passed into the manufacturing process 2314b to be processed along with the acetylene-rich stream 2312 to reach the acetylene decomposition reactor 2318. In embodiments, for example, if the acetylene black produced has favorable properties when no higher acetylenes are used, or if the extended regeneration time of a short-cycle TSA operated without a TSA scrubbing step introduces disadvantages, a standard TSA can be operated before the short-cycle TSA so that a substantially pure acetylene-rich stream 2312 is used. Other acetylene separation methods that provide acetylene at purities above 90% such as absorption column systems can also be used. Depending on the quality of acetylene black product desired, acetylene at lower purities can be used as well, for example by providing a stream comprising the higher acetylenes captured by a short-cycle TSA with no standard TSA to enter the manufacturing process 2314b either alone or to be processed along with the acetylene-rich stream 2312 to reach the acetylene decomposition reactor 2318.

Optionally, accelerating species can be added to compensate for the less reactive stream (either stream 2314b alone or stream 2314b admixed with the acetylene-rich stream 2312). Balancing the levels of limiting and accelerating species is important for the production of high quality acetylene black and hydrogen from an impure acetylene stream. Some limiting species such as methane, ethylene, and propadiene are found in an impure stream and can decompose endothermically. Other limiting species such as hydrogen and nitrogen can be found in an impure stream, but do not permanently decompose. However, limiting species will sap heat from the reaction, changing the character of the acetylene black produced; when in excess they can cool the process far enough to halt the reaction. Thus limiting species are to be avoided in the acetylene-rich stream 2312. Accelerating species in an acetylene mixture will tend to add heat the reaction and will also change the character of the acetylene black produced. When present in excess they can allow the gas mixture to decompose spontaneously or in response to minor provocation leading to concerns of safety and reliability. For example, accelerating species such as higher acetylenes release more energy than acetylene as they decompose. Others, such as oxidizers, increase the rate of the reaction. Both limiting and accelerating species can be present in the feed stream 2312 and balanced against one other for further control of the characteristics of the acetylene black produced.

Via the reactions depicted in Pathway 2302a in FIG. 23, the plasma-based hydrocarbon processing system produces acetylene and hydrogen in a stoichiometric 1:3 ratio from methane, the primary constituent of natural gas. The acetylene decomposition reaction entailed in the manufacture of acetylene black 2302b produces one mol of hydrogen 2332 for each mol of acetylene reacted, along with the acetylene black itself 2330. Therefore, by converting the acetylene produced from methane by the plasma-based hydrocarbon processing system (as has been disclosed herein) into hydrogen and acetylene black, the total hydrogen produced is increased by a third, to four mols of hydrogen gas for every two mols of methane. Thus this system is advantageous for producing hydrogen: besides the hydrogen produced by the plasma-based hydrocarbon processing system (shown here as the hydrogen-containing offgas that is removed 2314a from the system and the hydrogen-containing offgas that is rejoined 2314b with the acetylene-rich stream 2312 to re-enter the acetylene black manufacturing process 2302b), the acetylene decomposition reactor 2318 produces substantial quantities of hydrogen 2332, which can be further purified if a secondary, pure hydrogen product is desired as a byproduct of acetylene decomposition or as a primary final product, with any acetylene black deemed a byproduct.

In embodiments, these systems and methods can be readily adapted for producing hydrogen as a desired final product, for example, by separating the hydrogen in the separated offgas 2314a from the acetylene byproducts. Systems and methods for producing hydrogen as a desired final product are described in more detail with reference to FIG. 24 below. In embodiments, the hydrogen gas produced by these systems and methods can in addition or alternatively be recycled into the plasma-based hydrocarbon processing system, as has been previously described. Advantageously, in contrast with hydrogen produced by other techniques such as partial oxidation of methane or natural gas, the carbon that is liberated from the feedstock in the acetylene decomposition reactor 2318 is sequestered into a second stable commodity, acetylene black 2330, instead of being liberated as carbon monoxide and ultimately as carbon dioxide, both common byproducts of certain conventional processes.

In embodiments, a feedstock other than methane can be used to produce acetylene via the plasma-based hydrocarbon processing system as disclosed herein; with such a feedstock, the ratio of hydrogen to acetylene produced will be less than 3:1 and the relative increase in total hydrogen production will be greater than one third. Additionally, the acetylene decomposition reactor that produces acetylene black from the acetylene-rich feedstock 2312 is permissive of impure acetylene streams within certain bounds, although the precise composition of the stream can affect the characteristics of the acetylene black product. A purification system that includes one or more adsorption steps, as described above, allows the careful separation of the ideal mixture of products for hydrogen and acetylene black production.

As mentioned above, the acetylene-rich stream 2312 produced by the separation and purification steps 2310 is distributed 2316 to reach the acetylene decomposition reactor 2318. The acetylene-rich stream 2312 can be distributed 2316 for this purpose via direct delivery 2324 (i.e., without any intermediate diversions or sequestrations of gas); in addition, or alternatively, the acetylene-rich stream 2312 can be distributed 2316 for storage 2322, or for a commercialization process 2320 such as bottling, with either of these destinations available to provide feedstock for the acetylene decomposition reactor 2318 (as shown in paths 2326 and 2328). The steps shown by the pathways within 2302b illustrate ways by which acetylene-rich stream 2312 produced by the plasma-based hydrocarbon processing pathway 2302a can enter the acetylene decomposition reactor 2318. In embodiments, the acetylene can be bottled 2320, wherein pure acetylene derived from the acetylene-rich stream 2312 is stored in commercial-sized bottles via dissolving in a liquid media at elevated pressure; bottled acetylene 2320 can be used as a feedstock for the acetylene decomposition reactor 2318, or it can be commercialized separately.

The distribution process 2316 is intended to optimize the utilization of the acetylene produced by the plasma-based hydrocarbon processing pathway 2302a by adjusting the inflow of the acetylene-rich stream 2312 produced though the pathway 2302a to conform to as is required by the acetylene decomposition reactor 2318, for example, via a feedback mechanism whereby the inflow of the acetylene-rich stream 2312 is increased or decreased depending on a measurement for requisite acetylene that is provided by the acetylene black manufacturing system.

As described above, these systems and methods can be optimized to maximize the amount and purity of hydrogen that is formed, here illustrated in this Figure as the hydrogen product 2332 of the acetylene decomposition reactor 2318, and as the pure hydrogen separable from the offgas removed as 2314a. More detail about the disposition of the hydrogen separable from the offgas removed as 2314a is provided below, with reference to FIG. 24.

Figure 24:
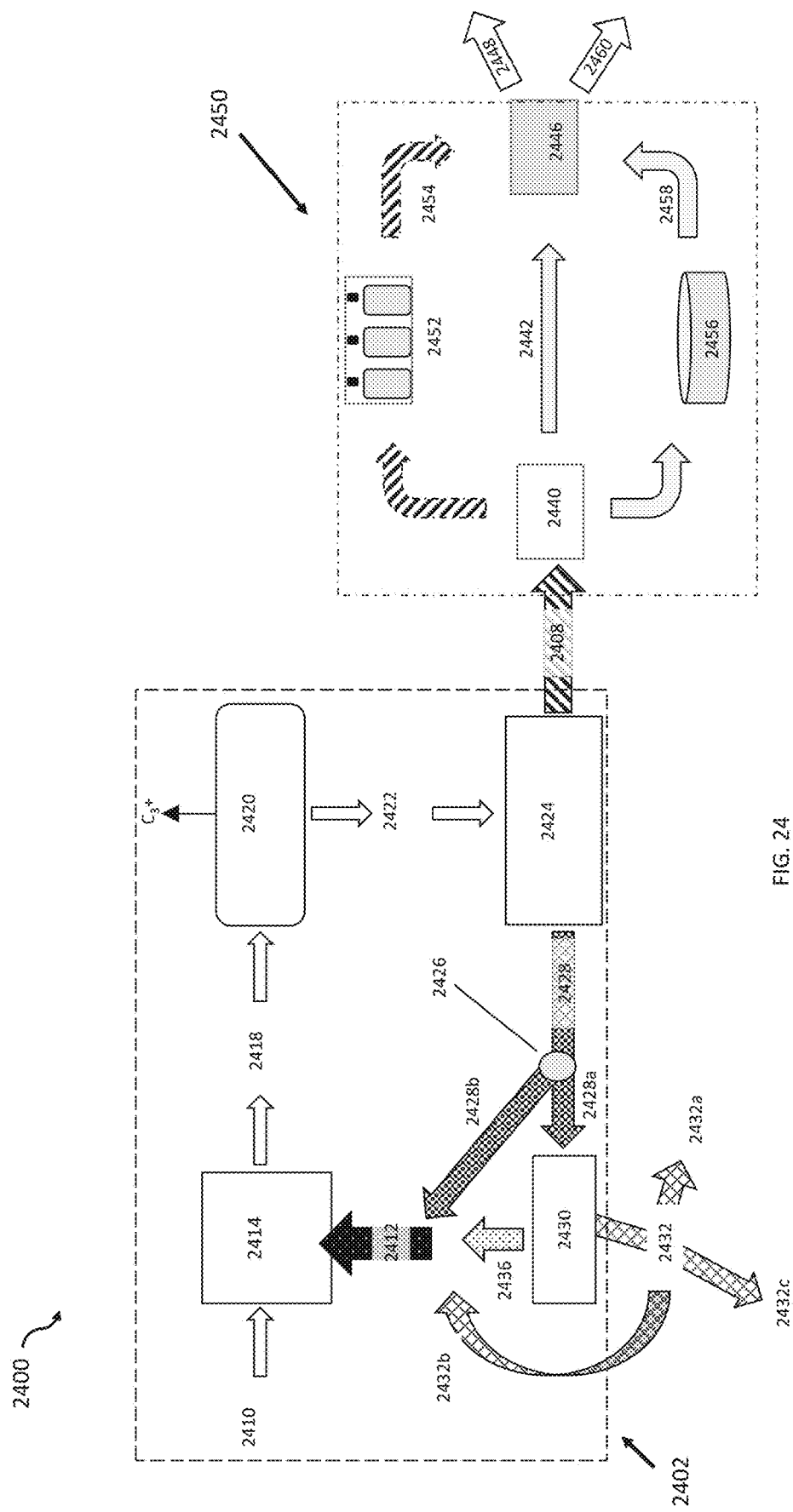
FIG. 24 is a block diagram showing steps of a process for producing hydrogen.

FIG. 24 shows in more detail how the systems and methods disclosed herein can be integrated with systems and processes for producing hydrogen as a separate, commercializable product. This Figure illustrates an embodiment of the systems disclosed herein, showing how these the systems and methods produce a highly purified acetylene that is suitable for direct and/or controllable delivery to the manufacturing processes, such as the manufacturing of acetylene black described above and/or the manufacturing of hydrogen gas. The systems and methods disclosed herein can optimize processes for producing hydrogen in concert with the manufacturing of carbon-containing products such as acetylene black.

FIG. 24 shows an embodiment of a hydrogen and acetylene production system 2400, which initially produces hydrogen gas and acetylene in a plasma-based hydrocarbon subsystem 2402 substantially similar to those plasma-based hydrocarbon subsystems described previously. The hydrogen gas produced by the plasma-based hydrocarbon subsystem 2402 can be recycled or commercialized separately, as described below. The acetylene produced by the plasma-based hydrocarbon subsystem 2402 can be commercialized separately or can be used as the feedstock for a system 2450 producing acetylene black and additional hydrogen similar to the system described above and shown in FIG. 23.

In more detail with reference to FIG. 24, the plasma-based hydrocarbon processing system 2402 yields a highly purified acetylene product 2408 that can be delivered into the system 2450 for manufacturing acetylene black. In the depicted embodiment, the plasma-based hydrocarbon processing system 2402 comprises a hydrocarbon inflow stream 2410 (e.g., natural gas) and a recycled gas stream 2412, a microwave reactor 2414 comprising a plasma reaction chamber (not shown) into which the hydrocarbon inflow stream 2410 and the recycled gas stream 2412 are delivered, wherein they are energized by a microwave subsystem (not shown) to form a plasma that yields chemical products that emerge from the plasma chamber to form an outflow stream 2418 of outflow gas products, all as have been described in detail in previous Figures. In the depicted embodiment, the outflow stream 2418 is subjected to further processing and separation, including passage through a set of separator subsystems.

The set of separator subsystems, all of which have been described previously in more detail, include, in the depicted embodiment: (i) an effluent separator 2420 for the removal of higher acetylenes and aromatic impurities ($C_3^+$) (using for example a temperature swing adsorber or a prescrubber), yielding a purified effluent stream 2422; (ii) an acetylene separator 2424 for the separation of the highly purified acetylene product 2408 from the purified effluent stream 2422 via acetylene purification columns or the like, following which a remaining effluent stream 2428 emerges from the acetylene separator; and (iii) a hydrogen separator 2430 (e.g., a pressure swing absorber, a temperature swing adsorber, or a membrane separator). The subsystems can be arranged in the order shown in FIG. 24, where the hydrogen separator 2430 is downstream from the acetylene separator 2424 and thus separates hydrogen as a highly purified hydrogen product from a remaining effluent stream 2428 from which the highly purified acetylene product 2408 has already been removed. In other embodiments, the hydrogen separator 2430 can be positioned upstream from the acetylene separator 2424, so that the hydrogen is removed from the purified effluent stream 2422 before the latter enters the acetylene separator 2424. Any hydrogen removed by the hydrogen separator 2430 (whether upstream from the acetylene separator 2424 or downstream from it) can be either isolated from the system as an integrated hydrogen stream to be used in integrated manufacturing or chemical processing, or can be isolated from the system as an external hydrogen stream for separate commercialization, storage or disposal, or can be recycled into the system as a recycled hydrogen stream, all as described below.

In more detail, FIG. 24 depicts one possible sequencing of the separator steps and subsystems. In the depicted embodiment, the remaining effluent stream 2428 is divided by a divider 2426 into two streams, 2428a and 2428b. The first remaining effluent stream portion 2428a undergoes further treatment in the hydrogen separator 2430, with the purified hydrogen product 2432 being separated therefrom, yielding a residual gas stream 2436. The second remaining effluent stream portion 2428b is diverted by the divider 2426 before entering the hydrogen separator 2430 and instead is recycled, forming a recycled gas stream 2412 (either alone or, as depicted, in conjunction with other gas streams such as the residual gas stream 2436 exiting the hydrogen separator 2430); the recycled gas stream 2412 is available for use in the microwave reactor 2414 as described previously. In embodiments, the divider 2426 can be a valve or other set of pathways that controllably directs the flow of the remaining effluent stream 2428 into one or both of the first remaining effluent stream portion 2428a and the second remaining effluent stream portion 2428b. In embodiments, the divider 2426 is an optional feature. The residual gas stream 2436 can be used to form the recycled gas stream 2412, either blended with other recyclable gas streams such as the second remaining effluent stream 2428b (as depicted in this Figure) and/or combined with other gas streams (not shown), or used alone to form the recycled gas stream 2412.

Purified hydrogen product 2432 exiting the hydrogen separator 2430 can be directed in one or more outflow streams 2432a, 2432b, and 2432c. The outflow gas streams 2432a and/or 2432c can be isolated from the overall processing system 2402, to be used in other manufacturing processes (not shown) that can be integrated with and/or in fluid communication with the overall system 2402, or to be segregated from the overall system 2402 as separate commercial products for separate sale, storage, or disposal. In more detail, one of the streams, 2432a, is an integrated hydrogen stream to be used in other integrated processes (not shown) for which hydrogen can be used as a feedstock, for example chemical manufacturing processes. As an example, the purified hydrogen product 2432 can be directed to form an integrated hydrogen stream 2432a to be combined with the purified acetylene product 2408 in other integrated processes such as have been described previously, e.g., for vitamin manufacturing. In embodiments, the purified hydrogen product 2432 can be isolated as an external hydrogen stream 2432c for separate sale, storage, or disposal. Instead of or in addition to being isolated, as shown for streams 2432a and 2432c, the purified hydrogen product 2432 can be directed as a recycled hydrogen stream 2432b to form a component of the recycling gas stream 2412 by merging, for example, with the residual gas stream 2436. It is understood that the purified hydrogen product 2432 can be directed into one or more of the subpathways 2432a, 2432b, and 2432c, in accordance with commercial requirements, including those situations in which the system 2402 is integrated with other manufacturing or storage subsystems (not shown). In embodiments, a controller (not shown) directs the purified hydrogen product 2432 in appropriate quantities along one or more preselected subpathways 2432a, 2432b, and/or 2432c.

In embodiments, recycling the hydrogen into the processing system 2402 at any point in the system that is downstream from the microwave reactor can be implemented as an advantageous alternative to recycling into or prior to the microwave reactor, so that impurities or contaminants in the recycled stream can be removed by the existing separation processes, and so that the hydrogen can be further purified by the existing purification equipment. In other embodiments, the hydrogen may be of sufficient quality so that it can be recycled into the microwave reactor to be used immediately or after being placed in a temporary storage or holding tank. As previously described, the hydrogen can be isolated instead of recycled, so that it is directed to another integrated industrial use 2342a or it is directed off-site 2432c for sale or usage, either as a gas or liquid.

Regardless of the use of the hydrogen as a desired product (as in 2432a or 2432c), it can optionally be further purified using purification processes, such as membranes, PSAs, etc. (any process known in the art) so that it is suitable for its intended use. In embodiments, the hydrogen, whether further purified or not, can be directly used in a chemical synthesis process, used as fuel for hydrogen fuel cells, burned, etc., as suggested by the subpath 2432c. In embodiments, all or part of this hydrogen stream designated for use as an integrated hydrogen stream 2432a or an external hydrogen stream 2432c, whether further purified or not, can also be stored (either as a gas or compressed into a liquid), or be transported or distributed by pipeline or container to a separate location, where the product is employed for its intended use.

As shown in FIG. 24, the acetylene-rich stream 2408 produced by the acetylene separator 2424 is distributed by a controller 2440 for further use in the process of manufacturing acetylene black and hydrogen 2450. The controller 2440 permits the distribution of the acetylene-rich stream 2408 in accordance with the requirements of the manufacturing system, whereby the acetylene-rich stream 2408 ultimately arrives at the acetylene decomposition reactor 2446, which separates acetylene into the component products of acetylene black 2448 and hydrogen 2460. Similar to those systems and methods illustrated in FIG. 23, the controller 2440 is intended to optimize the utilization of the highly purified acetylene produced by the plasma-based hydrocarbon processing pathway 2402 by adjusting the inflow of the acetylene-rich stream 2408 produced though the pathway 2402 to conform to the needs of the process for manufacturing acetylene black and hydrogen 2450, for example, via a feedback mechanism whereby the inflow of the acetylene-rich stream 2408 is increased or decreased depending on a measurement for requisite acetylene that is provided by the acetylene decomposition reactor 2446.

The acetylene-rich stream 2408 can reach the acetylene decomposition reactor 2446 via direct delivery 2442 (i.e., without any intermediate diversions or sequestrations of gas); in addition, or alternatively, the acetylene-rich stream 2408 can be distributed for storage 2456, or for a commercialization process 2452 such as bottling, with either of these destinations available to provide the acetylene-rich feedstock for use in the acetylene decomposition reactor 2446.

Similar to the system depicted in FIG. 23, the integrated hydrogen and acetylene production system shown in FIG. 24 is advantageous for producing hydrogen. Besides the hydrogen 2432 produced by the plasma-based hydrocarbon processing system, the acetylene decomposition reactor 2446 produces substantial quantities of hydrogen 2460, which can be further purified if a secondary, pure hydrogen product is desired as a byproduct of acetylene decomposition, or as a primary final product, with any acetylene black deemed a byproduct.

In embodiments, these systems and methods can be readily adapted for producing hydrogen as a desired final product. For example, the hydrogen 2432 produced by the plasma-based hydrocarbon processing system can be joined with the hydrogen 2460 produced by the acetylene decomposition reactor 2446, for any previously-described hydrogen use. For example, the hydrogen 2432 and 2460 produced from both sources can provide feedstock for a separate, integrated chemical processing plant (not shown). As another example, the hydrogen 2432 and 2460 produced by both sources can be bottled or otherwise transported to end-users, or can be distributed into the infrastructure that feeds hydrogen-equipped filling stations, such as can be used by hydrogen-powered vehicles. Other direct-to-consumer uses for the hydrogen 2432 and 2460 produced by these systems and methods can be readily envisioned by artisans in the field, with such uses expanding as the hydrogen economy gains a greater presence in the marketplace. In other embodiments, the hydrogen gas produced by these systems and methods can, in addition or alternatively, be recycled into the plasma-based hydrocarbon processing system, as has been previously described. Advantageously, in contrast with hydrogen produced by other techniques such as partial oxidation of methane or natural gas, the carbon (i.e., acetylene black 2448) that is liberated from the feedstock in the acetylene decomposition reactor 2446 is sequestered into a second stable commodity, acetylene black 2448, instead of being liberated as carbon monoxide and ultimately as carbon dioxide, both common byproducts of certain conventional processes.

EXAMPLES

Example 1

A flow of precursor gas, comprised of 60 standard liters per minute of 99.9% purity methane, 90 standard liters per minute of 99.9% purity hydrogen, and 6 standard liters per minute of nitrogen, was supplied through a gas injector apparatus similar to that described in FIGS. 4A and 4B, into an 50 mm outer diameter, 45 mm inner diameter quartz tube kept at a pressure of 70 Torr. The precursor gas was subjected to 19 kW of incident 915 MHz microwave power in a plasma reactor apparatus similar to that described in FIG. 3. 95.7% of the methane contained in the precursor gas was converted to hydrogen and hydrocarbon products. The hydrocarbon composition of the outflow gas leaving the reactor is described in Table 6 below, as analyzed by a gas chromatograph.

TABLE 6

| Component | Mol % |
|---|---|
| Acetylene | 15.12 |
| Hydrogen | 82.97 |
| Methane | 1.41 |
| Ethylene | 0.14 |
| Propane | 0.01 |
| Propadiene | 0.01 |
| Diacetylene | 0.29 |
| Vinyl Acetylene | 0.03 |
| Benzene | 0.02 |
| Carbon Solids and higher-order hydrocarbons | Trace |

The outflow gas from the reactor was passed through an air-cooled heat sink and then passed through corrugated-paper filters before exiting the vacuum pump. The outflow gas then passed through a cold trap operating at 10° C. and additional filter.

A portion of outflow gas was then passed through an adsorption column containing high surface area activated carbon. Outflow gas composition at the adsorption column exit is shown in Table 7 below.

TABLE 7

| Component | Mol Percent before Adsorption | Mol Percent after Adsorption |
|---|---|---|
| Acetylene | 15.12 | 15.17 |
| Hydrogen | 82.97 | 83.25 |
| Methane | 1.41 | 1.41 |
| Ethylene | 0.14 | 0.14 |
| Propane | 0.01 | 0.1 |
| Propadiene | 0.01 | 0.1 |
| Diacetylene | 0.29 | 0 |
| Vinyl Acetylene | 0.03 | 0 |
| Benzene | 0.02 | 0 |
| Carbon Solids | Trace | 0 |
| Higher Order Hydrocarbons | Trace | 0 |

After leaving the adsorption column, a portion of the outflow gas was then passed through an absorption column. A solvent, N-Methyl pyrrolidone, was flowed counter-currently to the outflow gas to preferentially absorb acetylene. Exiting the absorption column, the solvent with the absorbed acetylene was pumped into a second column for restoring the solvent and heated to 120-140° C. In the second column, the acetylene and associated gases were removed from the solvent as a purified product gas stream and the restored solvent was recycled into the system. Table 8 below shows the composition of the purified product gas stream emanating from the second column.

TABLE 8

| Component | Mol Percent |
|---|---|
| Acetylene | 98.764 |
| Hydrogen | 0.774 |
| Methane | 0.211 |
| Ethylene | 0.083 |
| Ethane | 0.002 |
| Propylene | 0.042 |
| Diacetylene | 0.002 |
| Vinyl Acetylene | 0.006 |
| Carbon Dioxide | 0.115 |
| Toluene | 0.001 |

Example 2

A flow of precursor gas, comprised of 20 standard liters per minute of 99.9% purity methane, 20 standard liters per minute of ethane, 95 standard liters per minute of 99.9% purity hydrogen, and 6 standard liters per minute of nitrogen was supplied through a plasma reactor apparatus as described in Example 1 and reacted with 18 kW of incident 915 MHz microwave power using the plasma reactor apparatus used in Example 1. 97.9% of the methane and ethane contained feed gas was converted to hydrogen and hydrocarbon products. The hydrocarbon composition of the outflow gas from the reactor is described in Table 9 below, as analyzed by a gas chromatograph.

TABLE 9

| Component | Mol % |
|---|---|
| Acetylene | 16.70 |
| Hydrogen | 72.73 |
| Methane | 0.75 |
| Ethylene | 0.35 |
| Propane | 0.01 |
| Propadiene | 0.01 |
| Diacetylene | 0.38 |
| Vinyl Acetylene | 0.05 |
| Benzene | 0.03 |
| Carbon Solids | Trace |
| Higher-Order HCs | |

Example 3

A flow of precursor gas, comprised of 110 standard liters per minute of 99.9% purity methane and 11 standard liters per minute of nitrogen, was supplied through a gas injector apparatus, similar to that described in FIGS. 4A and 4B, into an 80 mm outer diameter, 75 mm inner diameter quartz tube. The precursor gas was subjected to 11 kW of incident 915 MHz microwave power in a plasma reactor apparatus as described in FIG. 3. 50.7% of the methane contained in the precursor gas was converted to hydrogen and hydrocarbon products. 7% of the converted methane yielded carbon solids and polycyclic aromatic hydrocarbons. 76% of the converted methane yielded acetylene.

Example 4

A flow of precursor gas, comprised of 100 standard liters per minute of 99.9% purity methane, 160 standard liters per minute of 99.9% purity hydrogen, and 10 standard liters per minute of nitrogen, was supplied through a gas injector apparatus similar to that described in FIGS. 4A and 4B, into an 50 mm outer diameter, 45 mm inner diameter quartz tube kept at 70 Torr. The precursor gas was subjected to 29 kW of incident 915 MHz microwave power in a plasma reactor apparatus similar to that described in FIG. 3. 90.3% of the methane contained in the precursor gas was converted to hydrogen and hydrocarbon products. The hydrocarbon composition of the outflow gas leaving the reactor is described in Table 10 below.

TABLE 10

| Component | Mol % |
|---|---|
| Hydrogen | 83.42729 |
| Methane | 2.99563 |
| Propane | 0.010008 |
| Propylene | 0.010008 |
| Propadiene | 0.060046 |
| Methyl Acetylene | 0.010008 |
| 1,3-butadiene | 0 |
| Vinyl Acetylene | 0.020015 |
| Diacetylene | 0.253528 |
| Ethylene | 0.143443 |
| Ethane | 0 |
| Acetylene | 13.05334 |
| Benzene | 0.016679 |
| Toluene | 0 |

Example 5

A flow of precursor gas, comprised of 130 standard liters per minute of 99.9% purity methane, and 13 standard liters per minute of nitrogen, was supplied through a gas injector apparatus similar to that described in FIGS. 4A and 4B, into an 80 mm outer diameter, 75 mm inner diameter quartz tube kept at 48 Torr. The precursor gas was subjected to 24.3 kW of incident 915 MHz microwave power in a plasma reactor apparatus similar to that described in FIG. 3. 85.2% of the methane contained in the precursor gas was converted to hydrogen and hydrocarbon products.

Example 6

A flow of precursor gas, comprised of 74 standard liters per minute of 99.9% purity methane, 40 standard liters per minute of 99.9% purity hydrogen, and 88 standard liters per minute of nitrogen, was supplied through a gas injector apparatus similar to that described in FIGS. 4A and 4B, into an 80 mm outer diameter, 75 mm inner diameter quartz tube kept at 70 Torr. The precursor gas was subjected to 23.9 kW of incident 915 MHz microwave power in a plasma reactor apparatus similar to that described in FIG. 3. 95.1% of the methane contained in the precursor gas was converted to hydrogen and hydrocarbon products.

Example 7

A flow of precursor gas, comprised of 47 standard liters per minute of 99.9% purity methane, 110 standard liters per minute of 99.9% purity hydrogen, and 5 standard liters per minute of nitrogen, was supplied through a gas injector apparatus similar to that described in FIGS. 4A and 4B, into an 80 mm outer diameter, 75 mm inner diameter quartz tube kept at 65 Torr. The precursor gas was subjected to 15.6 kW of incident 915 MHz microwave power in a plasma reactor apparatus similar to that described in FIG. 3. 89.7% of the methane contained in the precursor gas was converted to hydrogen and hydrocarbon products.

Example 8

A flow of precursor gas, comprised of 90 standard liters per minute of 99.9% purity methane, 135 standard liters per minute of 99.9% purity hydrogen, and 9 standard liters per minute of nitrogen, was supplied through a gas injector apparatus similar to that described in FIGS. 4A and 4B, into an 38 mm outer diameter, 35 mm inner diameter quartz tube kept at 105 Torr. The precursor gas was subjected to 25 kW of incident 915 MHz microwave power in a plasma reactor apparatus similar to that described in FIG. 3. 92.0% of the methane contained in the precursor gas was converted to hydrogen and hydrocarbon products.

Example 9

A flow of precursor gas, comprised of 15 standard liters per minute of 99.9% purity butane, 90 standard liters per minute of 99.9% purity hydrogen, and 6 standard liters per minute of nitrogen, was supplied through a gas injector apparatus similar to that described in FIGS. 4A and 4B, into an 50 mm outer diameter, 45 mm inner diameter quartz tube kept at 50 Torr. The precursor gas was subjected to 17.7 kW of incident 915 MHz microwave power in a plasma reactor apparatus similar to that described in FIG. 3. 100% of the butane contained in the precursor gas was converted to hydrogen and hydrocarbon products with a 0.6% methane yield.

Example 10

A flow of precursor gas, comprised of 30 standard liters per minute of 99.9% purity ethane, 90 standard liters per minute of 99.9% purity hydrogen, and 6 standard liters per minute of nitrogen, was supplied through a gas injector apparatus similar to that described in FIGS. 4A and 4B, into an 50 mm outer diameter, 45 mm inner diameter quartz tube kept at 126 Torr. The precursor gas was subjected to 16 kW of incident 915 MHz microwave power in a plasma reactor apparatus similar to that described in FIG. 3. 100% of the ethane contained in the precursor gas was converted to hydrogen and hydrocarbon products with 3.3% methane yield. The hydrocarbon composition of the outflow gas leaving the reactor is described in Table 11 below.

TABLE 11

| Component | Mol % |
|---|---|
| acetylene | 18.34358 |
| hydrogen | 79.93364 |
| methane | 0.824195 |
| ethane | 0.003651 |
| ethylene | 0.383346 |
| propane | 0.006845 |
| propadiene | 0.008215 |
| propylene | 0 |
| diacetylene | 0.412097 |
| vinyl acetylene | 0.054307 |
| methyl acetylene | 0 |
| benzene | 0.028751 |
| toluene | 0.001369 |

Example 11

A flow of precursor gas, comprised of 8.6 standard liters per minute of 99.9% purity propane, 8.6 standard liters per minute of 99.9% purity butane, 88 standard liters per minute of 99.9% purity hydrogen, and 6 standard liters per minute of nitrogen, was supplied through a gas injector apparatus similar to that described in FIGS. 4A and 4B, into an 50 mm outer diameter, 45 mm inner diameter quartz tube kept at 70 Torr. The precursor gas was subjected to 16 kW of incident 915 MHz microwave power in a plasma reactor apparatus similar to that described in FIG. 3. 100% of the ethane contained in the precursor gas was converted to hydrogen and hydrocarbon products with a 3.2% methane yield. The hydrocarbon composition of the outflow gas leaving the reactor is described in Table 12 below.

TABLE 12

| Component | Mol % |
|---|---|
| Acetylene | 20.33077 |
| Hydrogen | 77.56967 |
| Methane | 1.155769 |
| Ethane | 0 |
| Ethylene | 0.293664 |
| Propane | 0.008498 |
| propadiene | 0.013692 |
| propylene | 0 |
| diacetylene | 0.549557 |
| vinyl acetylene | 0.046269 |
| methyl acetylene | 0 |
| Benzene | 0.030688 |
| Toluene | 0.001416 |

Example 12

A plasma reactor system as described in Example 1 that produces 250 liters of outflow gas per minute was used. After the vacuum pump in the system, solid carbon byproducts were removed with a simple in-line filter. Liquid hydrocarbon condensates containing greater than 14 carbon atoms were separated from the stream in a cold trap operating at −20° C. No further hydrocarbons were removed, and the outflow was directly passed through a stainless-steel vessel with an internal diameter of 8 inches containing 0.4 kg of blank 100-200 mesh α-alumina mixed with 1.8 kg of 100-200 mesh α-alumina doped with 3 wt % metallic palladium and 4 wt % metallic silver. The catalyst bed was maintained at 350° C. with internal, open-loop water cooling system. A gas mixture was obtained that contains 50% hydrogen, 11% ethylene, 0.5% ethane and 38.5% methane; acetylene content in the gas mixture was deliberately kept below 100 ppm.

Example 13

A plasma reactor system as described in Example 1 was used. A stream of 1 liter of outflow gas per minute was split off and processed further as described in this example. After the vacuum pump, solid carbon byproducts were removed with a ceramic, regenerative filter. Liquid hydrocarbon condensates containing greater than 10 carbon atoms were separated from the stream in a cold trap operating at −30° C. Afterwards, the outflow gas was passed through a stainless-steel vessel containing 20 grams high-surface area activated carbon, doped with 0.01% metallic palladium. The outflow gas at this point contained 85% hydrogen, 8% acetylene, 4% ethylene, and 0.6% vinyl acetylene and balance methane. The vinyl acetylene was removed by bubbling through a 500 mL vessel containing 300 mL of concentrated sulfuric acid at room temperature, then through a vessel containing 100 mL room temperature water to trap the volatized sulfuric acid. Finally, the gas stream was dried by passing through 10 grams of calcium sulfate desiccant.

Example 14

Precursor gas, comprised of 303 standard liters per minute of utility natural gas (having a composition of about 96.7% methane, about 2.7% ethane, and about 0.4% nitrogen), 628 standard liters per minute of 99.9% purity hydrogen, and 31 standard liters per minute of nitrogen, was supplied through a gas injector apparatus, similar to that described in FIGS. 4a and 4b, into a 50 mm outer diameter, 45 mm inner diameter quartz tube that was maintained at 260 mbara. The precursor gas was subjected to 98 kW of incident 915 MHz microwave power in a plasma reactor apparatus as described in FIG. 3. 90.6% of the hydrocarbons contained in the precursor gas was converted to hydrogen and hydrocarbon products. The reactor effluent gas composition excluding nitrogen is described in Table 13, as analyzed by a gas chromatograph.

TABLE 13

| Component | Mol % |
|---|---|
| Hydrogen | 84.5% |
| Methane | 2.74% |
| Ethylene | 0.168% |
| Acetylene | 12.2% |
| Propylene | 0.046% |
| Methyl Acetylene | 0.030% |
| Propadiene | 0.014% |
| Vinyl Acetylene | 0.046% |
| Diacetylene | 0.284% |
| Benzene | 0.017% |
| Toluene | 0.007% |

The outflow gas from the reactor was passed through an air-cooled heat sink and then passed through corrugated-paper filters before exiting the vacuum pump. The outflow gas then passed through a cold trap operating at 10° C. and additional filter.

EQUIVALENTS

While this invention has been particularly shown and described with references to preferred embodiments thereof, it will be understood by those skilled in the art that various changes in form and details may be made therein without departing from the scope of the invention encompassed by the appended claims. Unless otherwise indicated, all numbers expressing reaction conditions, quantities, amounts, ranges and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The invention claimed is:

1. A method for processing a methane-containing inflow gas to produce outflow gas products, comprising directing the methane-containing inflow gas into a system comprising: a gas delivery subsystem, a plasma reaction chamber, a microwave subsystem, a vacuum subsystem, and an effluent separation and disposal subsystem;

i. wherein the gas delivery subsystem is in fluid communication with the plasma reaction chamber and directs the methane-containing inflow gas into the plasma reaction chamber, the gas delivery subsystem comprising a delivery conduit and a gas injector, wherein the gas injector comprises an injector body comprising two or more separate gas feeds, a first gas feed conveying the methane-containing inflow gas into the plasma reaction chamber through a first set of one or more nozzles, and a second gas feed conveying a hydrogen-rich reactant gas into the plasma reaction chamber through a second set of one or more nozzles, wherein the delivery conduit is in fluid communication with the gas injector, wherein the delivery conduit comprises a feed gas conveying circuit that delivers the methane-containing inflow gas into the gas injector, wherein the delivery conduit further comprises an auxiliary gas conveying circuit that delivers the hydrogen-rich reactant gas into the gas injector, wherein the methane-containing inflow gas is delivered through the gas injector and into the plasma reaction chamber through a first pathway, and the hydrogen-rich reactant gas is delivered through the gas injector, and into the plasma reaction chamber through a second pathway that is separate from the first pathway, and wherein the gas delivery subsystem conveys the methane-containing inflow gas and the hydrogen-rich reactant gas into the plasma reaction chamber such that the ratio of the methane to the hydrogen is about 1:1 to about 1:3;

ii. wherein the plasma reaction chamber is disposed within an elongate reactor tube, the elongate reactor tube having a proximal end and a distal end and being dimensionally adapted for interaction with the microwave subsystem, iii. wherein the microwave subsystem comprises an applicator that interacts with the elongate reactor tube by directing the microwave energy into the plasma reaction chamber, wherein the plasma reaction chamber is disposed in a region of the elongate reactor tube that passes through the applicator and intersects it perpendicularly, wherein the microwave subsystem produces microwave energy and directs the microwave energy into the plasma reaction chamber to energize the methane-containing inflow gas and the hydrogen-rich reactant gas within the region of the elongate reactor tube to form a non-thermal plasma, and wherein the non-thermal plasma transforms the methane in the methane-containing inflow gas and the hydrogen in the hydrogen-rich reactant gas into the outflow gas products, wherein the outflow gas products comprise acetylene and hydrogen;

iv. wherein the outflow gas products flow within the plasma reaction chamber towards the distal end of the elongate reactor tube and emerge from the distal end to form an effluent stream that enters an effluent separation and disposal subsystem in fluid communication with the elongate reactor tube, iv. wherein the effluent separation and disposal subsystem comprises at least one of a hydrogen separation subsystem for removing the hydrogen from the effluent stream, an acetylene separation subsystem for removing the acetylene from the effluent stream, an adsorption column for removing higher-order hydrocarbons, and a temperature swing adsorber for removing higher acetylenes from the effluent stream, and v. wherein the vacuum subsystem maintains a first reduced pressure environment for the outflow gas products passing through the effluent separation and disposal system and wherein the first reduced pressure environment is between about 120 and about 280 Torr.

2. The method of claim 1, wherein the hydrogen-rich reactant gas comprises a recycled gas formed from a portion of the outflow gas products and wherein the recycled gas is delivered through a recycled gas conveying circuit into the auxiliary gas conveying circuit to form at least a portion of the hydrogen-rich reactant gas that enters into the gas injector.

3. The method of claim 2, wherein the hydrogen-rich reactant gas consists essentially of hydrogen.

4. The method of claim 1, wherein the two or more separate gas feeds are co-axially arranged.

5. The method of claim 1, wherein the elongate reactor tube comprises a proximal portion at the proximal end, wherein the gas injector conveys the methane-containing inflow gas and the hydrogen-rich reactant gas into the proximal portion, and wherein the methane-containing inflow gas and the hydrogen-rich reactant gas flow distally therefrom towards the plasma reaction chamber.

6. The method of claim 1, wherein at least one of the one or more nozzles in the first set of one or more nozzles or the second set of one or more nozzles is oriented at an angle to a longitudinal axis of the plasma reaction chamber or at an angle to a transverse axis of the plasma reaction chamber.

7. The method of claim 1, wherein at least one of the one or more nozzles in the first set of one or more nozzles or the second set of one or more nozzles is oriented at an angle to a longitudinal axis of the injector body or at an angle to a transverse axis of the injector body.

8. The method of claim 1, wherein the methane-containing inflow gas entering the plasma reaction chamber from the first set of one or more nozzles and the hydrogen-rich reactant gas entering the plasma reaction chamber from the second set of one or more nozzles create a vortex flow within the plasma reaction chamber.

9. The method of claim 1, wherein the hydrogen separation subsystem is downstream from the acetylene separation subsystem and in fluid communication therewith.

10. The method of claim 1, wherein the hydrogen separation subsystem is in fluid communication with a recycled gas conveying circuit, and wherein at least a portion of hydrogen removed from the effluent stream by the hydrogen separation subsystem is recycled into the recycled gas conveying circuit and into the auxiliary gas conveying circuit to form at least a portion of the hydrogen-rich reactant gas that enters the gas injector.

11. The method of claim 1, wherein the acetylene separation subsystem and the hydrogen separation subsystem are downstream from the temperature swing adsorber.

12. The method of claim 11, wherein the hydrogen separation subsystem is downstream from the acetylene separation subsystem.

13. The method of claim 1, wherein the effluent separation and disposal subsystem comprises at least two of the following: a hydrogen separation subsystem for removing hydrogen from the effluent stream, an acetylene separation subsystem for removing acetylene from the effluent stream, and a temperature swing adsorber for removing higher acetylenes from the effluent stream.

14. The method of claim 13, wherein the effluent separation and disposal subsystem comprises the hydrogen separation subsystem for removing hydrogen from the effluent stream, the acetylene separation subsystem for removing acetylene from the effluent stream, and the temperature swing adsorber for removing higher acetylenes from the effluent stream.

15. The method of claim 1, wherein the effluent separation and disposal subsystem further comprises a filter for removal of carbon solids upstream of the acetylene separation subsystem.

16. The method of claim 15, wherein the effluent separation and disposal subsystem further comprises a cold trap for removing higher order hydrocarbons as condensates.

17. The method of claim 16, wherein the acetylene separation subsystem and the hydrogen separation subsystem are downstream from the temperature swing adsorber.

18. The method of claim 17, wherein the hydrogen separation subsystem is downstream from the acetylene separation subsystem.

19. The method of claim 1, wherein the ratio is about 1:1 to about 1:2.

20. The method of claim 1, wherein the ratio is about 1:1 to about 1:1.5.

21. The method of claim 1, wherein the vacuum subsystem further produces a second reduced pressure environment within the elongate reactor tube and/or produces a third reduced pressure environment for the gas delivery subsystem.

22. The method of claim 21, wherein the vacuum subsystem produces both the second and the third reduced pressure environments.

23. The method of claim 21, wherein the second and third reduced pressure environments are each independently between about 120 to about 280 Torr.

24. The method of claim 22, wherein the second and third reduced pressure environments are each independently between about 120 to about 280 Torr.

25. The method of claim 22, wherein the first reduced pressure environment has a pressure that is at least about 10% higher than the pressure in the second reduced pressure environment and/or the third reduced pressure environment.

26. The method of claim 25, wherein the pressures in the second reduced pressure environment and the third reduced pressure environment are each independently between about 120 and about 280 Torr.

27. The method of claim 22, wherein the each of the pressures differs by less than about 10%.

* * * * *

UNITED STATES PATENT AND TRADEMARK OFFICE
CERTIFICATE OF CORRECTION

PATENT NO. : 11,471,852 B2
APPLICATION NO. : 17/402937
DATED : October 18, 2022
INVENTOR(S) : David S. Soane et al.

It is certified that error appears in the above-identified patent and that said Letters Patent is hereby corrected as shown below:

In the Claims

Column 91, Claim 1, Line 10: please delete "iv".

Signed and Sealed this
Thirty-first Day of January, 2023

Katherine Kelly Vidal
*Director of the United States Patent and Trademark Office*